United States Patent
Fiandor Roman et al.

(10) Patent No.: US 7,579,353 B2
(45) Date of Patent: Aug. 25, 2009

(54) PYRIDINONE DERIVATIVES AGAINST MALARIA

(75) Inventors: Jose Maria Fiandor Roman, Madrid (ES); Jose Maria Bueno Calderon, Madrid (ES); Araceli Mallo Rubio, Madrid (ES)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 11/817,508

(22) PCT Filed: Mar. 2, 2006

(86) PCT No.: PCT/EP2006/002160

§ 371 (c)(1),
(2), (4) Date: Jun. 25, 2008

(87) PCT Pub. No.: WO2006/094799

PCT Pub. Date: Sep. 14, 2006

(65) Prior Publication Data

US 2008/0287461 A1 Nov. 20, 2008

(30) Foreign Application Priority Data

Mar. 4, 2005 (EP) .................................. 05381011

(51) Int. Cl.
C07D 401/04 (2006.01)
A61K 31/444 (2006.01)
(52) U.S. Cl. ........................ 514/256; 514/333; 544/333; 546/257
(58) Field of Classification Search ........................ None
See application file for complete search history.

(56) References Cited

FOREIGN PATENT DOCUMENTS

| EP | 0 499 416 A | 8/1992 |
| WO | WO 91/13873 | 9/1991 |

OTHER PUBLICATIONS

Bradbury, Robert H., et al., "New nonpeptide angiotensin II receptor antagonists. 3. Synthesis, biological properties, and structure-activity relationships of 2-alkyl-4-(biphenylylmethoxy) pyridine derivatives." *Journal of Medicinal Chemistry* 36(9), 1245-54.

*Primary Examiner*—Zinna N Davis
(74) *Attorney, Agent, or Firm*—Reid S. Willis; John Lemanowicz

(57) ABSTRACT

4-pyridone derivatives of Formula (I) and pharmaceutically acceptable derivatives thereof, processes for their preparation, pharmaceutical formulations thereof and their use in chemotherapy of certain parasitic infections such as malaria, are provided.

13 Claims, No Drawings

PYRIDINONE DERIVATIVES AGAINST MALARIA

FIELD OF THE INVENTION

The invention relates to heterocyclic compounds and their use in chemotherapy. More specifically, this invention is concerned with certain 4-pyridone derivatives, processes for their preparation, pharmaceutical formulations thereof and their use in chemotherapy of certain parasitic infections such as malaria, and in particular infection by *Plasmodium falciparum*.

BACKGROUND OF THE INVENTION

Parasitic protozoal infections are responsible for a wide variety of diseases of medical and veterinary importance, including malaria in man and various coccidioses in birds, fish and mammals. Many of the diseases are life-threatening to the host and cause considerable economic loss in animal husbandry, such as species of *Eimeria, Theileria, Babesia, Cryptosporidium, Toxoplasma* (such as *Toxoplasma brucei*, African sleeping sickness and *Toxoplasma cruzi*, Chagas disease) and *Plasmodium* (such as *Plasmodium falciparum*), and the Mastigophora such as species of *Leishmania* (such as *Leishmania donovani*). Another parasitic organism of increasing concern is *Pneumocytis carini*, which can cause an often fatal pneumonia in immunodeficient or immunocompromised hosts, including those infected with HIV.

Malaria is one of the major disease problems of the developing world. The most virulent malaria-causing parasite in humans is the parasite *Plasmodium falciparum*, which is the cause of hundreds of millions of cases of malaria per annum, and is thought to cause over 1 million deaths each year, Breman, J. G., et al., (2001) Am. Trop. Med. Hyg. 64, 1-11. One problem encountered in the treatment of malaria is the build-up of resistance by the parasite to available drugs. Thus, there is a need to develop new antimalarial drugs.

A group of 3,5-dihalo-2,6-dialkyl-4-pyridinol derivatives (the tautomeric form of 4-pyridones) is described in U.S. Pat. No. 3,206,358 as having anticoccidial activity.

European Patent Application No. 123239 discloses combinations of the aforementioned 4-pyridinol derivatives with antiprotozoal naphthoquinones, e.g. antimalarial naphthoquinones, in a potentiating ratio.

PCT Patent Application No. WO 91/13873 A1 discloses a class of 4-pyridone derivatives which exhibit activity against protozoa, in particular against the malarial parasite *Plasmodium falciparum*, and species of *Eimeria* as well as the parasitic organism *Pneumocytis carinii*. It has been found that compounds according to the present invention, generically disclosed in WO 91/13873 A1, and having a specific substitution pattern, exhibit improved properties over those compounds specifically disclosed in WO 91/13873 A1.

SUMMARY OF THE INVENTION

This invention is directed to certain 4-pyridone derivatives, processes for their preparation, pharmaceutical compositions comprising such compounds and use of the compounds in the chemotherapy of certain parasitic infections such as malaria, and in particular infection by *Plasmodium falciparum*.

DETAILED DESCRIPTION OF THE INVENTION

The present invention provides at least one chemical entity chosen from compounds of Formula I:

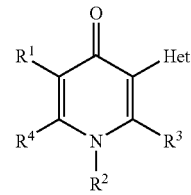

Wherein:
Het represents a 6-membered monocyclic heteroaromatic ring containing at least one nitrogen atom, wherein any carbon atom of Het is substituted with one or more groups Z, wherein Z represents a group selected from the list:
i) phenyl or methylenedioxyphenyl, either of which is optionally substituted with one or more groups selected from $R^X$;
ii) —$OC_{1-6}$alkylphenyl, wherein the phenyl group is optionally substituted with one or more groups selected from $R^X$;
iii) $C_{1-10}$alkyl, —Oaryl, —$C_{1-6}$alkylaryl, —$C_{2-6}$alkenylaryl or —$C_{2-6}$alkynylaryl, wherein any aryl group is optionally substituted with one or more groups selected from $R^X$;
$R^X$ represents halogen, cyano, —$NR^AR^B$, $C_{1-6}$alkyl, $C_{1-6}$alkoxy or $C_{1-6}$alkylS(O)$_m$—;
m represents 0-2;
$R^1$ represents halogen or hydrogen or cyano;
$R^2$ represents hydrogen, hydroxy, —C(O)$R^Y$, —C(O)OH or $C_{1-6}$alkyl optionally substituted by halogen, hydroxy, —C(O)OH, —C(O)$R^Y$ or —$NR^AR^B$;
$R^A$ and $R^B$ independently represent hydrogen or $C_{1-6}$alkyl;
$R^Y$ represents $C_{1-6}$alkoxy or $C_{1-6}$alkyl;
$R^3$ and $R^4$ are independently $C_{1-6}$alkyl;
and pharmaceutically acceptable derivatives thereof.

In an alternative embodiment the invention provides at least one chemical entity chosen from compounds of Formula A:

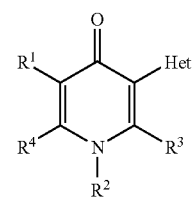

Wherein:
Het represents a 6-membered monocyclic heteroaromatic ring containing at least one nitrogen atom, optionally substituted with one or more groups Z, wherein Z represents a group selected from the list:
i) phenyl, optionally substituted with one or more groups selected from $R^X$;
ii) —$OC_{1-6}$alkylphenyl, optionally substituted with one or more groups selected from $R^X$;
iii) $C_{1-10}$alkyl, —Oaryl, $C_{2-6}$alkylaryl, $C_{2-6}$alkenylaryl or $C_{2-6}$alkynylaryl, wherein any aryl group is optionally substituted with one or more groups selected from the list: halogen, $C_{1-6}$alkyl, $C_{1-6}$alkoxy;
$R^X$ represents halogen, cyano, —$NR^AR^B$, $C_{1-6}$alkyl, $C_{1-6}$alkoxy or $C_{1-6}$alkylS(O)$_m$—;
m represents 0-2;
$R^1$ represents halogen or hydrogen or cyano;

$R^2$ represents hydrogen, hydroxy, —C(O)$R^Y$, —C(O)OH or $C_{1-6}$alkyl optionally substituted by halogen, hydroxy, —C(O)OH, —C(O)$R^Y$ or —N$R^A R^B$;

$R^A$ and $R^B$ independently represent hydrogen or $C_{1-6}$alkyl;

$R^Y$ represents $C_{1-6}$alkoxy or $C_{1-6}$alkyl;

$R^3$ and $R^4$ are independently $C_{1-6}$alkyl.

and pharmaceutically acceptable salts and solvates thereof.

In a further embodiment the invention provides at least one chemical entity chosen from compounds of Formula A as defined hereinabove, provided that the compound is other than 5'-Bromo-2',6'-dimethyl-2,3'-bipyridin-4'-(1'H)-one.

In a yet further embodiment the invention provides compounds of Formula A wherein Het represents a 6-membered monocyclic heteroaromatic ring containing at least one nitrogen atom which is substituted with one or more groups Z, wherein Z, $R^X$, m, $R^1$, $R^2$, $R^A$, $R^B$, $R^Y$, $R^3$ and $R^4$ are as defined for Formula A.

Terms and Definitions

As used herein, the term "alkyl" as a group or a part of a group refers to a linear or branched optionally substituted saturated hydrocarbon group, containing the number of carbon atoms as specified; examples of such groups include methyl, ethyl, propyl, isopropyl, n-butyl, sec-butyl, isobutyl, tert-butyl, n-pentyl, isopentyl, neopentyl, hexyl, heptyl, octyl, nonyl and decyl and the like. In one aspect of the invention, the alkyl moieties are $C_{1-4}$alkyl. In another aspect of the invention, alkyl is unsubstituted or substituted with one, two or three substituents. Unless otherwise specified, optional alkyl substituents include halogen and hydroxy. Typical examples of substituted alkyl include haloalkyl groups such as trifluoromethyl, difluoromethyl, 2,2,2-trifluoroethyl and the like.

As used herein, the term "alkoxy" refers to a linear or branched optionally substituted —O-alkyl group, containing from 1 to 6 carbon atoms; examples of such groups include methoxy, ethoxy, propoxy, prop-2-oxy, butoxy, but-2-oxy, methylprop-2-oxy, pentoxy or hexoxy and the like. In one aspect of the invention, the alkoxy moieties are $C_{1-4}$alkoxy. In another aspect of the invention, alkoxy is unsubstituted or substituted with one, two or three substituents. Optional substituents include halogen, for example fluorine. Typical examples of substituted alkyl include haloalkoxy groups such as trifluoromethoxy, difluoromethoxy, 2,2,2-trifluoroethoxy and the like.

As used herein, the term "alkenyl" refers to both straight and branched chain unsaturated hydrocarbon groups, wherein the hydrocarbon group has one or more positions of unsaturation, and the unsaturation is present as double bonds. Examples of alkenyl groups includes ethenyl (—CH=CH—) and propenyl (—CH$_2$—CH=CH—).

As used herein, the term "alkynyl" refers to both straight and branched chain saturated hydrocarbon groups, wherein the hydrocarbon group has one or more positions of unsaturation, and the unsaturation is present as triple bonds Examples of alkynyl groups include ethynyl (—C≡C—), propynyl, for example 1-propynyl (—C≡C—CH$_2$—) and butynyl, for example 1-butynyl (—C≡C—CH$_2$—CH$_2$—). For example, $C_2$-alkynyl refers to ethynyl, and $C_4$-alkynyl includes all isomers of butynyl.

As used herein, the term "aryl" refers to an optionally substituted aromatic group containing one, two or three conjugated or fused rings with at least one ring having a conjugated pi-electron system. In one aspect of the invention, aryl moieties are $C_{6-14}$aryl. In another aspect of the invention, aryl moieties are unsubstituted, monosubstituted, disubstituted or trisubstituted phenyl.

As used herein, "heteroaromatic" refers to an optionally substituted aromatic group comprising at least one heteroatom as specified, the aromatic group having a conjugated pi-electron system.

As used herein, "halogen" refers to a fluorine (fluoro), chlorine (chloro), bromine (bromo) or iodine (iodo) group.

All aspects and embodiments of the invention described herein are in respect of compounds of Formula I or compounds of Formula A, unless otherwise specified.

In one aspect of the invention, Het represents a 6-membered monocyclic heteroaromatic ring containing one or two nitrogen atoms, wherein any carbon atom of Het is substituted with one or more groups Z. In another aspect of the invention, Het represents pyridine or pyrimidine, wherein any carbon atom of Het is substituted with one or more groups Z. In yet another aspect of the invention, Het represents pyridine wherein any carbon atom of Het is substituted with one or more groups Z. In a still further aspect, Het represents pyrimidine wherein any carbon atom of Het is substituted with one or more groups Z.

In one aspect of the invention, Het is substituted with one group Z. In another aspect of the invention, Het is substituted with one group Z, wherein Z is positioned para to the point of attachment of Het to the pyridone ring.

In one aspect of the invention, Z represents phenyl or methylenedioxyphenyl, either of which is optionally substituted with one or more groups selected from $R^X$ wherein $R^X$ is as defined herein. In another aspect of the invention, Z represents phenyl, optionally substituted with one or more groups selected from $R^X$ wherein $R^X$ is as defined herein. In yet another aspect of the invention, Z represents phenyl substituted with one or two groups selected from $R^X$ wherein $R^X$ is as defined herein. When Z represents phenyl and is monosubstituted with $R^X$, in one aspect of the invention $R^X$ is ortho or para to the bond between Het and Z, in another aspect of the invention $R^X$ is para.

In one aspect of the invention, Z represents —O$C_{1-6}$alkylphenyl, for example —Obenzyl, wherein Z is optionally substituted with one or more groups selected from $R^X$, wherein $R^X$ is as defined hereinbelow. In another aspect of the invention, Z represents —Obenzyl substituted with one or two groups selected from $R^X$ wherein $R^X$ is as defined hereinbelow. When Z represents —Obenzyl and is monosubstituted with $R^X$, in one aspect of the invention $R^X$ is ortho or para to the bond between Het and Z, in another aspect of the invention $R^X$ is para.

In one aspect of the invention, Z represents $C_{1-10}$alkyl, —Oaryl, —$C_{1-6}$alkylaryl, —$C_{2-6}$alkenylaryl or —$C_{2-6}$alkynylaryl, wherein any aryl group is optionally substituted with one or more groups selected from the list: halogen, $C_{1-6}$alkyl, $C_{1-6}$alkoxy. In another aspect of the invention, Z represents $C_{1-10}$alkyl, —Oaryl, —$C_{1-6}$alkylaryl or —$C_{2-6}$alkynylaryl, wherein any aryl group is optionally substituted with one or more groups selected from the list: halogen, $C_{1-6}$alkyl, $C_{1-6}$alkoxy. In yet another aspect of the invention, Z represents $C_{1-10}$alkyl, phenoxy, —$C_{2-6}$alkylaryl or —$C_{2-6}$alkynylaryl, wherein any aryl group is optionally substituted with one or more groups selected from the list: halogen, $C_{1-6}$alkyl, $C_{1-6}$alkoxy. In a still further aspect of the invention, Z represents a) $C_{1-10}$alkyl, wherein the alkyl group is substituted as defined herein, or b) $C_{5-10}$alkyl, wherein the alkyl group is unsubstituted, or c) phenoxy, or d) —$C_2$alkylaryl; wherein any aryl group is optionally substituted with one or more groups selected from the list: halogen, $C_{1-6}$alkyl, $C_{1-6}$alkoxy. In one aspect of the invention optional substituents for any aryl group of Z include fluorine, trifluoromethyl and trifluoromethoxy. When Z is monosubstituted, in one aspect the substituent is meta or para to the bond between Het and Z.

In one aspect of the invention, $R^X$ represents halogen, $C_{1-6}$alkyl or $C_{1-6}$alkoxy. In another aspect of the invention, $R^X$ represents chlorine, fluorine, unsubstituted $C_{1-6}$alkyl, trifluoromethyl or trifluoromethoxy. In yet another aspect of the invention, $R^X$ represents chlorine, fluorine, trifluoromethyl or trifluoromethoxy. In a still further aspect, $R^X$ represents fluorine or trifluoromethyl. In another aspect, $R^X$ represents fluorine.

In one aspect of the invention, $R^1$ represents halogen; in a further aspect $R^1$ represents chlorine or bromine.

In one aspect of the invention, $R^2$ represents hydrogen or hydroxy; in a further aspect, $R^2$ represents hydrogen.

In one aspect of the invention, $R^3$ and $R^4$ represent $C_{1-4}$alkyl, in a further aspect, $R^3$ and $R^4$ represent methyl.

The meaning of any functional group or substituent thereon at any one occurrence in Formula I or Formula A, or any subformula thereof, is independent of its meaning, or any other functional group's or substituent's meaning, at any other occurrence, unless stated otherwise. It is to be understood that the present invention covers all combinations of the groups according to different aspects of the invention as described hereinabove.

In one aspect, chemical entities useful in the present invention may be at least one chemical entity selected from the list:
5-Bromo-2,6-dimethyl-6'-{[4-(trifluoromethoxy)benzyl]oxy}-3,3'-bipyridin-4(1H)-one;
5-Bromo-2,6-dimethyl-6'-{[3-(trifluoromethyl)benzyl]oxy}-3,3'-bipyridin-4(1H)-one;
5-Bromo-2,6-dimethyl-6'-{[4-(trifluoromethyl)benzyl]oxy}-3,3'-bipyridin-4(1H)-one;
5-Bromo-2,6-dimethyl-6'-{[2-(trifluoromethyl)benzyl]oxy}-3,3'-bipyridin-4(1H)-one;
5-Bromo-2,6-dimethyl-6'-{[3,5-bis(trifluoromethyl)benzyl]oxy}-3,3'-bipyridin-4(1H)-one;
5-Bromo-6'-{[4-fluorobenzyl]oxy}-2,6-dimethyl-3,3'-bipyridin-4(1H)-one;
5-Bromo-6'-{[3,5-difluorobenzyl]oxy}-2,6-dimethyl-3,3'-bipyridin-4(1H)-one;
5-Chloro-2,6-dimethyl-6'-{[4-(trifluoromethoxy)benzyl]oxy}-3,3'-bipyridin-4(1H)-one;
5-Chloro-2,6-dimethyl-6'-{[3-(trifluoromethyl)benzyl]oxy}-3,3'-bipyridin-4(1H)-one;
5-Chloro-2,6-dimethyl-6'-{[4-(trifluoromethyl)benzyl]oxy}-3,3'-bipyridin-4(1H)-one;
5-Chloro-2,6-dimethyl-6'-{[2-(trifluoromethyl)benzyl]oxy}-3,3'-bipyridin-4(1H)-one;
5-Chloro-2,6-dimethyl-6'-{[3,5-bis(trifluoromethyl)benzyl]oxy}-3,3'-bipyridin-4(1H)-one;
5-Chloro-6'-{[4-fluorobenzyl]oxy}-2,6-dimethyl-3,3'-bipyridin-4(1H)-one;
5-Chloro-6'-{[3,5-difluorobenzyl]oxy}-2,6-dimethyl-3,3'-bipyridin-4(1H)-one;
5-Bromo-2,6-dimethyl-6'-{4-[(trifluoromethyl)oxy]phenyl}-3,3'-bipyridin-4(1H)-one;
5-Bromo-2,6-dimethyl-6'-{4-[trifluoromethyl]phenyl}-3,3'-bipyridin-4(1H)-one;
5-Bromo-2,6-dimethyl-6'-{3-[trifluoromethyl]phenyl}-3,3'-bipyridin-4(1H)-one;
5-Bromo-2,6-dimethyl-6'-{2-[trifluoromethyl]phenyl}-3,3'-bipyridin-4(1H)-one;
5-Bromo-6'-(4-chlorophenyl)-2,6-dimethyl-3,3'-bipyridin-4(1H)-one;
5-Bromo-6'-(3-chlorophenyl)-2,6-dimethyl-3,3'-bipyridin-4(1H)-one;
5-Bromo-6'-(2-chlorophenyl)-2,6-dimethyl-3,3'-bipyridin-4(1H)-one;
5-Bromo-6'-(4-fluorophenyl)-2,6-dimethyl-3,3'-bipyridin-4(1H)-one;
5-Bromo-6'-(2-fluorophenyl)-2,6-dimethyl-3,3'-bipyridin-4(1H)-one;
5-Bromo-2,6-dimethyl-6'-{2,4-bis[trifluoromethyl]phenyl}-3,3'-bipyridin-4(1H)-one;
5-Bromo-2,6-dimethyl-6'-{3,5-bis[trifluoromethyl]phenyl}-3,3'-bipyridin-4(1H)-one;
5-Bromo-6'-(4-n-butylphenyl)-2,6-dimethyl-3,3'-bipyridin-4(1H)-one;
5-Chloro-2,6-dimethyl-6'-{4-[(trifluoromethyl)oxy]phenyl}-3,3'-bipyridin-4(1H)-one;
5-Chloro-2,6-dimethyl-6'-{3-[(trifluoromethyl)oxy]phenyl}-3,3'-bipyridin-4(1H)-one;
5-Chloro-2,6-dimethyl-6'-{2-[(trifluoromethyl)oxy]phenyl}-3,3'-bipyridin-4(1H)-one;
5-Chloro-2,6-dimethyl-6'-{4-[trifluoromethy]phenyl}-3,3'-bipyridin-4(1H)-one;
5-Chloro-2,6-dimethyl-6'-{3-[trifluoromethy]phenyl}-3,3'-bipyridin-4(1H)-one;
5-Chloro-2,6-dimethyl-6'-{2-[trifluoromethy]phenyl}-3,3'-bipyridin-4(1H)-one;
5-Chloro-6'-(4-chlorophenyl)-2,6-dimethyl-3,3'-bipyridin-4(1H)-one;
5-Chloro-6'-(3-chlorophenyl)-2,6-dimethyl-3,3'-bipyridin-4(1H)-one;
5-Chloro-6'-(2-chlorophenyl)-2,6-dimethyl-3,3'-bipyridin-4(1H)-one;
5-Chloro-6'-(4-fluorophenyl)-2,6-dimethyl-3,3'-bipyridin-4(1H)-one;
5-Chloro-6'-(2-fluorophenyl)-2,6-dimethyl-3,3'-bipyridin-4(1H)-one;
5-Chloro-2,6-dimethyl-6'-{4-[(trifluoromethyl)oxy]phenyl}-3,3'-bipyridin-4(1H)-one hydrochloride salt;
5-Bromo-6'-(4-n-butylphenyl)-2,6-dimethyl-3,3'-bipyridin-4(1H)-one hydrochloride salt;
5-Bromo-2,6-dimethyl-6'-{[4-(trifluoromethyl)phenyl]ethynyl}-3,3'-bipyridin-4(1H)-one;
5-Chloro-2,6-dimethyl-6'-{[4-(trifluoromethyl)phenyl]ethynyl}-3,3'-bipyridin-4(1H)-one;
5-Chloro-6'-{[2,4-difluorophenyl]ethynyl}-2,6-dimethyl-3,3'-bipyridin-4(1H)-one;
5-Bromo-2,6-dimethyl-6'-{2-[3-(trifluoromethyl)phenyl]ethyl}-3,3'-bipyridin-4(1H)-one;
5-Chloro-2,6-dimethyl-6'-{2-[3-(trifluoromethyl)phenyl]ethyl}-3,3'-bipyridin-4(1H)-one;
5-Chloro-2,6-dimethyl-6'-{2-[4-(trifluoromethyl)phenyl]ethyl}-3,3'-bipyridin-4(1H)-one;
5-Chloro-6'-{2-[2,4-difluorophenyl]ethyl}-2,6-dimethyl-3,3'-bipyridin-4(1H)-one;
5-Chloro-6'-(n-heptyl)-2,6-dimethyl-3,3'-bipyridin-4(1H)-one;
5-Chloro-6'-(n-heptyl)-2,6-dimethyl-3,3'-bipyridin-4(1H)-one hydrochloride salt;
5-Chloro-2,6-dimethyl-6'-({4-[(trifluoromethyl)oxy]phenyl}oxy)-3,3'-bipyridin-4(1H)-one;
3-Chloro-2,6-dimethyl-5-(5-nonyl-2-pyrimidinyl)-4(1H)-pyridinone;
3-Chloro-2,6-dimethyl-5-{2-[4-(trifluoromethyl)phenyl]-5-pyrimidinyl}-4(1H)-pyridinone;
5'-Chloro-2',6'-dimethyl-5-{2-[4-(trifluoromethyl)phenyl]ethyl}-2,3'-bipyridin-4'(1'H-one;
5-Bromo-2,6-dimethyl-3-(6-{[3,4-methylenedioxy]phenyl}-3,3'-bipyridin-4(1H)-one;

5-Chloro-2,6-dimethyl-3-(6-{[3,4-methylenedioxy]phenyl}-3,3'-bipyridin-4(1H)-one;

5-chloro-6'-[2-chloro-4-(trifluoromethyl)phenyl]-2,6-dimethyl-3,3'-bipyridin-4(1H)-one;

5-chloro-6'-[2-fluoro-5-(trifluoromethyl)phenyl]-2,6-dimethyl-3,3'-bipyridin-4(1H)-one;

5-chloro-6'-[2-chloro-5-(trifluoromethyl)phenyl]-2,6-dimethyl-3,3'-bipyridin-4(1H)-one;

5-chloro-6'-[2-fluoro-4-(trifluoromethyl)phenyl]-2,6-dimethyl-3,3'-bipyridin-4(1H)-one;

5-Chloro-2,6-dimethyl-6'-{[4-butyloxy]phenyl}-3,3'-bipyridin-4(1H)-one;

5-Chloro-2,6-dimethyl-6'-{[3-chloro,4-propyloxy]phenyl}-3,3'-bipyridin-4(1H)-one;

5-Chloro-2,6-dimethyl-6'-{[4-isopropyloxy]phenyl}-3,3'-bipyridin-4(1H)-one;

5-Chloro-2,6-dimethyl-6'-{4-[2,2,2-trifluoroethoxy]phenyl}-3,3'-bipyridin-4(1H)-one;

5-Chloro-2,6-dimethyl-6'-{4-[difluoromethyl]phenyl}-3,3'-bipyridin-4(1H)-one;

3-Chloro-2,6-dimethyl-5-(5-(2-(4-trifluoromethylphenyl))pyrimidinyl)pyridin-4(1H)-one;

and pharmaceutically acceptable derivatives thereof.

As used herein, the term "pharmaceutically acceptable derivative", means any pharmaceutically acceptable salt, solvate, or prodrug e.g. ester or carbamate of a compound of Formula I or Formula A, which upon administration to the recipient is capable of providing (directly or indirectly) a compound of Formula I or Formula A, or an active metabolite or residue thereof. Such derivatives are recognizable to those skilled in the art, without undue experimentation. Nevertheless, reference is made to the teaching of Burger's Medicinal Chemistry and Drug Discovery, 5th Edition, Vol 1: Principles and Practice, which is incorporated herein by reference to the extent of teaching such derivatives. In one aspect of the invention pharmaceutically acceptable derivatives are salts, solvates, esters and carbamates. In another aspect of the invention pharmaceutically acceptable derivatives are salts, solvates and esters. In a further aspect, pharmaceutically acceptable derivatives are salts and solvates.

An ester of a compound of Formula I or Formula A may be hydrolysable under in vivo conditions in the human body. Suitable pharmaceutically acceptable in vivo hydrolysable ester groups include those which break down readily in the human body to leave the parent acid or the salt thereof. An ester may be formed at a carboxylic acid (—COOH) group of a compound of Formula I or Formula A using methods well known in the art involving reaction with the corresponding alcohol. An ester may alternatively be formed at a hydroxy group (OH) of a compound of Formula I or Formula A using methods well known in the art involving reaction with the corresponding acid. For example, esters may be $C_{1-6}$alkyl esters, wherein alkyl is as defined herein, e.g. methyl esters, ethyl esters and the like.

It will be appreciated that pharmaceutically acceptable salts of the compounds according to Formula I or Formula A can be prepared. Indeed, in certain embodiments of the invention, pharmaceutically acceptable salts of the compounds according to Formula I or Formula A may be preferred over the respective free base or free acid because such salts impart greater stability or solubility to the molecule thereby facilitating formulation into a dosage form. The compounds of the present invention may also be administered as a pharmaceutically acceptable salt. Accordingly, the invention is further directed to pharmaceutically acceptable salts of the compounds according to Formula I or Formula A.

As used herein, the term "pharmaceutically acceptable salts" refers to salts that retain the desired biological activity of the subject compound and exhibit minimal undesired toxicological effects. For a review on suitable salts see Berge et al, J. Pharm. Sci., 1977, 66, 1-19. The term "pharmaceutically acceptable salts" includes both pharmaceutically acceptable acid addition salts and pharmaceutically acceptable base addition salts. These pharmaceutically acceptable salts may be prepared in situ during the final isolation and purification of the compound, or by separately reacting the purified compound in its free acid or free base form with a suitable base or acid, respectively. The salt may precipitate from solution and be collected by filtration or may be recovered by evaporation of the solvent.

In certain embodiments, compounds according to Formula I or Formula A may contain an acidic functional group and may therefore be capable of forming pharmaceutically acceptable base addition salts by treatment with a suitable base. A pharmaceutically acceptable base addition salt may be formed by reaction of a compound of Formula I or Formula A with a suitable inorganic or organic base (e.g. ammonia, triethylamine, ethanolamine, triethanolamine, choline, arginine, lysine or histidine), optionally in a suitable solvent such as an organic solvent, to give the base addition salt which is usually isolated for example by crystallisation and filtration. Pharmaceutically acceptable base salts include ammonium salts and salts with organic bases, including salts of primary, secondary and tertiary amines, including aliphatic amines, aromatic amines, aliphatic diamines, and hydroxy alkylamines, such as methylamine, ethylamine, isopropylamine, diethylamine, ethylenediamine, ethanolamine, trimethylamine, dicyclohexyl amine, diethanolamine, cyclohexylamine and N-methyl-D-glucamine. Other suitable pharmaceutically acceptable base salts include pharmaceutically acceptable metal salts, for example pharmaceutically acceptable alkali-metal or alkaline-earth-metal salts such as hydroxides, carbonates and bicarbonates of sodium, potassium, lithium, calcium, magnesium, aluminium, and zinc; in particular pharmaceutically acceptable metal salts of one or more carboxylic acid moieties that may be present in the compound of Formula I or Formula A.

In certain embodiments, compounds according to Formula I or Formula A may contain a basic functional group and may therefore be capable of forming pharmaceutically acceptable acid addition salts by treatment with a suitable acid. A pharmaceutically acceptable acid addition salt may be formed by reaction of a compound of Formula I or Formula A with a suitable inorganic or organic acid (such as hydrobromic, hydrochloric, sulfuric, sulfamic, nitric, phosphoric, perchloric, succinic, maleic, hydroxymaleic, acrylic, formic, acetic, hydroxyacetic, phenylacetic, butyric, isobutyric, propionic, fumaric, citric, tartaric, lactic, mandelic, benzoic, o-acetoxybenzoic, chlorobenzoic, methylbenzoic, dinitrobenzoic, hydroxybenzoic, methoxybenzoic salicylic, glutamaic, stearic, ascorbic, palmitic, oleic, pyruvic, pamoic, malonic, lauric, glutaric aspartic, p-toluenesulfonic, benzenesulfonic, methanesulfonic, ethanesulfonic, 2-hydroxyethanesulfonic, naphthalenesulfonic (e.g. 2-naphthalenesulfonic), p-aminobenzenesulfonic (i.e. sulfanilic), hexanoic, heptanoic, or phthalic acid), optionally in a suitable solvent such as an organic solvent, to give the salt which is usually isolated for example by crystallisation and filtration. A pharmaceutically acceptable acid addition salt of a compound of Formula I or Formula A can comprise or be for example a hydrobromide, hydrochloride, hydroiodide, sulfate, bisulfate, nitrate, phosphate, hydrogen phosphate, succinate, maleate, malate, formate, acetate, trifluoroacetate, saccharate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate), methanesulphonic, ethanesulphonic, p-toluenesulphonic, isethionate or hexanoate salt. In one embodiment, a pharmaceutically acceptable acid addition salt of a compound of Formula I or Formula A can comprise or be a salt of a strong acid, for example a hydrobromide, hydrochloride, hydroiodide, sulfate, nitrate, perchlorate or phosphate salt. In another embodiment there is provided the hydrochloric acid salt of a compound of Formula I or Formula A.

The invention includes within its scope all possible stoichiometric and non-stoichiometric forms of the salts of the compounds of Formula I or Formula A.

As used herein, the term "compounds of the invention" means both the compounds according to Formula I or Formula A and the pharmaceutically acceptable derivatives thereof. The terms "a compound of the invention" and "chemical entity" also appear herein and refer to both a compound according to Formula I or Formula A and its pharmaceutically acceptable derivatives.

The compounds of the invention may exist as solids or liquids, both of which are included in the invention. In the solid state, the compounds of the invention may exist as either amorphous material or in crystalline form, or as a mixture thereof. It will be appreciated that pharmaceutically acceptable solvates of compounds of the invention may be formed wherein solvent molecules are incorporated into the crystalline lattice during crystallisation. Solvates may involve non-aqueous solvents such as ethanol, isopropanol, dimethylsulfoxide (DMSO), acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." The invention includes all such solvates.

It will be appreciated that compounds of the invention can exist in different tautomeric forms. In particular, compounds of Formula I or Formula A may exist in the 4-pyridinol tautomeric form as follows

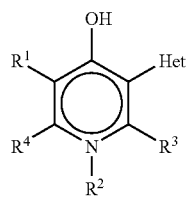

All possible tautomeric forms of the compounds of Formula I or Formula A are contemplated to be within the scope of the present invention. In one aspect of the invention there is provided compounds of Formula I or Formula A in the 4-pyridone tautomeric form.

It will further be appreciated that compounds of the invention which contain one or more alkenyl groups may be present as a mixture of E and Z isomers with respect to the geometry about each double bond. The mixture may contain E and Z isomers in equal amounts, or the mixture may contain an excess of either Z or E isomer. Compounds of the invention may alternatively be present in their respective pure E and Z geometric isomeric form about each double bond.

It will also be appreciated that compounds of the invention which exist as polymorphs, enantiomers, diastereomers and mixtures thereof are all contemplated to be within the scope of the present invention.

The compounds of the invention show advantageous properties, they may be more efficacious, may show greater selectivity for the target enzymes, may have fewer side effects, may have a longer duration of action, may be more bioavailable by the preferred route, or they may have other more desirable properties than similar known compounds.

According to another aspect of the invention there is provided a compound of Formula I or Formula A or a pharmaceutically acceptable derivative thereof for use in human or veterinary medical therapy.

The invention relates to heterocyclic compounds and their use in chemotherapy. More specifically, this invention is concerned with certain 4-pyridone derivatives, processes for their preparation, pharmaceutical formulations thereof and their use in the chemotherapy of certain parasitic infections such as malaria, and in particular infection by *Plasmodium falciparum*.

The compounds of the invention can be useful in the treatment of certain parasitic infections such as parasitic protozoal infections by the malarial parasite *Plasmodium falciparum*, species of *Eimeria, Pneumocytis carnii, Trypanosoma cruzi, Trypanosoma brucei* and *Leishmania donovani*. In particular, the compounds of the invention can be useful for treatment of infection by *Plasmodium falciparum*. Accordingly, the invention is directed to methods of treating such conditions.

In one aspect of the invention, there is provided a compound of Formula I or Formula A or a pharmaceutically acceptable derivative thereof, for use in therapy, for example the treatment of parasitic protozoal infections such as malaria, for example infection by *Plasmodium falciparum*.

In another aspect of the invention there is provided the use of a compound of Formula I or Formula A or a pharmaceutically acceptable derivative thereof in the manufacture of a medicament for the treatment of parasitic protozoal infections such as malaria, for example a condition caused by infection by *Plasmodium falciparum*.

In another aspect of the invention there is provided a method for the treatment of a human or animal subject suffering from a parasitic protozoal infection such as malaria, for example infection by *Plasmodium falciparum*, comprising administering to said human or animal subject an effective amount of a compound of Formula I or Formula A or a pharmaceutically acceptable derivative thereof, or a pharmaceutical composition comprising a compound of Formula I or Formula A or a pharmaceutically acceptable derivative thereof.

The methods of treatment of the invention comprise administering a safe and effective amount of a compound according to Formula I or Formula A or a pharmaceutically acceptable derivative thereof to a patient in need thereof.

As used herein, "treatment" means: (1) the amelioration or prevention of the condition being treated or one or more of the biological manifestations of the condition being treated, (2) the interference with (a) one or more points in the biological cascade that leads to or is responsible for the condition being treated or (b) one or more of the biological manifestations of the condition being treated, or (3) the alleviation of one or more of the symptoms or effects associated with the condition being treated. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "safe and effective amount" means an amount of the compound sufficient to significantly induce a positive modification in the condition to be treated but low enough to avoid serious side effects (at a reasonable benefit/risk ratio) within the scope of sound medical judgment. A safe and effective amount of a compound of the invention will vary with the particular compound chosen (e.g. depending on the potency, efficacy, and half-life of the compound); the route of administration chosen; the nature of the infection and/or condition being treated; the severity of the infection and/or condition being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human or other animal.

The compounds of the invention may be administered by any suitable route of administration, including systemic administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes dermal application to the skin as well as intraocular, buccal (e.g. sub-lingually), rectal, intravaginal, and intranasal administration.

The compounds of the invention may be administered once only, or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. The dosage will also vary according to the nature of the intended treatment, wherein "treatment" is as hereinbelow defined, for example a greater dose of compound may be given for amelioration as compared with prevention of a condition being treated. Suitable dosing regimens for a compound of the invention depend on the pharmacokinetic properties of that compound, such as absorption, distribution, and half-life, which can be determined by the skilled artisan. In addition, suitable dosing regimens for a compound of the invention, including the duration such regimens are administered, depend on the route of administration of the compound, on the condition being treated, the severity of the condition being treated, the age and physical condition of the patient being treated, the medical history of the patient to be treated, the nature of any concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change. It will also be appreciated that if the compounds of the present invention are administered in combination with one or more additional active therapeutic agents as discussed further hereinbelow, the dosing regimen of the compounds of the invention may also vary according to the nature and amount of the one or more additional active therapeutic agents as necessary.

Typical daily dosages may vary depending upon the particular route of administration chosen. Typical daily dosages for oral administration range from about 0.01 to about 25 mg/kg, in one embodiment from about 0.1 to about 14 mg/kg. Typical daily dosages for parenteral administration range from about 0.001 to about 10 mg/kg; in one embodiment from about 0.01 to about 6 mg/kg.

The compounds of Formula I or Formula A may also be used in combination with other active therapeutic agents. The invention thus provides, in a further aspect, a combination comprising a compound of Formula I or Formula A or a pharmaceutically acceptable derivative thereof together with a further active therapeutic agent. When a compound of Formula I or Formula A or a pharmaceutically acceptable derivative thereof is used in combination with a second active therapeutic agent which is active against the same disease state the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian.

The compounds of the present invention may be used alone or in combination with one or more additional active therapeutic agents, such as other antiparasitic drugs, for example antimalarial drugs.

Such other active therapeutic agents include antimalarial drugs, such as folates (e.g. chloroquine, mefloquine, primaquine pyrimethamine, quinine, artemisinin, halofantrine, doxycycline, amodiquine, atovaquone, tafenoquine) and antifolates (e.g. dapsone, proguanil, sulfadoxine, pyrimethamine, chlorcycloguanil, cycloguanil).

The combinations referred to above may conveniently be presented for use in the form of a pharmaceutical formulation and thus pharmaceutical formulations comprising a combination as defined above together with a pharmaceutically acceptable carrier and/or excipient comprise a further aspect of the invention. The individual components of such combinations may be administered either sequentially or simultaneously in separate or combined pharmaceutical formulations by any convenient route.

When administration is sequential, either the compound of the present invention or the one or more additional active therapeutic agent(s) may be administered first. When administration is simultaneous, the combination may be administered either in the same or different pharmaceutical composition. When combined in the same formulation it will be appreciated that the compound of the present invention and the one or more additional active therapeutic agent(s) must be stable and compatible with each other and the other components of the formulation. When formulated separately the compound of the present invention and the one or more additional active therapeutic agent(s) may be provided in any convenient formulation, conveniently in such manner as are known for such compounds in the art.

Compositions

The compounds of the invention will normally, but not necessarily, be formulated into pharmaceutical compositions prior to administration to a patient. In one aspect, the invention is directed to pharmaceutical compositions comprising a compound of the invention. In another aspect the invention is directed to pharmaceutical compositions comprising a compound of the invention and a pharmaceutically acceptable carrier and/or excipient. The carrier and/or excipient must be "acceptable" in the sense of being compatible with the other ingredients of the formulation and not deleterious to the recipient thereof.

The pharmaceutical compositions of the invention may be prepared and packaged in bulk form wherein a safe and effective amount of a compound of the invention can be extracted and then given to the patient such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from about 0.1 to 100 mg, in another aspect 0.1 mg to about 50 mg of a compound of the invention.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional active therapeutic compounds. The pharmaceutical compositions of the invention typically contain more than one pharmaceutically acceptable excipient. However, in certain embodiments, the pharmaceutical compositions of the invention contain one pharmaceutically acceptable excipient.

As used herein, the term "pharmaceutically acceptable" means suitable for pharmaceutical use.

The compound of the invention and the pharmaceutically acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carriage or transport of the compound or compounds of the invention from one organ, or portion of the body, to another organ, or portion of the body, once administered to the patient. Certain pharmaceutically acceptable excipients may be chosen for their ability to enhance patient compliance.

Suitable pharmaceutically acceptable excipients include the following types of excipients: binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The pharmaceutical compositions of the invention are prepared using techniques and methods known to those skilled in the art. Some of the methods commonly used in the art are described in Remington's Pharmaceutical Sciences (Mack Publishing Company).

In one aspect, the invention is directed to a solid or liquid oral dosage form such as a liquid, tablet, lozenge or a capsule, comprising a safe and effective amount of a compound of the invention and a carrier. The carrier may be in the form of a diluent or filler. Suitable diluents and fillers in general include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. A liquid dosage form will generally consist of a suspension or solution of the compound or salt in a liquid carrier for example, ethanol, olive oil, glycerine, glucose (syrup) or water (e.g. with an added flavouring, suspending, or colouring agent). Where the composition is in the form of a tablet or lozenge, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers or a semi solid e.g. mono di-glycerides of capric acid, Gelucire™ and Labrasol™, or a hard capsule shell e.g gelatin. Where the composition is in the form of a soft shell capsule e.g. gelatin, any pharmaceutical carrier routinely used for preparing dispersions or suspensions may be considered, for example aqueous gums or oils, and may be incorporated in a soft capsule shell.

An oral solid dosage form may further comprise an excipient in the form of a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise an excipient in the form of a disintegrant. Suitable disintegrants include crospovidone, sodium starch glycolate, croscarmelose, alginic acid, and sodium carboxymethyl cellulose. The oral solid dosage form may further comprise an excipient in the form of a lubricant. Suitable lubricants include stearic acid, magnesium stearate, calcium stearate, and talc.

There is further provided by the present invention a process of preparing a pharmaceutical composition, which process comprises mixing at least one compound of Formula I or Formula A or a pharmaceutically acceptable derivative thereof, together with a pharmaceutically acceptable carrier and/or excipient.

Preparations for oral administration may be suitably formulated to give controlled/extended release of the active compound.

All publications, including but not limited to patents and patent applications cited in this specification are herein incorporated by reference as if each individual publication were specifically and individually indicated to be incorporated by reference as though fully set forth.

Abbreviations

In describing the invention, chemical elements are identified in accordance with the Periodic Table of the Elements. Abbreviations and symbols utilized herein are in accordance with the common usage of such abbreviations and symbols by those skilled in the chemical arts. The following abbreviations are used herein:

ACN acetonitrile
AcOEt ethyl acetate
approx. approximately
brine saturated aqueous sodium chloride
$CDCl_3$ deuterated chloroform
cpm counts per minute (unit of radioactivity)
DCM dichloromethane
DAST diethylaminosulfur trifluoride
DMSO dimethylsulfoxide
DMSO-$d_6$ deuterated dimethylsulfoxide
DMF N,N-dimethylformamide
$CD_3OD$ deuterated methanol
human sera AB Serum obtained from human blood type AB
HEPES 4-(2-Hydroxyethyl)piperazine-1-ethanesulfonic acid
Hex hexane
HPLC High Performance Liquid Chromatography
Incomplete blood donation a volume of blood lower than 450 ml used for research
max. maximum
MeOH methanol
$MgSO_4$ magnesium sulfate
NaTaurochol. sodium Taurocholic
$NaHCO_3$ sodium bicarbonate
$Na_2SO_4$ sodium sulfate
NBS N-bromosuccinimide
NCS N-chlorosuccinimide
PRBCs parasitized red blood cells
RBCs red blood cells
cat ref. catalogue reference
TEA triethylamine
TCCA trichloroisocyanuric acid
THF tetrahydrofuran
NMR Nuclear Magnectic Resonance spectroscopy
RPMI Roswell Park Memorial Institute medium
ES MS Electrospray mass spectrometry Compound Preparation The general procedures used to synthesise the compounds of Formula I are described in reaction Schemes 1-31 and are illustrated in the Examples.

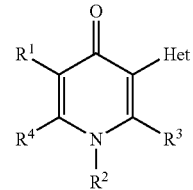

I

It will be appreciated by a person skilled in the art that compounds of Formula A may be synthesised using processes analagous to those described for compounds of Formula I hereinbelow.

Throughout the specification, general Formulae are designated by Roman numerals I, II, III, IV etc. Subsets of compounds of Formula I are defined as Ia, Ib, Ic, Id, Ie, If and Ig; subsets of other Formulae are expressed in an analogous fashion.

Compounds of Formula Ia, Ib, Ic or Id, which are compounds of Formula I wherein $R^1$ is halogen, $R^2$ is hydrogen, $R^3$ and $R^4$ are independently $C_{1-6}$alkyl, Het is pyridyl substituted with group Z, wherein Z is Ia: $OC_{1-6}$phenyl, optionally substituted with $R^X$ as defined for Formula I above;

Ib: phenyl, or methylenedioxyphenyl, either of which is optionally substituted with $R^X$ as defined for Formula I above;

Ic: alkynylaryl wherein aryl is optionally substituted with one or more groups selected from the list: halogen, $C_{1-4}$alkyl, $C_{1-4}$alkoxy; or Id: $C_{1-10}$alkyl or $C_{1-6}$alkylaryl, wherein aryl is optionally substituted with one or more groups selected from the list: halogen, $C_{1-4}$alkyl, $C_{1-4}$alkoxy;

may be prepared from compounds of Formula II wherein $R^3$, $R^4$ and Z are as defined for Formula Ia, Ib, Ic or Id, according to Scheme 1 by reaction of II with an appropriate halogenating agent such as a halosuccinimide (NBS, NCS), trichloroisocyanuric acid (TCCA) or bromine in a suitable solvent such as a mixture of dichloromethane and methanol.

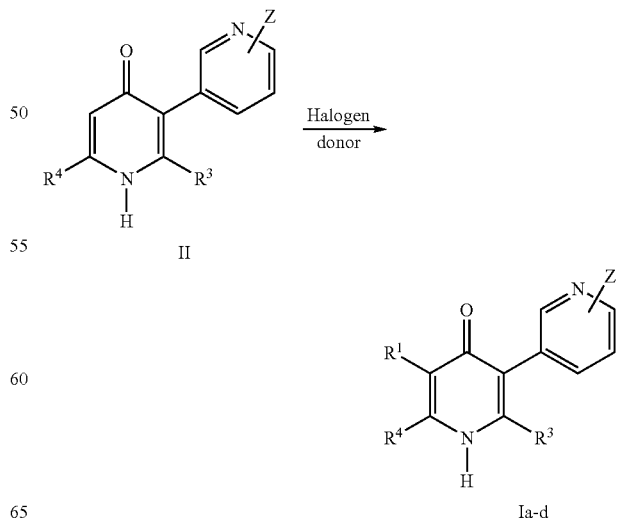

Scheme 1

Compounds of Formula II may be prepared from compounds of Formula III, wherein $R^3$ and $R^4$ are independently $C_{1-6}$alkyl, Z is as defined for Formula Ia, Ib, Ic or Id and $R^x$ is as defined for Formula I above, according to Scheme 2 by treatment of III with aqueous ammonia in a suitable solvent such as ethanol or methanol, suitably with heating under pressure, optionally in the presence of microwave radiation. In one aspect, the reaction is carried out in a steel reactor at elevated temperature for a period of between 1 h and 8 h. In another aspect the reaction is carried out at elevated temperature in a microwave oven, e.g. for a period of 30-90 minutes.

Scheme 2

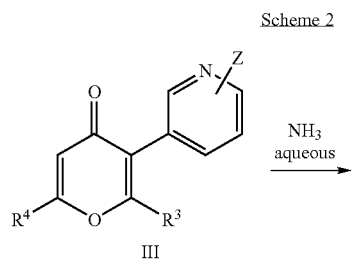

III

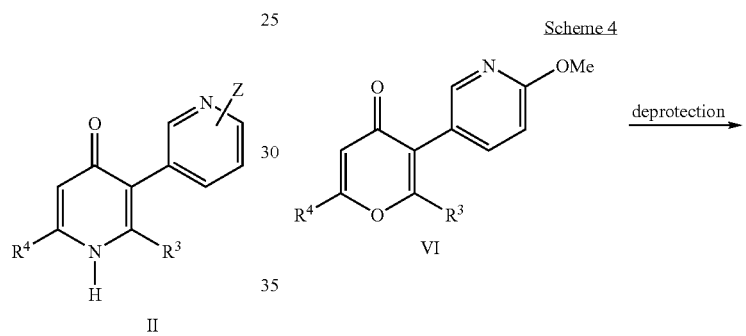

II

Compounds of Formula IIIa, which are compounds of Formula III, wherein $R^3$ and $R^4$ are as defined for Formula Ia, Ib, Ic or Id and Z is OCH$_2$phenyl, optionally substituted with $R^x$, wherein $R^x$ is as defined above for Formula I, may be prepared from compounds of Formula IV, wherein $R^3$ and $R^4$ are independently $C_{1-6}$alkyl, by treatment with halogen$C_{1-6}$phenyl compounds of Formula V, wherein $R^x$ is as defined above, for Formula I, which are commercially available (ALDRICH), according to Scheme 3. A compound of Formula IV is reacted with V in the presence of a suitable base such as silver carbonate or caesium carbonate in a suitable solvent such as toluene at elevated temperature, for example at 70° C.-110° C.

Scheme 3

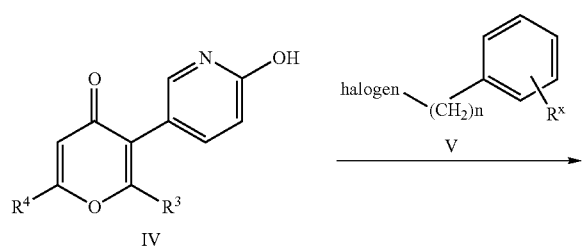

IV

Compounds of Formula IV may be prepared by deprotection of compounds of Formula VI, wherein $R^3$ and $R^4$ are independently $C_{1-6}$alkyl, according to Scheme 4 under standard conditions, for example treatment of IV with 6N hydrochloric acid at elevated temperature, for example between 90° C. and 120° C.

Scheme 4

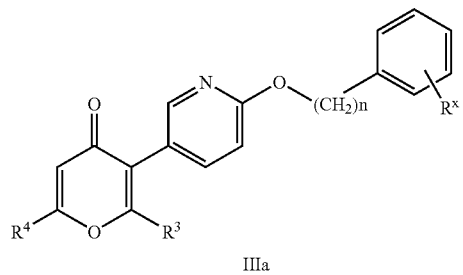

The compound of Formula VIa, which is a compound of Formula VI wherein $R^3$ and $R^4$ are methyl, may be prepared from the compound of Formula VII according to Scheme 5 by condensation of VII, with acetic anhydride (Ac$_2$O) in the presence of an appropriate acidic condensing agent such as polyphosphoric acid at elevated temperature. Other compounds of Formula VI may be prepared in an analogous fashion.

Scheme 5

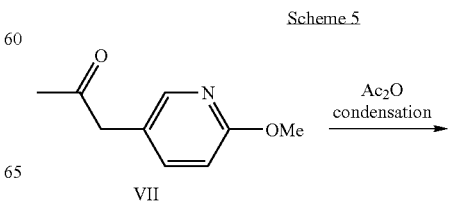

VII

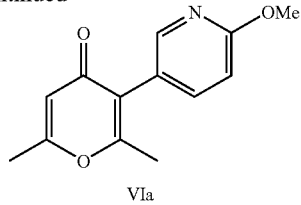

VIa

The compound of Formula VII may be prepared from the compound of Formula VIII according to Scheme 6 by treatment of VIII with iron powder in refluxing acetic acid.

Scheme 6

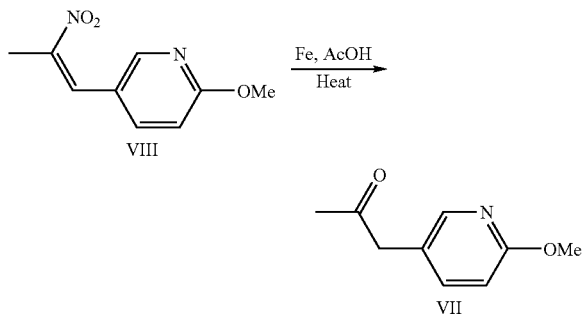

The compound of Formula VIII may be prepared from the compound of Formula IX, which is 5-formyl-2-methoxypyridine which is commercially available (ALDRICH), according to Scheme 7 by reaction of IX with a base, for example a primary alkyl amine in a suitable solvent such as toluene, at a suitable temperature e.g. between 90° C. and reflux temperature; where the base is an amine, an intermediate imine may be formed. The mixture can subsequently be treated with nitroethane (EtNO$_2$) without isolation of any intermediate, in acetic acid at elevated temperature.

Scheme 7

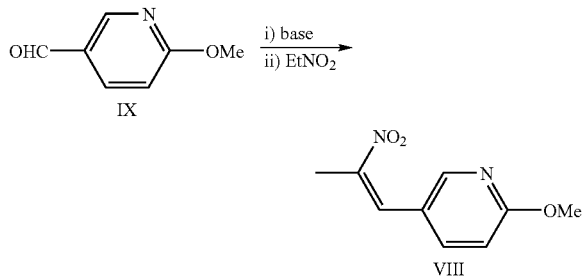

Alternatively, the compound of Formula VII may be prepared from 5-bromo-2-methoxypyridine compound X which is commercially available (ALDRICH), according to Scheme 8 by heating X with isopropenyl acetate and tributyltin methoxide in a suitable solvent such as toluene in the presence of a palladium catalyst and a suitable ligand, to give VII in one step, for example according to the literature procedure given in Nair V, Turner G. A., Buenger G. S., Chamberlain S. D., (1988) J. Org. Chem. 53, 3051. In one aspect, the catalytic system is palladium acetate in the presence of a suitable ligand such as tri-o-tolylphosphine.

Scheme 8

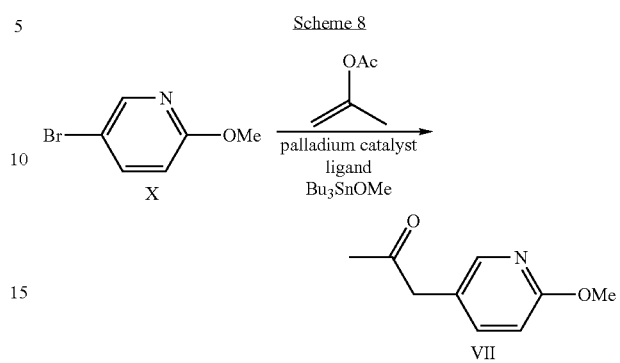

Compounds of Formula IIIb, which are compounds of Formula III wherein $R^3$ and $R^4$ are independently $C_{1-6}$alkyl and Z is phenyl or methylenedioxyphenyl, either of which is optionally substituted with $R^x$, wherein $R^x$ is as defined above for Formula I, may be prepared from the Suzuki coupling reaction between compounds of Formula XI, wherein $R^3$ and $R^4$ are independently $C_{1-6}$alkyl, and boronic acid compounds of Formula XIIa wherein $R^x$ is as defined above for Formula I, according to Scheme 9 (Z is depicted as phenyl substituted with $R^x$ in the Scheme). Compounds of Formula XI may be heated with XIIa in an appropriate solvent such as mixtures of toluene and ethanol in the presence of a suitable base such as sodium hydrogencarbonate and a palladium catalyst, for example according to the literature procedure in Mouaddib A., Joseph B., Hasuaoni A., and Merours J. Y., (2000) Synth. 4, 549. In one aspect, the palladium catalysts are selecte from tetrakis (triphenylphosphine)palladium(0) and dichlorobis(triphenylphosphine) palladium(II).

Scheme 9

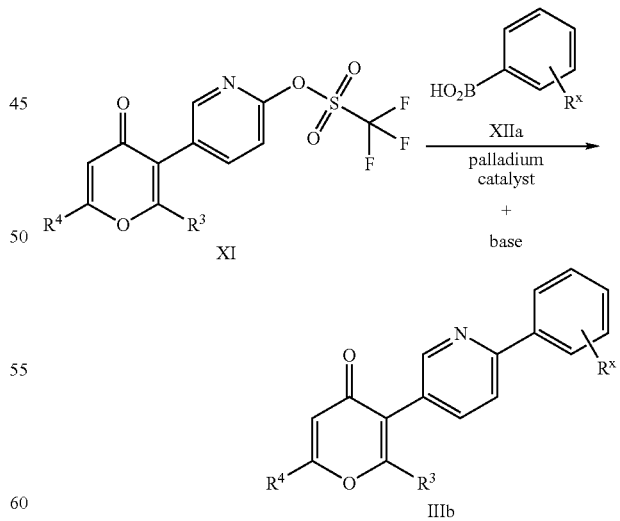

It will be readily apparent to a person skilled in the art that the Suzuki reaction in Scheme 9 may be carried out between compounds of Formula XI and a boronic acid of Formula XIIb, wherein $R^y$ is a substituent which is suitable for later functional group interconversion to $R^x$.

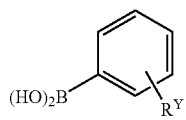
XIIb

The product of the Suzuki reaction may then be subjected to conversion of substituent $R^Y$ into substituent $R^X$, to obtain other compounds of Formula IIIb. For example, the Suzuki reaction may be carried out between XI and XIIb, wherein $R^Y$ is OCH$_2$Ph, followed by removal of the CH$_2$Ph group of $R^Y$, for example using hydrogenation under standard conditions, e.g. in the presence of palladium on charcoal catalyst and hydrochloric acid and subsequent alkylation of the hydroxy group thus formed, for example with ICH$_2$CF$_3$ in the presence of caesium carbonate at elevated temperature, to provide a compound of Formula IIIb.

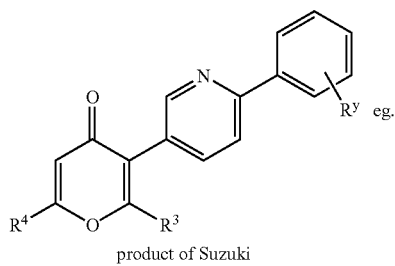
product of Suzuki

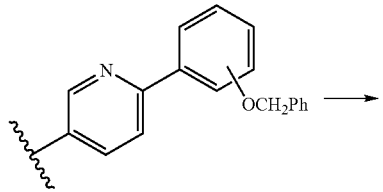

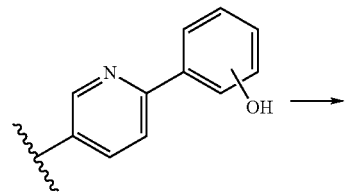

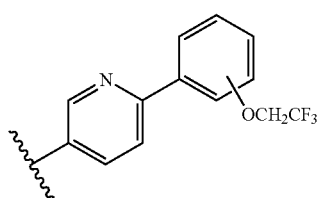

Compounds of Formula XI may be prepared from compounds of Formula IV, wherein $R^3$ and $R^4$ are independently $C_{1-6}$alkyl, according to Scheme 10 by treatment of IV with a mild trifluoromethanesulfonylating agent in a suitable solvent such as dimethylformamide in the presence of a suitable base such as sodium carbonate. In one aspect, the trifluoromethanesulphonylating agent is N-phenyl-trifluoromethanesulfonimide.

Scheme 10

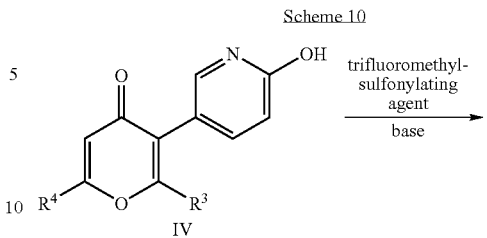

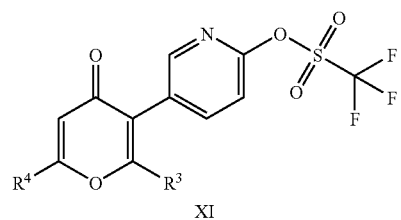

Compounds of Formula IIIc, which are compounds of Formula III wherein $R^3$ and $R^4$ are independently $C_{1-6}$alkyl and Z is alkynylaryl wherein aryl is optionally substituted with one or more groups selected from the list: halogen, $C_{1-4}$alkyl, $C_{1-4}$alkoxy, may be prepared from the Sonogashira coupling reaction between compounds of Formula XI, wherein $R^3$ and $R^4$ are independently $C_{1-6}$alkyl, and terminal alkyne compounds XIII, according to Scheme 11. The compounds of Formula XI may be heated, for example at a temperature between 20° C. below reflux and reflux temperature, with XIII in an appropriate solvent such as mixtures of dimethylformamide and triethylamine, in the presence of a catalyst, such as a mixture of mixture of copper(I) iodide and a suitable palladium catalyst, for example according to the literature procedure in Tilley J. W. and Zawoiski S., (1998) J. Org. Chem. 53, 386. In one aspect, the palladium catalyst is dichlorobis(triphenylphosphine)palladium(II).

Scheme 11

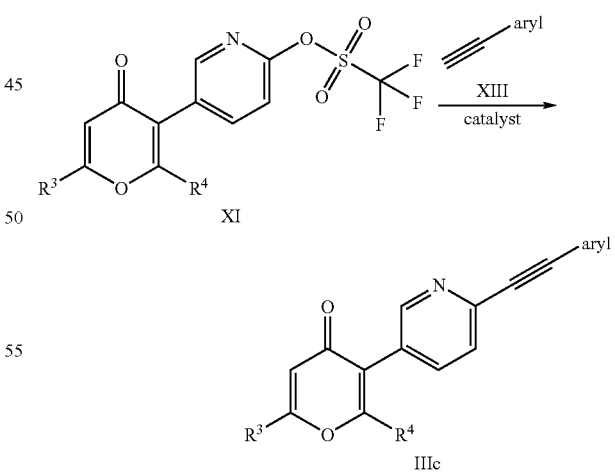

Compounds of Formula IIId(i), which are compounds of Formula III wherein $R^3$ and $R^4$ are independently $C_{1-6}$alkyl and Z is CH$_2$CH$_2$aryl wherein aryl is optionally substituted with one or more groups selected from the list: halogen, $C_{1-4}$alkyl, $C_{1-4}$alkoxy, may be prepared by the hydrogenation of compounds of Formula IIIc with hydrogen gas under pressure in the presence of a suitable catalyst e.g. a palladium catalyst, according to Scheme 12. Suitable hydrogenation catalysts include palladium on activated charcoal. Other compounds of Formula IIId, which are compounds of Formula III wherein $R^3$ and $R^4$ are independently $C_{1-6}$alkyl and Z is $C_{2-10}$alkyl or $C_{3-6}$alkylaryl wherein aryl is optionally substituted with one or more groups selected from the list: halogen, $C_{1-4}$alkyl, $C_{1-4}$alkoxy, may be prepared in an analogous fashion by hydrogenation of the corresponding analogous alkynyl precursor compound.

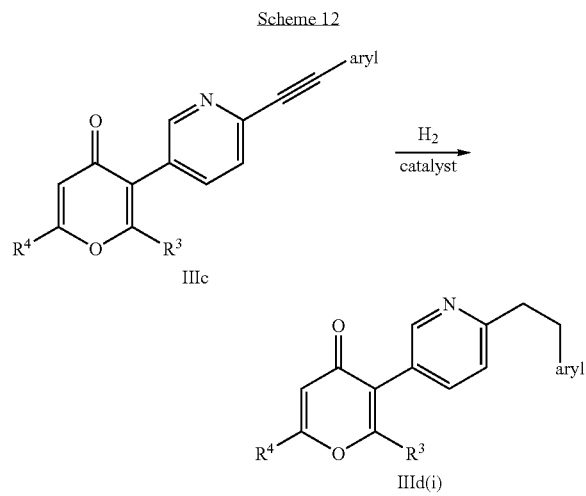

Alternatively, compounds of Formula IId(i), which are compounds of Formula II wherein $R^3$ and $R^4$ are independently $C_{1-6}$alkyl and Z is $CH_2CH_2$aryl wherein aryl is optionally substituted with one or more groups selected from the list: halogen, $C_{1-4}$alkyl, $C_{1-4}$alkoxy, may be prepared by the hydrogenation of compounds of Formula IIc, which are compounds of Formula II wherein $R^3$ and $R^4$ are independently $C_{1-6}$alkyl and Z is alkynylaryl, wherein aryl is optionally substituted with one or more groups selected from the list: halogen, $C_{1-4}$alkyl, $C_{1-4}$alkoxy, with hydrogen gas under pressure in the presence of a suitable catalyst e.g. a palladium catalyst, according to Scheme 13. Suitable hydrogenation catalysts include palladium on activated charcoal. Other compounds of Formula IId wherein Z is $C_{2-10}$alkyl or $C_{3-6}$alkylaryl wherein aryl is optionally substituted with one or more groups selected from the list: halogen, $C_{1-4}$alkyl, $C_{1-4}$alkoxy, may be prepared in an analogous fashion from the corresponding precursor compound.

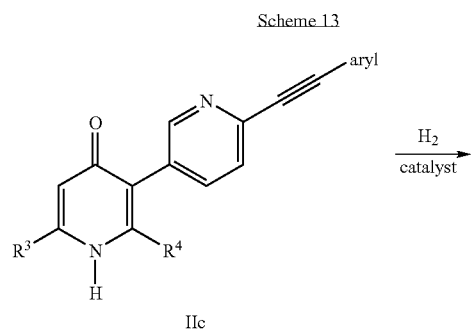

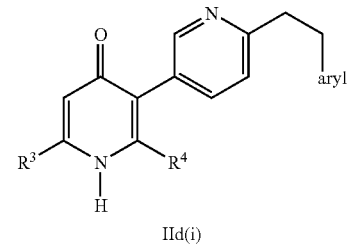

Compounds of Formula Ie, which are compounds of Formula I wherein $R^1$ is halogen, $R^2$ is hydrogen, $R^3$ and $R^4$ are $C_{1-6}$alkyl, Het is pyridyl substituted with group Z, wherein Z is —Oaryl, (for example phenoxy), optionally substituted with $R^X$ as defined for Formula I above, may be prepared by the Suzuki coupling reaction between compounds of Formula XIV, wherein $R^1$, $R^3$ and $R^4$ are independently $C_{1-6}$alkyl, and boronic acid compounds of Formula XV, wherein Z is —Oaryl, (for example phenoxy as shown in Scheme 14), and $R^X$ is as defined for Formula I above, according to Scheme 14. For example, the literature method given in Mouaddib A., Joseph B., Hasuaoni A., Merours J. Y., (2000) Synth. 4, 549, can be used. The reaction is carried out in a suitable solvent and suitable conditions, such as dry dimethylformamide at a temperature between 100° C. and 160° C. under microwave radiation, in the presence of a suitable palladium catalyst such as palladium acetate and a base such as potassium carbonate. Other compounds of Formula Ie may be prepared in an analogous fashion from the corresponding analogous precursor compound.

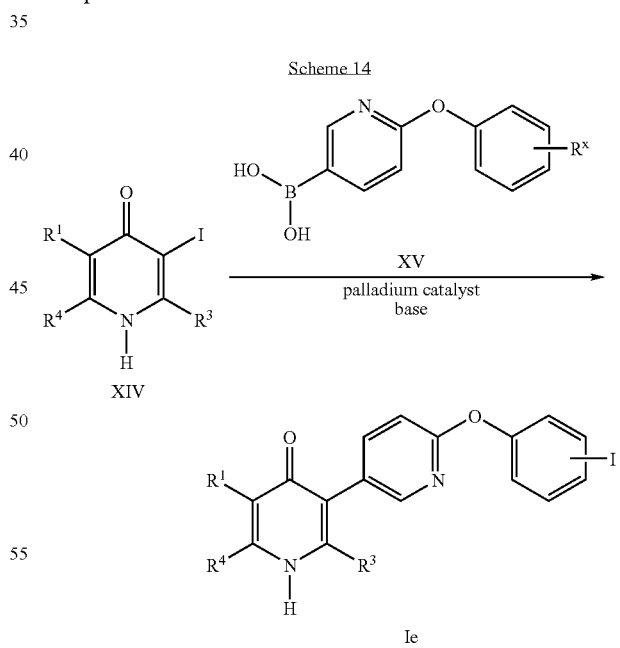

Boronic acid compounds of Formula XV may be obtained from compounds of Formula XVI wherein $R^X$ is as defined for Formula I above, according to Scheme 15. Compounds of Formula XVI may be treated with an organometallic compound such as n-BuLi at a temperature between −60° C. and −78° C. in the presence of tri-isopropylborate in a suitable solvent such as THF.

Scheme 15

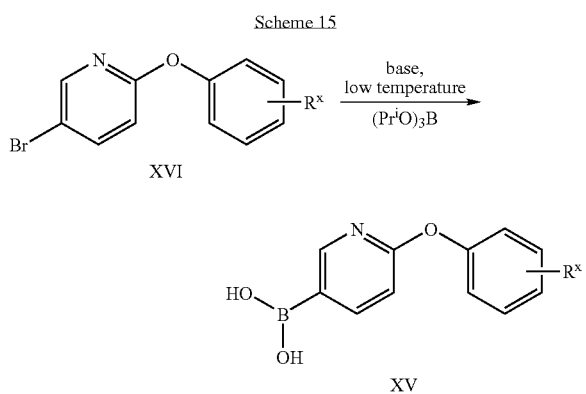

Compounds of Formula XVI may be prepared by reaction of 2,5-dibromopyridine compound XVII which is commercially available (ALDRICH), with phenol compounds of Formula XVIII, wherein $R^X$ is as defined above for Formula I above, according to Scheme 16. The reaction is carried out in the presence of a base such as sodium hydride, in a suitable solvent such as dry N,N-dimethylformamide at a suitable temperature, e.g. between 40° C. and 80° C.

Scheme 16

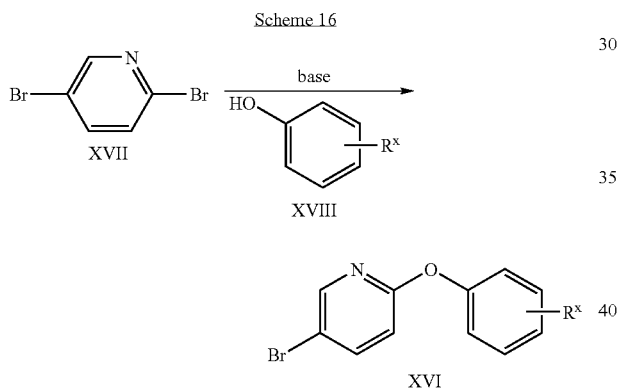

Compounds of Formula XIVa, which are compounds of Formula XIV wherein $R^1$ is Cl, may be prepared from compounds of Formula XIX, wherein $R^3$ and $R^4$ are independently $C_{1-6}$alkyl, according to Scheme 1 by reaction of XIX with iodine in the presence of a suitable base such as sodium hydroxide in a suitable solvent such as water. Other compounds of Formula XIV may be prepared in an analogous fashion from the corresponding analogous precursor compound Scheme 17

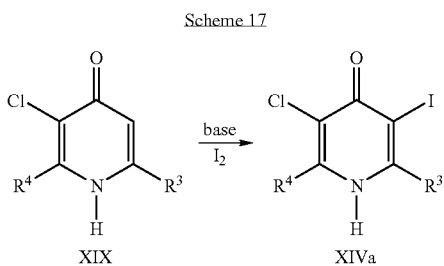

Compounds of Formula XIX may be prepared from compounds of Formula XX, wherein $R^3$ and $R^4$ are independently $C_{1-6}$alkyl, according to Scheme 18 by treatment of XX with N-chlorosuccinimide (NCS) in a suitable solvent such as a mixture of methanol and dichloromethane.

Scheme 18

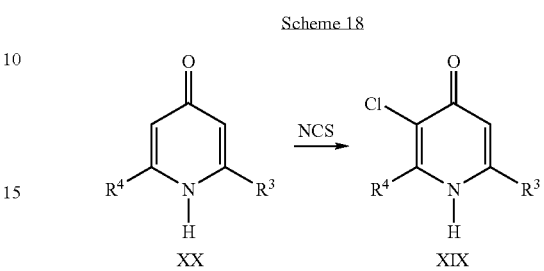

Compounds of Formula XXa, which are compounds of Formula XX wherein $R^3$ and $R^4$ are methyl, may be prepared from 2,6-dimethyl-pyran-4-one compound XXI, which is commercially available (ALDRICH) according to Scheme 19 by treatment of XXI with aqueous ammonia in a suitable solvent at a suitable temperature such as ethanol at between 120° C. and 140° C. Other compounds of Formula XX may be prepared in an analogous fashion from the corresponding analogous precursor compound.

Scheme 19

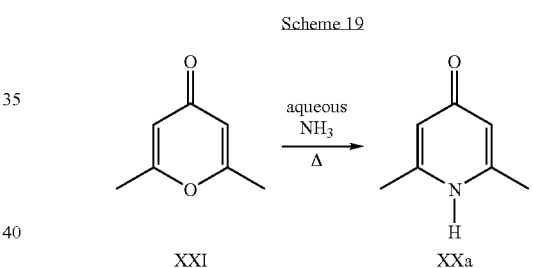

Compounds of Formula If and Ig which are compounds of Formula I wherein $R^1$ is halogen, $R^2$ is hydrogen, $R^3$ and $R^4$ are independently $C_{1-6}$alkyl, Het is pyrimidyl substituted with group Z, wherein Z is If: $C_{1-10}$alkyl;

Ig: phenyl, optionally substituted with $R^X$, wherein $R^X$ is chloro, fluoro, cyano, —$NR^AR^B$, $C_{1-6}$alkyl, $C_{1-6}$alkoxy or $C_{1-6}$alkylS(O)$_m$—; and $R^A$, $R^B$ and m are as defined for Formula I above;

may be prepared from the reaction between compounds of Formula XIV wherein $R^1$, $R^3$ and $R^4$ are as defined for Formula If or Ig, and tributyltin compounds of Formula XXII, wherein Z is as defined above for Formula If or Ig, under Stille reaction conditions, according to Scheme 20, for example according to the literature method given in Roth G. P., Farina V., (1995), Tet. Lett. 36 (13), 2191-2194. In one aspect, the reaction is carried out in the presence of copper(I) iodide and a suitable catalytic system. In one aspect, the catalytic systems include tris(dibenzylideneacetone)dipalladium(0) in the presence of a suitable ligand such as tri(2-furyl)phosphine in N-methylpyrrolidinone as solvent.

Scheme 20

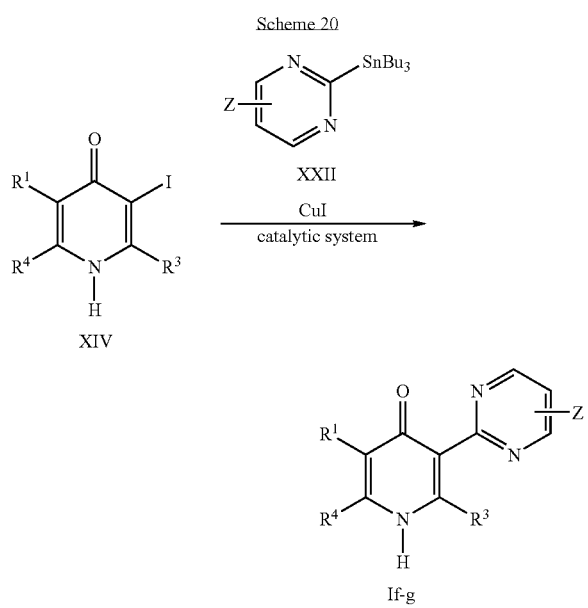

If-g

Tributyltin compounds of Formula XXIIf, which are compounds of Formula XXII wherein Z and $R^X$ are as defined above for Formula If, may be prepared from 2-chloropyrimidine compounds of Formula XXIII according to Scheme 21, by treatment of XXIII with a suitable base such as lithium diisopropylamide followed by reaction of the salt generated in situ with tributyltin hydride in a suitable solvent such as dry THF.

Scheme 21

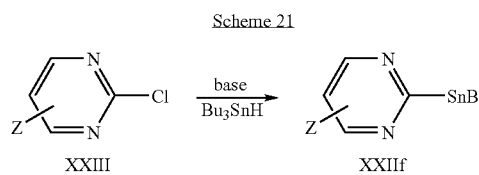

Tributyltin compounds of Formula XXIIIg, which are compounds of Formula XXII wherein Z is as defined above for Formula Ig, may be prepared from compounds of Formula XXIV, wherein $R^X$ is as defined above for Formula Ig, according to Scheme 22, by treatment of XXIV with a suitable base such as n-BuLi followed by tributyltin chloride in a suitable solvent such as THF at a suitable temperature, such as between −60° C. and −78° C.

Scheme 22

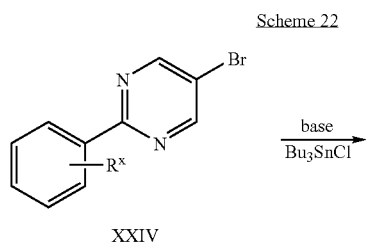

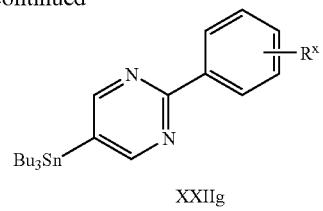

XXIIg

Compounds of Formula XXIV may be prepared from compounds the Suzuki coupling reaction between boronic acid compounds of Formula XII and 5-bromo-2-iodo-pyrimidine compound XXV, which is commercially available (ALDRICH), according to Scheme 23. The compound of Formula XXV may be heated with XII and subjected to microwave radiation in the presence of a suitable base such as sodium carbonate and a suitable palladium catalyst such as dichlorobis(triphenylphosphine)palladium(II), in an appropriate solvent such as acetonitrile at a suitable temperature, e.g. 100° C.-170° C.

Scheme 23

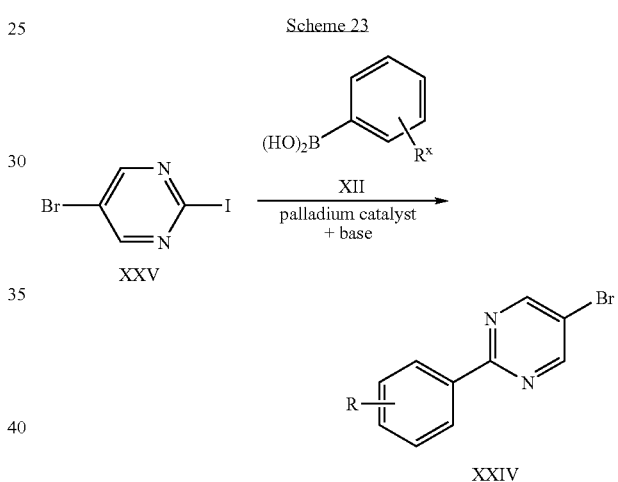

Compounds of Formula I wherein $R^1$ is halogen, $R^2$ is hydrogen, $R^3$ and $R^4$ are independently $C_{1-6}$alkyl, and Het represents a 6-membered monocyclic heteroaromatic ring containing at least one nitrogen atom other than pyridyl and pyrimidyl, and is optionally substituted with group Z, wherein Z is If: $C_{1-10}$alkyl;
Ig: phenyl, optionally substituted with $R^X$, wherein $R^X$ is chloro, fluoro, cyano, —$NR^A R^B$, $C_{1-6}$alkyl, $C_{1-6}$alkoxy or $C_{1-6}$alkylS(O)$_m$—; and $R^A$, $R^B$ and m are as defined for Formula I above;

may be prepared in an analogous fashion from the corresponding analogous precursor compound which is Bu$_3$Sn-Het-Z.

Alternatively, compounds of Formula Id(i), which are compounds of Formula I wherein $R^1$ is halogen, $R^3$ and $R^4$ are independently $C_{1-6}$alkyl and Z is CH$_2$CH$_2$aryl wherein aryl is optionally substituted with one or more groups selected from the list: halogen, $C_{1-4}$alkyl, $C_{1-4}$alkoxy, may be prepared by the hydrogenation of compounds of Formula Ic with hydrogen gas under pressure in the presence of a suitable catalyst e.g. a palladium catalyst, according to Scheme 24. Suitable hydrogenation catalysts include palladium on activated charcoal. Other compounds of Formula Id wherein Z is $C_{2-10}$alkyl or $C_{3-6}$alkylaryl wherein aryl is optionally substituted with one or more groups selected from the list: halogen, $C_{1-4}$alkyl, $C_{1-4}$alkoxy, may be prepared in an analogous fashion from the corresponding analogous precursor compound.

Scheme 24

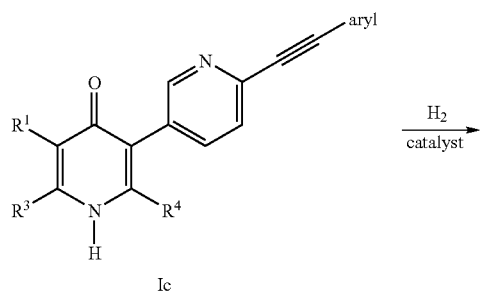

Ic

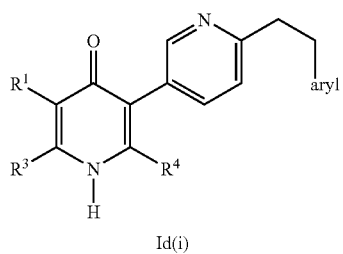

Id(i)

Alternatively, compounds of Formula Ic(i), which are compounds of Formula Ic wherein $R^1$ is chlorine may be prepared from the Sonogashira coupling reaction between compounds of Formula XXVI, wherein $R^3$ and $R^4$ are independently $C_{1-6}$alkyl, and commercially available arylethynyl compounds of Formula XIII, according to Scheme 25. Compounds of Formula XXVI and XXIII may be reacted in the presence of a catalyst mixture such as a mixture of copper(I) iodide and a suitable palladium catalyst system, for example a suitable palladium catalyst and a ligand, in a suitable solvent, such as a mixture of N,N-dimethylformamide and triethylamine, under elevated temperature such as between 20° C. below reflux and reflux, for example according to the literature procedure in Tilley J. W. and Zawoiski S., (1998) J. Org. Chem. 53, 386. In one aspect, the catalytic systems include dichloro-bis(triphenylphosphine)palladium(II) in the presence of triphenylphosphine as ligand.

Scheme 25

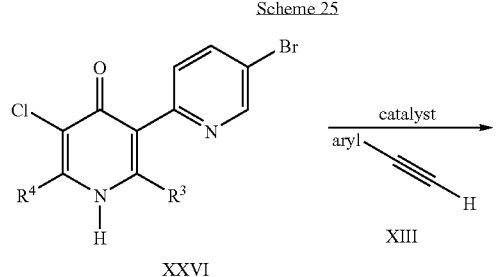

XXVI

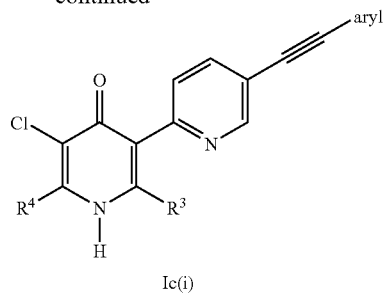

Ic(i)

Compounds of Formula XXVI may be prepared from compounds of Formula XXVI, wherein $R^3$ and $R^4$ are independently $C_{1-6}$alkyl, according to Scheme 26, by a chlorination reaction of XXVI using a suitable chlorinating reagent such trichloroisocyanuric acid (TCCA) and N-chlorosuccinimde (NCS), in a suitable solvent such as a mixture of dichloromethane and methanol.

Scheme 26

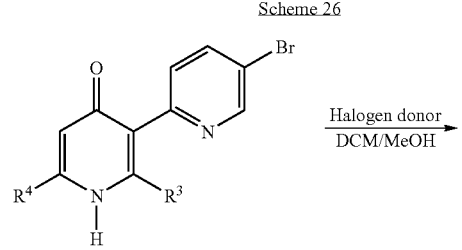

XXVII

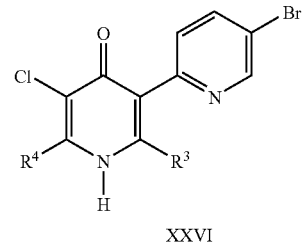

XXVI

Compounds of Formula XXVII may be prepared from compounds of Formula XXVIII, wherein $R^3$ and $R^4$ are independently $C_{1-6}$alkyl, according to Scheme 27 by treatment of III with aqueous ammonia in a suitable solvent such as ethanol, at elevated temperature under pressure. In one aspect, the reaction is carried out in a steel reactor at elevated temperature (about 120° C.-140° C.) for a period of between 1 h and 8 h.

Scheme 27

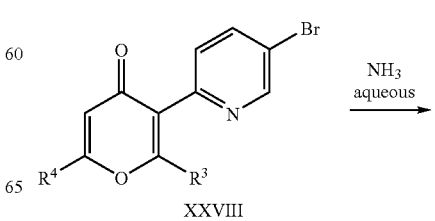

XXVIII

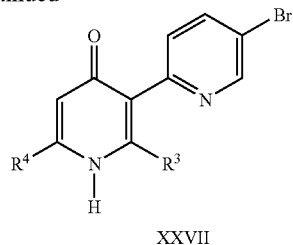

XXVII

Compounds of Formula XXVIIIa, which are compounds of Formula XXVIII in which $R^3$ and $R^4$ are methyl, may be prepared by condensation of compound XXIX with acetic anhydride ($Ac_2O$) according to Scheme 28, in the presence of a suitable condensing agent such as mixtures of phosphorous pentoxide/methanesulfonic acid (Eaton's reagent) at elevated temperature. Other compounds of Formula XXVIII may be prepared in an analogous fashion.

Scheme 28

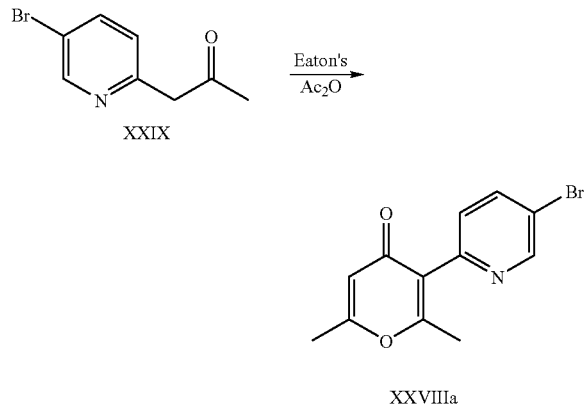

The compound of Formula XXIX may be prepared from the compound of Formula XXX according to Scheme 29, by treatment of XXX with acetic acid in the presence of a catalyst such as iron powder at elevated temperature, such as between 90° C. and 140° C.

Scheme 29

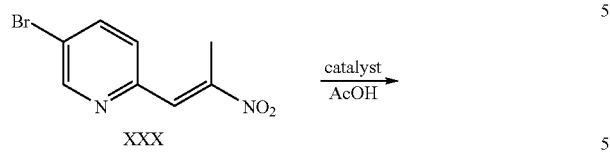

The compound of Formula XXX may be prepared from the compound of Formula XXXI according to Scheme 30, by a reaction of XXXI with a base, for example a primary alkyl amine in a suitable solvent such as toluene at elevated temperature; where the base is an amine, an intermediate imine may be formed. The mixture can subsequently be treated with nitroethane without isolation of any intermediate, in acetic acid at elevated temperature such as 80° C.-120° C.

Scheme 30

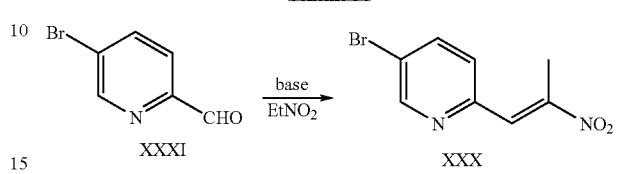

The compound of Formula XXXI may be prepared from 2,5-dibromopyridine compound XXXII which is commercially available (ALDRICH), according to Scheme 31, by in situ generation of a suitable salt of XXXII using a suitable base such as the generation of a lithium salt using n-BuLi, followed by treatment with DMF in a suitable solvent such as toluene at a temperature between −60° C. and −78° C.

Scheme 31

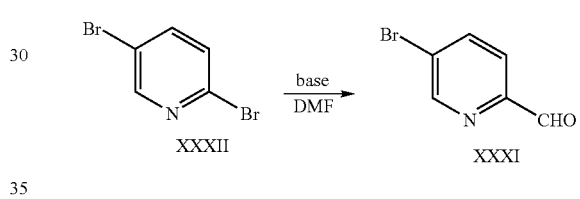

Compounds of Formula IIIe, which are compounds of Formula III wherein $R^3$ and $R^4$ are independently $C_{1-6}$alkyl and Z is $C_{2-6}$alkenylaryl wherein aryl is optionally substituted with one or more groups selected from the list: halogen, $C_{1-4}$alkyl, $OC_{1-4}$alkyl, may be prepared from the Heck coupling reaction between compounds of Formula XI, wherein $R^3$ and $R^4$ are independently $C_{1-6}$alkyl, and alkenylaryl compounds XXXIII, according to Scheme 32. The compounds of Formula XI heated with XXXIII, for example at a temperature between 20° C. below reflux and reflux temperature, in the presence of a base such as triethylamine, a suitable palladium catalyst such as palladium acetate and a suitable ligand such as TOTP tri(o-tolylphosphine) in a suitable solvent such as acetonitrile, for example according to the literature procedure in Crisp G. T., Papadopoulos S., (1989) Australian J. Chem. 42 (2), 279-285.

Scheme 32

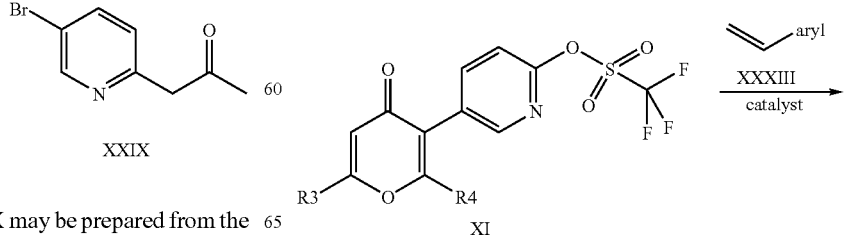

-continued

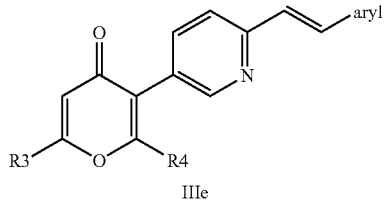

IIIe

Compounds of Formula Ih, which are compounds of Formula I wherein $R^1$ is cyano, $R^2$ is hydrogen, $R^3$ and $R^4$ are independently $C_{1-6}$alkyl, Het is as defined above for Formula I and is optionally substituted with Z, wherein Z does not contain an iodoaryl substituent, may be prepared from compounds of Formula Ij which are compounds of Formula I wherein $R^1$ is iodo, and $R^2$, $R^3$, $R^4$ and Het are as defined for Formula Ih, according to Scheme 33, by heating Ij using, for example, microwave radiation, with a suitable iodo salt such as copper iodide in the presence of a suitable cyanide salt such as sodium cyanide and a phase transfer catalyst such as tetrabutylammonium bromide (TBAB), for example according to the literature procedure in Arvela R. K., Leadbeater N. E., Torenius H. M., Tye H., (2003) Org. Biom. Chem. 1 (7), 1119.

Scheme 33

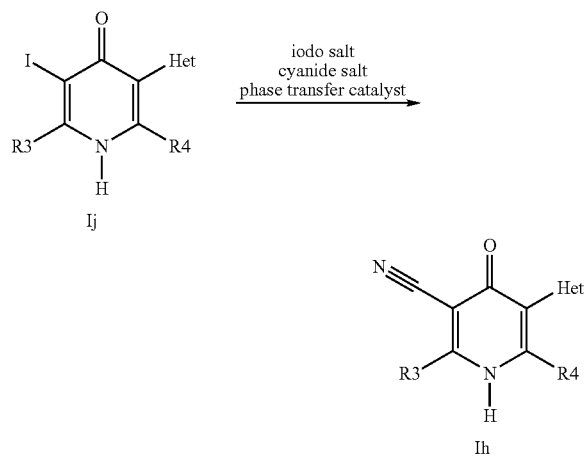

Compounds of Formula Ij may be prepared from compounds of Formula XXXIV by iodination of XXXIV using a suitable iodinating agent, such as N-iodosuccinimide (NIS), in a suitable solvent, such as acetic acid (AcOH), according to Scheme 34.

Scheme 34

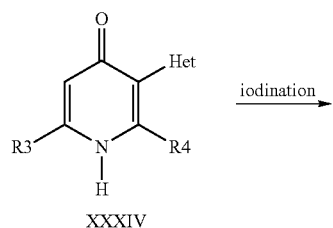

XXXIV

-continued

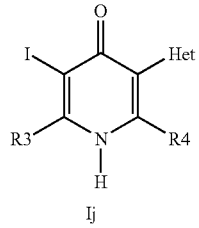

Ij

Alternatively, compounds of Formula Ij may be prepared in an analogous fashion to compounds of Formula If-g Compounds of Formula XXXIV may be prepared in an analogous fashion to compounds of Formula II described above.

It will be readily apparent to those skilled in the art that the preparation of compounds of Formula I wherein $R^1$ is hydrogen may be carried out in an analogous fashion to the preparation of compounds of Formula I wherein $R^1$ is halogen as described hereinabove, but wherein the halogenation step to introduce the halogen group at $R^1$ is omitted.

Compounds of Formula I wherein $R^2$ is hydroxyl may be prepared by oxidation of compounds of Formula I wherein $R^2$ is hydrogen using a suitable oxidising agent such as hydrogen peroxide in the presence of acetic acid, or meta-chloroperbenzoic acid (mCPBA) in dichloromethane. Alternatively, compounds of Formula I wherein $R^2$ is hydroxyl may be prepared according to procedures which are analogous to those previously reported in PCT Patent Application No. WO 91/13873 A1 (see page 19, step (A)).

Compounds of Formula I wherein $R^2$ is other than hydrogen or hydroxyl may also be prepared according to procedures which are analogous to those previously reported in PCT Patent Application No. WO 91/13873 A1 (see page 19, step (A)).

It will be readily apparent to those skilled in the art that further compounds of Formula I may be prepared using methods analogous to those outlined above, or by reference to the experimental procedures detailed in the Examples provided herein, or by using methods analagous to those previously reported in PCT Patent Application No. WO 91/13873 A1.

Acid salts of compounds of Formula I may be prepared from treatment of the compounds with an acid in a suitable solvent under standard conditions. For example, to make the hydrochloride salts of compounds of Formula I, the compounds may be treated with an excess of hydrochloric acid in a suitable solvent such as methanol or water, or a mixture thereof.

Those skilled in the art will appreciate that in the preparation of the compound of Formula I or a pharmaceutically acceptable derivative thereof, it may be necessary and/or desirable to protect one or more sensitive groups in the molecule or the appropriate intermediate to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl or aralkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate.

EXAMPLES

The following examples illustrate the invention. These examples are not intended to limit the scope of the invention, but rather to provide guidance to the skilled artisan to prepare and use the compounds, compositions, and methods of the invention. While particular embodiments of the invention are described, the skilled artisan will appreciate that various changes and modifications can be made without departing from the spirit and scope of the invention.

Experimental Section

Intermediate 1

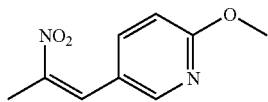

2-Methoxy-5-[(2-nitroprop-1-en-1-yl]pyridine

A solution of 5-formyl-2-methoxypyridine (ALDRICH, 14.56 g) and butylamine (23.1 ml) in dry toluene (90 ml) was heated to reflux in a flask equipped with a Dean-Stark trap in order to remove water. After 2.5 h of heating the mixture was concentrated to dryness and the residue dissolved in acetic acid (45 ml). To the solution was added nitroethane (11.4 ml) and the mixture was heated to 100° C. After 2.5 h of heating the mixture was cooled to room temperature and poured onto 400 ml of a mixture ice/water with vigorous stirring. The mixture was extracted with ethyl acetate (400 ml) and the organic layer washed successively with water (2×300 ml), 10% NaHCO$_3$ (2×300 ml), water (300 ml) and brine (300 ml), then dried over MgSO$_4$. Elimination of the solvent under vacuum gave a yellow powder which was purified by column chromatography on silica gel, eluting with mixtures hexane/ethyl acetate (v/v 20:1 and 10:1) to afford 16.65 g of the title compound as a yellow powder.

$^1$H-NMR (δ, ppm, CDCl$_3$): 8.30 (m, 1H); 8.02 (bs, 1 h) 7.68 (dd, 1H); 6.83 (d, 1H); 3.99 (s, 3H); 2.47 (s, 3H)

Intermediate 2

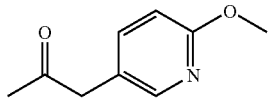

1-(6-Methoxypyridin-3-yl)acetone

Method A:

In a 1 L round bottom flask equipped with mechanical stirring were placed iron powder (55 g) and acetic acid (220 ml). To this suspension was added dropwise a solution of Intermediate 1 (16.65 g) in acetic acid (120 ml). The mixture was heated to reflux with vigorous stirring under nitrogen, then diluted with acetic acid (80 ml). After 2 h of heating the mixture was cooled to room temperature and water (750 ml) was added. The mixture was extracted with dichloromethane (3×300 ml) and the combined organic layers washed with water (400 ml), saturated NaHCO$_3$ (400 ml), water (400 ml) and brine (400 ml), then dried over MgSO$_4$. Elimination of the solvent to dryness gave the title compound (12.49 g) as a pale brown oil which was used for the next step without further purification.

Method B

In a 1 L jacketed vessel were placed 5-bromo-2-methoxypyridine (ALDRICH, 16 ml) and dry toluene (625 ml). The resulting solution was deoxygenated by bubbling argon for 20 min. Tri-o-tolylphosphine (2.99 g), palladium acetate (1.65 g), isopropenyl acetate (20.3 ml) and tributyltin methoxide (49.6 ml) were added successively under argon atmosphere and the mixture heated to 80° C. After 2.5 h the mixture was cooled to room temperature and filtered. The filtrate was concentrated to dryness under vacuum and treated with acetonitrile (800 ml). The solid precipitated was removed by filtration and the filtrate washed with hexane (3×800 ml). The acetonitrile solution was dried over Na$_2$SO$_4$ and concentrated to dryness. The residue was purified by column chromatography on silica gel, eluting with mixtures hexane/ethyl acetate (v/v 9:1 and 2:1). 13.78 g of the title compound were obtained as a yellow oil.

$^1$H-NMR (δ, ppm, CDCl$_3$): 7.97 (bd, 1H); 7.41 (dd, 1H); 6.73 (d, 1H); 3.92 (s, 3H); 3.63 (s, 2H); 2.19 (s, 3H)

Intermediate 3

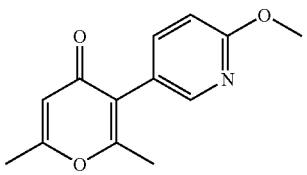

3-(6-Methoxypyridin-3-yl)-2,6-dimethyl-4H-pyran-4-one

In a 1 L round bottom flask equipped with mechanical stirring were placed polyphosphoric acid (117 g) and acetic anhydride (55 ml) and the thick mixture heated to 95° C. To this mixture was added dropwise a solution of Intermediate 2 (17.26 g) in acetic anhydride (75 ml). The dark mixture was heated at 95° C. under inert atmosphere for 1.5 h. The mixture was cooled to room temperature and water (700 ml) was added carefully (exotherm). The suspension obtained was taken-out the flask and neutralized at 0° C. (ice/water bath) by adding solid NaOH and extracted with dichloromethane (3×300 ml). The organic layer was washed successively with 10% Na$_2$CO$_3$ (500 ml), water (500 ml) and brine (500 ml), dried over MgSO$_4$ and concentrated to dryness. The dark brown oily residue was purified by column chromatography on silica gel, eluting with mixtures hexane/acetone (v/v 5:1 and 4:1). 15 g of the title compound were obtained as a orange powder.

$^1$H-NMR (δ, ppm, CDCl$_3$): 8.01 (bd, 1H); 7.51 (dd, 1H); 6.81 (d, 1H); 6.19 (s, 1H); 3.95 (s, 3H); 2.29 (s, 3H); 2.23 (s, 3H)

Intermediate 4

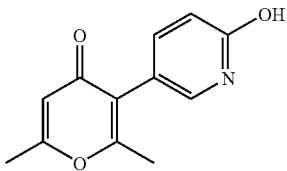

3-(6-Hydroxypyridin-3-yl)-2,6-dimethyl-4H-pyran-4-one

A solution of Intermediate 3 (15 g) in 6N hydrochloric acid (330 ml) was heated at 110° C. for 48 h, then cooled to room temperature. The resulting solution was carefully neutralized at 0° C. (ice/water bath) by slow addition of 6N NaOH (300 ml). The aqueous solution was passed through a column of resin DIAION HP20 (250-600µ) [which was previously prepared by passing methanol (1 L) then water (1 L) through it,] it in order to eliminate inorganics and the organics were eluted with methanol. Elimination of the solvent gave a brown powder which was dissolved in a mixture dichloromethane/10% methanol and filtered through a pad of celite. Elimination of the solvent gave 13.4 g of the title compound as a pale brown powder which was used for the next step without further purification.

$^1$H-NMR (δ, ppm, CD$_3$OD): 7.47 (dd, 1H); 7.37 (d, 1H); 6.59 (d, 1H); 6.24 (s, 1H); 2.34 (s, 3H); 2.30 (s, 3H)

Intermediate 5

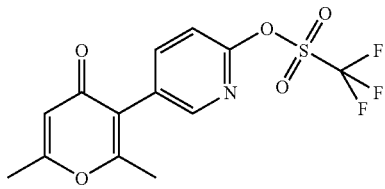

2,6-Dimethyl-3-(6-trifluoromethanesulfonyloxy-pyridin-3-yl)-4H-pyran-4-one

To a suspension of Intermediate 4 (4 g) in dry N,N-dimethylformamide (120 ml) was added powdered potassium carbonate (7.62 g). After stirring at room temperature for 2 minutes, solid N-phenyltrifluoromethanesulfonimide (FLUKA, 6.58 g) was added portionwise. After 1 h of stirring the reaction was incomplete, so additional N-phenyltrifluoromethanesulfonimide (150 mg then 200 mg) and powdered potassium carbonate (250 mg) were added. After 1 h, the suspension was diluted with ethyl acetate (300 ml) and washed with ammonium chloride (3×250 ml). The solvent was removed to dryness under vacuum and the residue dissolved in diethyl ether (200 ml). The ethereal solution was washed with 1N NaOH (4×200 ml) and brine (200 ml), dried over Na$_2$SO$_4$ and concentrated to dryness to afford 5 g of the title compound as a pale yellow powder.

$^1$H-NMR (δ, ppm, CDCl$_3$): 8.24 (d, 1H); 7.86 (dd, 1H); 7.23 (d, 1H); 6.23 (s, 1H); 2.32 (s, 3H); 2.26 (s, 3H)

Intermediate 6

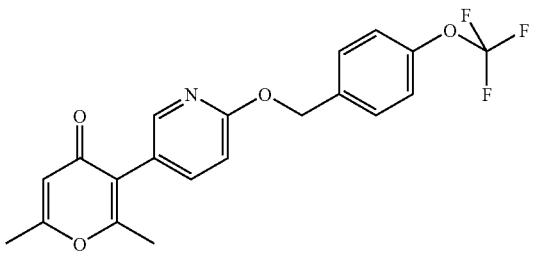

2,6-dimethyl-5-(6-{[4-(trifluoromethoxy)benzyl]oxy}pyridin-3-yl)-4H-pyran-4-one

To a solution of Intermediate 4 (0.326 g) in dry toluene (15 ml) were added consecutively 4-trifluoromethoxybenzyl bromide (ALDRICH, 0.6 ml) and silver carbonate (0.31 g). The mixture was heated at 60° C. in the dark for 30 h, then cooled to room temperature. The remaining solids were separated by filtration and the solid washed with ethyl acetate. The combined organics were washed with 10% NaHCO$_3$ (75 ml) and water (2×50 ml), then dried over Na$_2$SO$_4$. Elimination of the solvent under vacuum gave an oil which was purified by column chromatography on silica gel, eluting with mixtures hexane/ethyl acetate (v/v 2:1 and 1:1), to afford 0.423 g of the title compound as a pale brown powder.

$^1$H-NMR (δ, ppm, DMSO-d$_6$): 8.02 (d, 1H); 7.61-7.58 (m, 3H); 7.38 (bd, 2H); 6.93 (d, 1H); 6.21 (s, 1H); 5.39 (s, 2H); 2.27 (s, 3H); 2.18 (s, 3H)

Intermediates 7-12 were prepared by methods analogous to that described for Intermediate 6, as indicated in Table 1.

TABLE 1

| Int. | R | Starting Intermediate | Chemical name | Physical Data |
|---|---|---|---|---|
| 7 | 3-CF$_3$ | 4 | 2,6-dimethyl-5-(6-{[3-(trifluoromethyl)benzyl]oxy}pyridin-3-yl)-4H-pyran-4-one | $^1$H-NMR (δ, ppm, CDCl$_3$): 8.02 (d, 1H); 7.74 (s, 1H); 7.63 (m, 1H); 7.55-7.45 (m, 3H); 6.90 (d, 1H); 6.20 (s, 1H); 5.45 (s, 2H); 2.29 (s, |

TABLE 1-continued

[Structure: 2,6-dimethyl-5-(6-{[benzyl]oxy}pyridin-3-yl)-4H-pyran-4-one core with R substituent on benzyl ring positions 2-6]

| Int. | R | Starting Intermediate | Chemical name | Physical Data |
|---|---|---|---|---|
| 8 | 4-CF$_3$ | 4 | 2,6-dimethyl-5-(6-{[4-(trifluoromethyl)benzyl]oxy}pyridin-3-yl)-4H-pyran-4-one | $^1$H-NMR (δ, ppm, CDCl$_3$): 8.00 (d, 1H); 7.65-7.53 (m, 5H); 6.89 (d, 1H); 6.20 (s, 1H); 5.46 (s, 2H); 2.29 (s, 3H); 2.24 (s, 3H). |
| 9 | 2-CF$_3$ | 4 | 2,6-dimethyl-5-(6-{[2-(trifluoromethyl)benzyl]oxy}pyridin-3-yl)-4H-pyran-4-one | $^1$H-NMR (δ, ppm, CD$_3$OD): 8.01 (d, 1H); 7.76-7.71 (m, 2H); 7.65-7.58 (m, 2H); 7.52-7.47 (m, 1H); 6.96 (d, 1H); 6.26 (s, 1H); 5.58 (s, 2H); 2.35 (s, 3H); 2.26 (s, 3H). |
| 10 | 3,5-diCF$_3$ | 4 | 2,6-dimethyl-5-(6-{[3,5-bis(trifluoromethyl)benzyl]oxy}pyridin-3-yl)-4H-pyran-4-one | $^1$H-NMR (δ, ppm, CD$_3$OD): 8.07 (bs, 2H); 8.00 (d, 1H); 7.90 (bs, 1H); 7.61 (dd, 1H); 7.00 (d, 1H); 6.26 (s, 1H); 5.57 (s, 2H); 2.35 (s, 3H); 2.25 (s, 3H). |
| 11 | 4-F | 4 | 5-(6-{[4-fluorobenzyl]oxy}pyridin-3-yl)-2,6-dimethyl-4H-pyran-4-one | $^1$H-NMR (δ, ppm, CDCl$_3$): 8.01 (d, 1H); 7.53 (dd, 1H); 7.47-7.41 (m, 2H); 7.10-7.02 (m, 2H); 6.86 (d, 1H); 6.20 (s, 1H); 5.35 (s, 2H); 2.29 (s, 3H); 2.24 (s, 3H). |
| 12 | 3,5-diF | 4 | 5-(6-{[3,5-difluorobenzyl]oxy}pyridin-3-yl)-2,6-dimethyl-4H-pyran-4-one | $^1$H-NMR (δ, ppm, CD$_3$OD): 8.00 (d, 1H); 7.59 (dd, 1H); 7.10-7.03 (m, 2H); 6.97 (d, 1H); 6.90-6.82 (m, 1H); 6.26 (s, 1H); 5.41 (s, 2H); 2.35 (s, 3H); 2.25 (s, 3H). |

Intermediate 13

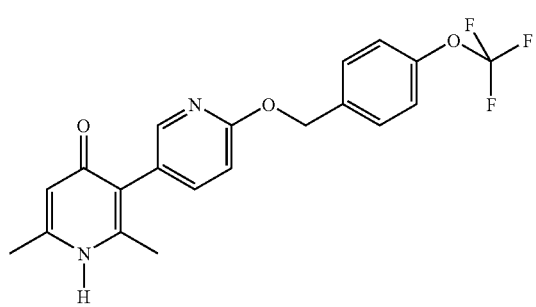

2,6-Dimethyl-6'-{[4-(trifluoromethoxy)benzyl]oxy}-3,3'-bipyridin-4(1H)-one

To a solution of Intermediate 6 (0.85 g) in ethanol (30 ml) was added commercial 30% aqueous ammonia (110 ml) with stirring. The suspension thus obtained was placed into a steel reactor and heated to 140° C. (max. pressure 2×10$^6$ Pa (20 Kg/cm$^2$)). After eight hours of heating, the reactor was allowed to cool to room temperature overnight with mechanical stirring. The precipitate was filtered and washed with ethyl acetate. 0.495 g of the title compound were obtained as a pale brown powder after drying under vacuum.

$^1$H-NMR (δ, ppm, DMSO-d$_6$): 11.15 (bs, 1H); 7.94 (dd, 1H); 7.58 (d, 2H); 7.54 (dd, 1H); 7.37 (d, 2H); 6.88 (d, 1H); 5.92 (s, 1H); 5.38 (s, 2H); 2.18 (s, 3H); 2.08 (s, 3H)

Intermediates 14-19 were prepared by methods analogous to that described for Intermediate 13 replacing Intermediate 6 with the Intermediate shown in Table 2.

TABLE 2

| Int. | R | Starting Intermediate | Chemical name | Physical Data |
|---|---|---|---|---|
| 14 | 3-$CF_3$ | 7 | 2,6-Dimethyl-6'-{[3-(trifluoromethyl)benzyl]oxy}-3,3'-bipyridin-4(1H)-one | $^1$H-NMR (δ, ppm, $CD_3OD$): 7.98 (d, 1H); 7.76 (bs, 1H); 7.74-7.70 (m, 1H); 7.60-7.53 (m, 3H); 6.95 (d, 1H); 6.27 (s, 1H); 5.47 (s, 2H); 2.34 (s, 3H); 2.18 (s, 3H). |
| 15 | 4-$CF_3$ | 8 | 2,6-Dimethyl-6'-{[4-(trifluoromethyl)benzyl]oxy}-3,3'-bipyridin-4(1H)-one | $^1$H-NMR (δ, ppm, DMSO-$d_6$): 11.15 (bs, 1H); 7.93 (s, 1H); 7.75-7.63 (m, 4H); 7.54 (d, 1H); 6.93 (s, 1H); 5.92 (s, 1H); 5,47 (d, 2H); 2.18 (s, 3H); 2.08 (s, 3H). |
| 16 | 2-$CF_3$ | 9 | 2,6-Dimethyl-6'-{[2-(trifluoromethyl)benzyl]oxy}-3,3'-bipyridin-4(1H)-one | $^1$H-NMR (δ, ppm, DMSO-$d_6$): 11.16 (bs, 1H); 7.94 (d, 1H); 7.80-7.69 (m, 3H); 7.60-7.53 (m, 2H); 6.90 (d, 1H); 5.92 (s, 1H); 5.51 (s, 2H); 2.18 (s, 3H); 2.09 (s, 3H). |
| 17 | 3,5-di$CF_3$ | 10 | 2,6-Dimethyl-6'-{[3,5-bis(trifluoromethyl)benzyl]oxy}-3,3'-bipyridin-4(1H)-one | $^1$H-NMR (δ, ppm, DMSO-$d_6$): 11.17 (bs, 1H); 8.18 (s, 2H); 8.07 (s, 1H); 7.95 (d, 1H); 7.57 (dd, 1H); 6.96 (d, 1H); 5.92 (s, 1H); 5.54 (s, 2H); 2.18 s, 3H); 2.08 (s, 3H). |
| 18 | 4-F | 11 | 6'-{[4-Fluorobenzyl]oxy}-2,6-dimethyl-3,3'-bipyridin-4(1H)-one | $^1$H-NMR (δ, ppm, $CD_3OD$): 7.97 (d, 1H); 7.55 (dd, 1H); 7.50-7.46 (m, 2H); 7.11-7.05 (m, 2H); 6.90 (d, 1H); 6.27 (s, 1H); 5.35 (s, 2H); 2.34 (s, 3H); 2.19 (s, 3H). |
| 19 | 3,5-diF | 12 | 6'-{[3,5-Difluorobenzyl]oxy}-2,6-dimethyl-3,3'-bipyridin-4(1H)-one | $^1$H-NMR (δ, ppm, $CD_3OD$): 7.96 (d, 1H); 7.57 (dd, 1H); 7.10-7.03 (m, 2H); 6.95 (d, 1H); 6.89-6.82 (m, 1H); 6.27 (s, 1H); 5.41 (s, 2H); 2.34 (s, 3H); 2.19 (s, 3H). |

Intermediate 20

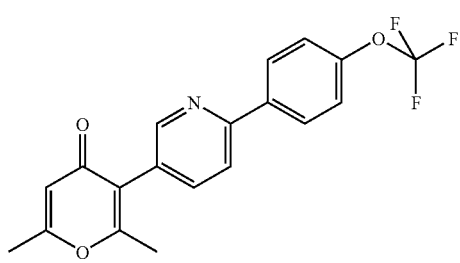

2,6-Dimethyl-3-(6-{4-[(trifluoromethyl)oxy]phenyl}-3-pyridinyl)-4H-pyran-4-one

Method A:

To a solution of Intermediate 5 (2.27 g) in a mixture of toluene (120 ml) and ethanol (60 ml) were added successively dichlorobis(triphenylphosphine)-palladium(II) (LANCASTER, 0.456 g) and 4-trifluoromethoxyphenyl boronic acid (FRONTIER, 1.6 g) and the resulting suspension was deoxygenated by bubbling argon for 5 minutes. Saturated $NaHCO_3$ (23 ml) was added dropwise and the mixture heated to 95° C. for 2.5 h. The mixture was cooled to room temperature and the mixture concentrated to dryness under vacuum. The oily residue thus obtained was dissolved in tertbutyl-methyl ether (400 ml) and washed with 1N NaOH (2×250 ml). The organic layer was washed with 1N HCl (7×100 ml) until no remaining material was detected in the organic layer. The aqueous layer was carefully basified by slow addition of 6N NaOH (80 ml) and 2N NaOH (150 ml), then extracted with tertbutyl-methyl ether (2×300 ml). The combined organic layers were washed with brine (500 ml), dried over $Na_2SO_4$ and concentrated to dryness to afford the 2 g of the title compound as a yellowish powder.

Method B:

To a solution of Intermediate 5 (0.5 g) in a mixture of toluene (8 ml) and ethanol (4 ml) were added successively tetrakis(triphenylphosphine)-palladium(0) (ALDRICH, 0.165 g) and 4-trifluoromethoxyphenyl boronic acid (FRONTIER, 0.443 g) and the resulting suspension was deoxygenated by bubbling argon for 5 minutes. Saturated NaHCO$_3$ (4 ml) was added dropwise and the mixture refluxed for 1 h. On cooling to room temperature water was added and the mixture extracted with ethyl acetate (2×), then diethylether (5×). The organic layer was dried over MgSO$_4$ and the solution concentrated to dryness under vacuum to afford a crude product (814 mg) which was purified by column chromatography on silica gel, eluting with mixtures Hexane/Ethyl acetate v/v 10:1 to afford the title compound.

$^1$H-NMR (δ, ppm, CDCl$_3$): 8.54 (m, 1H); 8.06-8.01 (m, 2H); 7.79-7.72 (m, 2H); 7.32 (bd, 2H); 6.24 (s, 1H); 2.32 (s, 3H); 2.29 (s, 3H)

Intermediates 21-33 were prepared by methods analogous to that described for Intermediate 20 as shown in Table 3.

TABLE 3

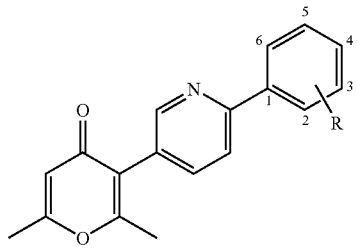

| Int. | R | Meth | Starting Intermediate | Chemical name | Physical Data |
|---|---|---|---|---|---|
| 21 | 3-OCF$_3$ | B | 5 | 2,6-Dimethyl-3-(6-{3-[(trifluoromethyl)oxy]phenyl}-3-pyridinyl)-4H-pyran-4-one | $^1$H-NMR (δ, ppm, CDCl$_3$): 8.56 (s, 1H), 7.95 (bs, 1H), 7.92-7.91 (m, 2H), 7.78-7.76 (m, 2H), 7.29 (bs, 1H), 6.24 (s, 1H), 2.32 (s, 3H), 2.29 (s, 3H) |
| 22 | 2-OCF$_3$ | B | 5 | 2,6-Dimethyl-3-(6-{2-[(trifluoromethyl)oxy]phenyl}-3-pyridinyl)-4H-pyran-4-one | $^1$H-NMR (δ, ppm, CDCl$_3$): 8.59 (bs, 1H), 7.89-7.86 (m, 1H), 7.74-7.72 (m, 2H), 7.46-7.37 (m, 3H), 6.24 (s, 1H), 2.32 (s, 3H), 2.29 (s, 3H) |
| 23 | 4-CF$_3$ | B | 5 | 2,6-Dimethyl-3-(6-{4-[trifluoromethyl]phenyl}-3-pyridinyl)-4H-pyran-4-one | $^1$H-NMR (δ, ppm, CDCl$_3$): 8.58 (m, 1H), 8.13 (bd, 2H); 7.84-7.72 (m, 4H), 6.25 (s, 1H), 2.32 (s, 3H), 2.30 (s, 3H) |
| 24 | 3-CF$_3$ | A | 5 | 2,6-Dimethyl-3-(6-{3-[trifluoromethyl]phenyl}-3-pyridinyl)-4H-pyran-4-one | $^1$H-NMR (δ, ppm, CDCl$_3$): 8.57 (d, 1H), 8.30 (s, 1H), 8.19 (d, 1H), 7.85-7.75 (m, 2H), 7.70-7.58 (m, 2H), 6.24 (s, 1H), 2.32 (s, 3H), 2.29 (s, 3H) |
| 25 | 2-CF$_3$ | A | 5 | 2,6-Dimethyl-3-(6-{2-[trifluoromethyl]phenyl}-3-pyridinyl)-4H-pyran-4-one | $^1$H-NMR (δ, ppm, CDCl$_3$): 8.49 (bs, 1H), 7.77-7.47 (m, 6H), 6.24 (s, 1H), 2.31 (s, 3H), 2.27 (s, 3H) |
| 26 | 4-Cl | B | 5 | 3-(6-{4-Chlorophenyl}-3-pyridinyl)-2,6-dimethyl-4H-pyran-4-one | $^1$H NMR (δ, ppm, CDCl$_3$): 8.58 (s, 1H), 7.74-7.34 (m, 6H), 6.24 (s, 1H), 2.32 (s, 3H), 2.28 s, 3H) |
| 27 | 3-Cl | B | 5 | 3-(6-{3-Chlorophenyl}-3-pyridinyl)-2,6-dimethyl-4H-pyran-4-one | $^1$H NMR (δ, ppm, CDCl$_3$): δ: 8.55 (bs, 1H), 8.03 (bs, 1H), 7.90-7.86 (m, 1H), 7.77-7.75 (m, 2H), 7.42-7.39 (m, 2H), 6.24 (s, 1H), 2.32 (s, 3H), 2.29 (s, 3H) |
| 28 | 2-Cl | B | 5 | 3-(6-{2-Chlorophenyl}-3-pyridinyl)-2,6-dimethyl-4H-pyran-4-one | $^1$H NMR (δ, ppm, CDCl$_3$): δ: 8.58 (s, 1H), 7.74-7.34 (m, 6H), 6.24 (s, 1H), 2.32 (s, 3H), 2.23 (s, 3H) |
| 29 | 4-F | A | 5 | 3-(6-{4-Fluorophenyl}-3-pyridinyl)-2,6-dimethyl-4H-pyran-4-one | $^1$H-NMR (δ, ppm, CD$_3$OD): 8.48 (d, 1H), 8.07-8.02 (m, 2H), 7.91 (d, 1H), 7.78 (dd, 1H), 7.25-7.20 (m, 2H), 6.30 (s, 1H), 2.38 (s, 3H), 2.30 (s, 3H) |

TABLE 3-continued

| Int. | R | Meth | Starting Intermediate | Chemical name | Physical Data |
|---|---|---|---|---|---|
| 30 | 2-F | A | 5 | 3-(6-{2-Fluorophenyl}-3-pyridinyl)-2,6-dimethyl-4H-pyran-4-one | ¹H-NMR (δ, ppm, CD₃OD): 8.53 (d, 1H), 7.91-7.80 (m, 4H), 7.35-7.21 (m, 2H), 6.30 (s, 1H), 2.38 (s, 3H), 2.31 (s, 3H) |
| 31 | 2,4-di-CF₃ | B | 5 | 2,6-Dimethyl-3-(6-{2,4-[bistrifluoromethyl]phenyl}-3-pyridinyl)-4H-pyran-4-one | ¹H-NMR (δ, ppm, CD₃OD): 8.54 (d, 1H), 8.12 (s, 1H), 8.08 (d, 1H), 7.88 (dd, 1H), 7.80 (d, 1H), 7.67-7.61 (m, 1H), 6.30 (s, 1H), 2.39 (s, 3H), 2.31 (s, 3H) |
| 32 | 3,5-di-CF₃ | B | 5 | 2,6-Dimethyl-3-(6-{3,5-[bistrifluoromethyl]phenyl}-3-pyridinyl)-4H-pyran-4-one | ¹H-NMR (δ, ppm, CD₃OD): 8.67 (s, 2H), 8.61 (d, 1H), 8.16 (d, 1H), 8.05 (s, 1H), 7.90 (dd, 1H), 6.30 (s, 1H), 2.39 (s, 3H), 2.32 (s, 3H) |
| 33 | 4-n-C₄H₉— | B | 5 | 3-(6-{4-n-Butylphenyl}-3-pyridinyl)-2,6-dimethyl-4H-pyran-4-one | ¹H-NMR (δ, ppm, CDCl₃): 8.47 (d, 1H), 7.87 (d, 2H), 7.77-7.67 (m, 2H), 7.27 (d, 2H), 6.23 (s, 1H), 2.68-2.63 (m, 2H), 2.30 (s, 3H), 2.27 (s, 3H), 1.67-1.33 (m, 4H), 0.92 (t, 3H) |

Intermediate 24

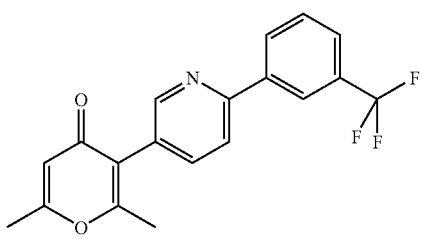

2,6-Dimethyl-3-(6-{3-[trifluoromethyl]phenyl}-3-pyridinyl)-4H-pyran-4-one

Method A:

A solution of Intermediate 5 (45 g) and 3-trifluoromethylphenyl boronic acid (FRONTIER, 30.59 g) in a mixture of toluene (800 ml) and ethanol (400 ml) was deoxygenated by bubbling Argon for 25 minutes, then dichlorobis(triphenylphosphine)-palladium(II) (ALDRICH, 4.5 g) was added and deoxygenation continued for 20 minutes. Saturated NaHCO₃ solution (380 ml) was added dropwise over 30 minutes and the mixture heated at 85° C. for 2 h. The temperature was set to 25° C. and the mixture stirred overnight. The mixture was filtered through a pad of celite and the cake washed with 150 ml of a mixture toluene/ethanol v/v 4/1. The organics were concentrated under vacuum and the resulting mixture partitioned between 1N NaOH (500 ml) and tert-butylmethyl ether (1000 ml). The aqueous layer was extracted with tert-butylmethyl ether (500 ml) and the combined organic layers were washed successively with 1N NaOH (3×500 ml), water (500 ml) and saturated NaCl (500 ml), then dried over Na₂SO₄ overnight. The solution was filtered through a pad of celite and the solution concentrated under vacuum to obtain a slurry which was filtered under vacuum to afford a solid which was washed with tert-butylmethyl ether (2×60 ml). 25.3 g of a first crop of the title compound were obtained. From the mother liquors, a second solid separates, which was filtered under vacuum and washed with tert-butylmethyl ether to afford 5.55 g of a second crop of the title compound.

The combined organics were basified with NaOH 10N and NaOH 2N until pH=11 aprox and the resulting suspension extracted twice with tert-butylmethyl-ether (250+100 ml). The combined organics were washed with water (250 ml) and saturated NaCl (250 ml), then dried over Na₂SO₄. Elimination of the solvent under vacuum gave a solid which was triturated with n-heptane to afford 8.93 g of a third crop of the title compound.

$^1$H-NMR (δ, ppm, CDCl$_3$): 8.57 (d, 1H), 8.30 (s, 1H), 8.19 (d, 1H), 7.85-7.75 (m, 2H), 7.70-7.58 (m, 2H), 6.24 (s, 1H), 2.32 (s, 3H), 2.29 (s, 3H).

Intermediate 34

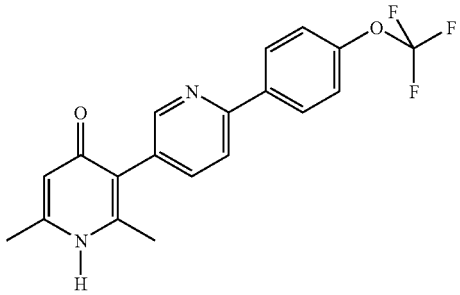

2,6-Dimethyl-6'-{4-[(trifluoromethyl)oxy]phenyl}-3,3'-bipyridin-4(1H)-one

To a solution of Intermediate 20 (2.115 g) in ethanol (13 ml) was added commercial 30% aqueous ammonia (44 ml) with stirring. The suspension thus obtained was placed into a steel reactor and heated to 140° C. (max. pressure 2×10$^6$ Pa (20 Kg/cm$^2$)). After eight hours of heating, the reactor was allowed to cool to room temperature overnight. The precipitate was filtered and washed successively with ethyl acetate and dichloromethane. 1.38 g of the title compound were obtained as a pale brown powder after drying under vacuum.

$^1$H-NMR (δ, ppm, DMSO-d$_6$): 11.24 (bs, 1H); 8.48 (m, 1H); 8.23 (m, 2H); 7.99 (d, 1H); 7.73 (dd, 1H); 7.48 (m, 2H); 5.97 (s, 1H); 2.21 (s, 3H); 2.14 (s, 3H).

Intermediates 35-47 were prepared by methods analogous to that described for Intermediate 34 replacing Intermediate 20 with the Intermediate shown in Table 4.

TABLE 4

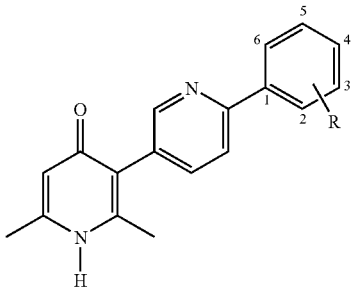

| Int. | R | Starting Intermediate | Chemical name | Physical Data |
|---|---|---|---|---|
| 35 | 3-OCF$_3$ | 21 | 2,6-Dimethyl-6'-{3-[(trifluoromethyl)oxy]phenyl}-3,3'-bipyridin-4(1H)-one | $^1$H-NMR (δ, ppm, DMSO-d$_6$): 11.26 (bs, 1H), 8.49 (s, 1H), 8.14 (d, 1H), 8.08-8.03 (m, 2H), 7.74 (dd, 1H), 7.66-7.61 (m, 1H), 7.42 (d, 1H), 5.97 (s, 1H), 2.21 (s, 3H), 2.14 (s, 3H) |
| 36 | 2-OCF$_3$ | 22 | 2,6-Dimethyl-6'-{2-[(trifluoromethyl)oxy]phenyl}-3,3'-bipyridin-4(1H)-one | $^1$H-NMR (δ, ppm, DMSO-d$_6$): 11.26 (s, 1H), 8.50 (s, 1H), 7.86-7.45 (m, 6H), 5.98 (s, 1H), 2.21 (s, 3H), 2.13 (s, 3H) |
| 37 | 4-CF$_3$ | 23 | 2,6-Dimethyl-6'-{4-[trifluoromethyl]phenyl}-3,3'-bipyridin-4(1H)-one | $^1$H-NMR (δ, ppm, DMSO-d$_6$): 11.27 (bs, 1H), 8.52 (bs, 1H), 8.32 (d, 2H), 8.06 (d, 1H), 7.85 (d, 2H), 7.76 (d, 1H), 5.98 (s,1H), 2.21 (s, 3H), 2.15 (s, 3H) |
| 38 | 3-CF$_3$ | 24 | 2,6-Dimethyl-6'-{3-[trifluoromethyl]phenyl}-3,3'-bipyridin-4(1H)-one | $^1$H-NMR (δ, ppm, DMSO-d$_6$): 11.25 (s, 1H), 8.51 (d, 1H), 8.45 (s, 1H), 8.41 (d, 1H), 8.10 (d, 1H), 7.81-7.71 (m, 3H), 5.98 (s, 1H), 2.21 (s, 3H), 2.14 (s, 3H) |
| 39 | 2-CF$_3$ | 25 | 2,6-Dimethyl-6'-{2-[trifluoromethyl]phenyl}-3,3'-bipyridin-4(1H)-one | $^1$H-NMR (δ, ppm, DMSO-d$_6$): 11.25 (s, 1H), 8.43 (d, 1H), 7.87-7.47 (m, 6H), 5.98 (s, 1H), 2.21 (s, 3H), 2.13 (s, 3H) |
| 40 | 4-Cl | 26 | 6'-(4-Chlorophenyl)-2,6-dimethyl-3,3'-bipyridin-4(1H)-one | $^1$H-NMR (δ, ppm, DMSO-d$_6$): 11.24 (s, 1H), 8.46 (s, 1H), 8.13 (d, 2H), 7.97 (d, 1H), 7.71 (dd, 1H), 7.54 (d, 2H), 5.96 (s, 1H), 2.21 (s, 3H), 2.13 (s, 3H) |

TABLE 4-continued

| Int. | R | Starting Intermediate | Chemical name | Physical Data |
|---|---|---|---|---|
| 41 | 3-Cl | 27 | 6'-(3-Chlorophenyl)-2,6-dimethyl-3,3'-bipyridin-4(1H)-one | $^1$H-NMR ($\delta$, ppm, DMSO-$d_6$): 11.25 (s, 1H), 8.48 (s, 1H), 8.15-8.01 (m, 3H), 7.72 (dd, 1H), 7.53-7.50 (m, 2H), 5.97 (s, 1H), 2.21 (s, 3H), 2.14 s, 3H) |
| 42 | 2-Cl | 28 | 6'-(2-Chlorophenyl)-2,6-dimethyl-3,3'-bipyridin-4(1H)-one | $^1$H-NMR ($\delta$, ppm, DMSO-$d_6$): 11.26 (s, 1H), 8.48 (s, 1H), 7.74-7.45 (m, 6H), 5.98 (s, 1H), 2.21 (s, 3H), 2.15 (s, 3H) |
| 43 | 4-F | 29 | 6'-(4-Fluorophenyl)-2,6-dimethyl-3,3'-bipyridin-4(1H)-one | $^1$H-NMR ($\delta$, ppm, DMSO-$d_6$): 11.23 (s, 1H), 8.44 (d, 1H), 8.18-8.13 (m, 2H), 7.94 (d, 1H), 7.69 (dd, 1H), 7.34-7.28 (m, 2H), 5.96 (s, 1H), 2.21 (s, 3H), 2.13 (s, 3H) |
| 44 | 2-F | 30 | 6'-(2-Fluorophenyl)-2,6-dimethyl-3,3'-bipyridin-4(1H)-one | $^1$H-NMR ($\delta$, ppm, DMSO-$d_6$): 11.20 (s, 1H), 8.50 (d, 1H), 7.97 (dd, 1H), 7.79 (dd, 1H), 7.72 (dd, 1H), 7.52-7.44 (m, 1H), 7.37-7.31 (m, 2H), 5.98 (s, 1H), 2.21 (s, 3H), 2.14 (s, 3H) |
| 45 | 2,4-diCF$_3$ | 31 | 2,6-Dimethyl-6'-{2,4-bis[trifluoromethyl]phenyl}-3,3'-bipyridin-4(1H)-one | $^1$H-NMR ($\delta$, ppm, DMSO-$d_6$): 11.28 (s, 1H), 8.48 (d, 1H), 8.17 (bs, 2H), 7.85 (d, 1H), 7.78 (dd, 1H), 7.57 (d, 1H), 5.99 (s, 1H), 2.22 (s, 3H), 2.14 (s, 3H) |
| 46 | 3,5-diCF$_3$ | 32 | 2,6-Dimethyl-6'-{3,5-bis[trifluoromethyl]phenyl}-3,3'-bipyridin-4(1H)-one | $^1$H-NMR ($\delta$, ppm, DMSO-$d_6$): 11.28 (s, 1H), 8.77 (s, 2H), 8.55 (d, 1H), 8.30 (d, 1H), 8.17 (s, 1H), 7.81 (dd, 1H), 5.98 (s, 1H), 2.22 (s, 3H), 2.15 (s, 3H) |
| 47 | 4-n-C$_4$H$_9$— | 33 | 6'-(4-n-Butylphenyl)-2,6-dimethyl-3,3'-bipyridin-4(1H)-one | $^1$H-NMR ($\delta$, ppm, DMSO-$d_6$): 11.23 (s, 1H), 8.42 (d, 1H), 8.00 (d, 2H), 7.90 (d, 1H), 7.66 (dd, 1H), 7.30 (d, 2H), 5.96 (s, 1H), 2.65-2.60 (m, 2H), 2.21 (s, 3H), 2.13 (s, 3H), 1.62-1.54 (m, 2H), 1.36-1.29 (m, 2H), 0.91 (t, 3H) |

Intermediate 38

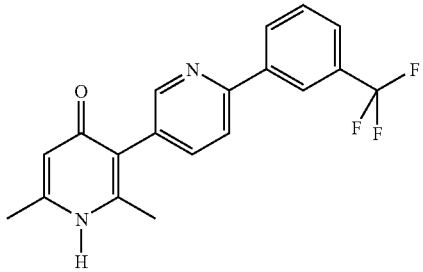

2,6-Dimethyl-6'-{3-[trifluoromethyl]phenyl}-3,3'-bipyridin-4(1H)-one

A suspension of Intermediate 24 (13 g) in a mixture of ethanol (60 ml) and 30% aqueous ammonia (200 ml) was heated at 140° C. in a steel reactor for 8 h, then stirred at room temperature overnight. The solid precipitated was filtered, dried under vacuum, and washed successively with water and ethyl acetate until the washings are colourless. 10.65 g of the title compound were obtained as an off-white powder.

$^1$H-NMR (δ, ppm, DMSO-d$_6$): 11.25 (s, 1H), 8.51 (d, 1H), 8.45 (s, 1H), 8.41 (d, 1H), 8.10 (d, 1H), 7.81-7.71 (m, 3H), 5.98 (s, 1H), 2.21 (s, 3H), 2.14 (s, 3H)

Intermediate 48

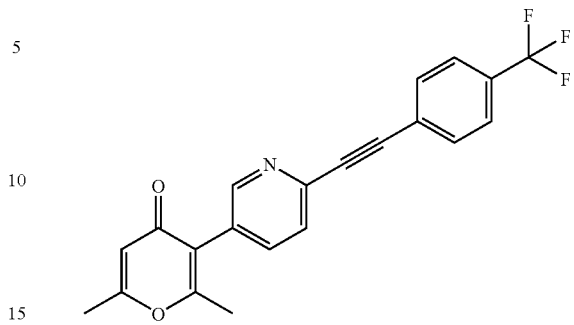

2,6-Dimethyl-3-(6-{[4-(trifluoromethyl)phenyl]ethynyl}-3-pyridinyl)-4H-pyran-4-one To a solution of Intermediate 5 (0.25 g) in a mixture of dry N,N-dimethylformamide (5 ml) and triethylamine (2 ml) were added consecutively CuI (0.0514 g), PdCl$_2$ (PPh$_3$)$_2$ (0.050 g) and PPh$_3$ (0.111 g). The mixture was deoxygenated by bubbling argon and 4-ethynyl-α,α,α-trifluorotoluene (ALDRICH, 0.23 ml) was added, then heated to reflux for 1 h. The mixture was cooled to room temperature, diluted with ethyl acetate and extracted with 1N NH$_4$Cl. The organic layer was concentrated to dryness and dissolved in diethyl ether. The ethereal solution was extracted with 1N HCl until no product was detected in the organic layer. The acidic aqueous solution was basified by adding 2N NaOH and extracted with tert-butyl-methyl-ethyl. Elimination of the solvent gave 0.14 g of the title compound.

$^1$H-NMR (δ, ppm, CD$_3$OD): 8.47 (s, 1H); 7.79 (m, 6H); 6.30 (s, 1H); 2.37 (s, 3H); 2.29 (s, 3H)

Intermediates 49-51 were prepared by methods analogous to that described for Intermediate 48 as indicated in Table 5.

TABLE 5

| Int. | R | Starting Intermediate | Chemical name | Physical Data |
|---|---|---|---|---|
| 49 | 3-CF$_3$-phenyl | 5 | 2,6-Dimethyl-3-(6-{[3-(trifluoromethyl)phenyl]ethynyl}-3-pyridinyl)-4H-pyran-4-one | $^1$H-NMR (δ, ppm, CD$_3$OD): 8.48 (m, 1H); 7.92-7.73 (m, 3H); 7.67-7.52 (m, 3H); 6.30 (s, 1H); 2.37 (s, 3H); 2.29 s, 3H) |
| 50 | 2,4-difluorophenyl | 5 | 3-(6-{[2,4-Difluorophenyl]ethynyl}-3-pyridinyl)-2,6-dimethyl-4H-pyran-4-one | $^1$H-NMR (δ, ppm, CD$_3$OD): 8.46 (bs, 1H); 7.82-7.64 (m, 3H); 7.16-7.02 (m, 2H); 6.30 (s, 1H); 2.37 (s, 3H); 2.29 (s, 3H) |
| 51 | n-C$_5$H$_{11}$— | 5 | 3-(6-{1-Heptynyl})-3-pyridinyl)-2,6-dimethyl-4H-pyran-4-one | $^1$H-NMR (δ, ppm, CDCl$_3$): 8.39 (m, 1H); 7.58 (dd, 1H); 7.42 (d, |

TABLE 5-continued

| Int. | R | Starting Intermediate | Chemical name | Physical Data |
|---|---|---|---|---|
| | | | | 1H); 6.20 (s, 1H); 2.44 (t, 2H); 2.29 (s, 3H); 2.22 (m, 3H); 1.64 (m, 2H); 1.47-1.34 (m, 4H); 0.91 (m, 3H) |

Intermediate 52

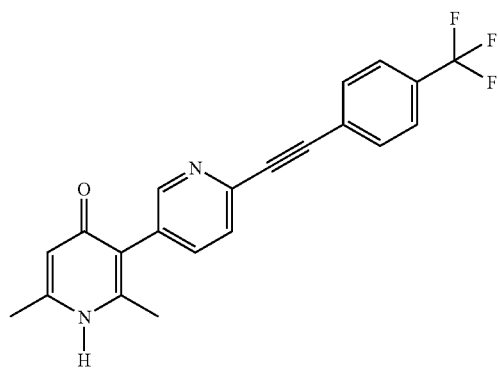

2,6-Dimethyl-6'-{[4-(trifluoromethyl)phenyl]ethynyl}-3,3'-bipyridin-4(1H)-one To a solution of Intermediate 48 (0.07 g) in MeOH (1 ml) was added commercial 30% aqueous ammonia (3 ml) and the suspension heated to 145° C. for 1 h under microwave radiation. Upon cooling, the solid precipitated was filtrated and washed with acetonitrile. 0.035 g of the title compound were obtained.

$^1$H-NMR (δ, ppm, CD$_3$OD): 8.45 (m, 1H); 7.75 (m, 6H); 6.30 (s, 1H); 2.36 (s, 3H); 2.23 (s, 3H)

Intermediate 53 was prepared by a method analogous to that described for Intermediate 52 replacing Intermediate 48 with Intermediate 50, as shown in Table 6.

TABLE 6

| Int. | R | Starting Intermediate | Chemical name | Physical Data |
|---|---|---|---|---|
| 53 | 2,4-diF | 50 | 6'-{[2,4-diifluorophenyl]ethynyl}-2,6-dimethyl-3,3'-bipyridin-4(1H)-one | $^1$H-NMR (δ, ppm, CD$_3$OD): 8.44 (m,1H); 7.79-7.65 (m, 3H); 7.12-7.05 (m, 2H); 6.30 (s, 1H); 2.36 (s, 3H); 2.23 (s, 3H) |

Intermediate 54

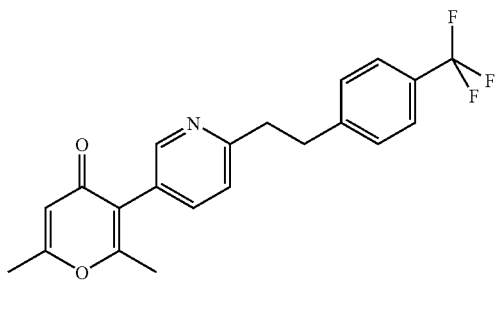

2,6-Dimethyl-3-(6-{2-[4-(trifluoromethyl)phenyl]ethyl}-3-pyridinyl)-4H-pyran-4-one A solution of Intermediate 48 (0.2 g) in a mixture of ethyl acetate/methanol V/V 3:1 (20 ml) was deoxygenated by bubbling argon for 5 minutes, then palladium 10% w/w on activated charcoal (0.050 g) and 1H HCl (0.541 ml) were added. The mixture was hydrogenated at 30 psi for 4 hours. The catalyst was removed by filtration and the solvent evaporated to dryness under vacuum to afford 0.168 g of the title compound.

$^1$H-NMR (δ, ppm, CDCl$_3$): 8.41 (m, 1H); 7.70-7.64 (m, 1H); 7.56-7.52 (m, 2H); 7.33 (d, 2H); 7.17 (d, 1H); 6.21 (m, 2H); 3.14 (m, 4H); 2.30 (s, 3H); 2.23 (s, 3H)

Intermediates 55 and 56 were prepared by methods analogous to that described for Intermediate 54 replacing Intermediate 48 with the Intermediate shown in Table 7.

Intermediate 57

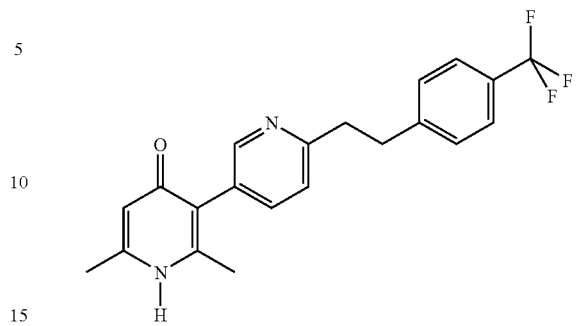

2,6-Dimethyl-6'-{2-[4-(trifluoromethyl)phenyl]ethyl}-3,3'-bipyridin-4(1H)-one To a solution of Intermediate 54 (0.164 g) in MeOH (1 ml) was added commercial 30% aqueous ammonia (3 ml) and the suspension heated to 145° C. for 45 minutes under microwave radiation. Upon cooling, the solid precipitated was filtrated and washed with acetonitrile. 0.092 g of the title compound were obtained.

$^1$H-NMR (δ, ppm, DMSO-d$_6$): 11.18 (bs, 1H); 8.28 (m, 1H); 7.63 (d, 2H); 7.51-7.46 (m, 3H); 7.25 (d, 1H); 5.93 (s, 1H); 3.08 (m, 4H); 2.19 (s, 3H); 2.06 (s, 3H)

Intermediates 58 and 59 were prepared by methods analogous to that described for Intermediate 57 replacing Intermediate 54 with the Intermediate shown in Table 8.

TABLE 7

| Int. | R | Starting Intermediate | Chemical name | Physical Data |
|---|---|---|---|---|
| 55 | 3-CF$_3$-phenyl | 49 | 2,6-Dimethyl-3-(6-{2-[3-(trifluoromethyl)phenyl]ethyl}-3-pyridinyl)-4H-pyran-4-one | $^1$H-NMR (δ, ppm, CD$_3$OD): 8.35 (m, 1H); 7.67.7.54 (m, 3H); 7.46 (m, 2H); 7.31 (d, 1H); 6.27 (bs, 1H); 3,14 (s, 4H); 2.36 (s, 3H); 2.23 (s, 3H) |
| 56 | n-C$_5$H$_{11}$ | 51 | 3-(6-{n-Heptyl}-3-pyridinyl)-2,6-dimethyl-4H-pyran-4-one | $^1$H-NMR (δ, ppm, CDCl$_3$): 8.27 (d, 1H); 7.51 (dd, 3H); 7.19 (d, 2H); 6.19 (s, 1H); 2.76 (m, 2H); 2.27 (s, 3H); 2.19 (s, 3H); 1.69 (m, 2H); 1.36-1.21 (m, 8H); 0.84 (m, 3H) |

TABLE 8

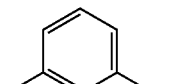

| Int. | R | Starting Intermediate | Chemical name | Physical Data |
|---|---|---|---|---|
| 58 | (3-trifluoromethylphenyl)methyl | 55 | 2,6-Dimethyl-6'-{2-[3-(trifluoromethyl)phenyl]ethyl}-3,3'-bipyridin-4(1H)-one | $^1$H-NMR (δ, ppm, CD$_3$OD): 8.32 (d, 1H); 7.59 (dd, 1H); 7.47 (m, 4H); 7.30 (d, 1H); 6.28 (s, 1H); 3,14 (s, 4H); 2.35 (s, 3H); 2.16 (s, 3H) |
| 59 | n-C$_5$H$_{11}$ | 56 | 6'-(n-Heptyl)-2,6-dimethyl-3,3'-bipyridin-4(1H)-one | $^1$H-NMR (δ, ppm, CD$_3$OD): 8.27 (d, 1H); 7.62 (dd, 1H); 7.35 (d, 1H); 6.28 (s, 1H); 2.82 (m, 2H); 2.34 (s,3H); 2.18 (s, 3H); 1.74 (m, 2H); 1.34 (m, 8H), 0.90 (m, 3H) |

Intermediate 60

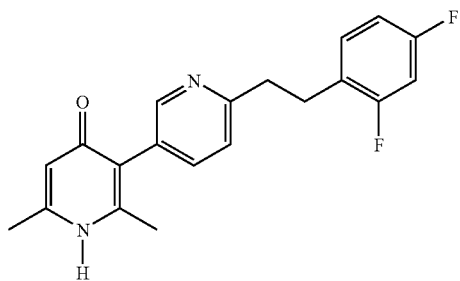

2,6-Dimethyl-6'-{2-[2,4-difluorophenyl]ethyl}-3,3'-bipyridin-4(1H)-one

A solution of Intermediate 53 (0.076 g) in a mixture of ethyl acetate/methanol v/v 3:1 (12 ml) was deoxygenated by bubbling argon for 5 minutes, then Palladium 10% w/w on activated charcoal (0.015 g) was added. The mixture was hydrogenated at 30 psi for 2 hours. The catalyst was removed by filtration and the solvent evaporated to dryness under vacuum to afford 0.065 g of the title compound.

$^1$H-NMR (δ, ppm, CD$_3$OD): 8.30 (m, 1H); 7.59 (dd, 1H); 7.29-7.21 (m, 2H); 6.87 (m, 2H); 6.28 (s, 1H); 3.07 (m, 4H); 2.35 (s, 3H); 2.17 (s, 3H)

Intermediate 61

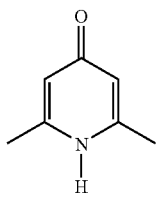

2,6-Dimethyl-4(1H)-pyridinone

To a solution of 2,6-dimethyl-pyran-4-one (ALDRICH, 7.44 g) in ethanol (40 ml) was added commercial 30% aqueous ammonia (140 ml). The mixture was heated to 140° C. in steel reactor for 8 h, then allowed to cool to room temperature overnight. The mixture was filtered and the ethanol removed under vacuum. The precipitate formed was isolated by filtration to afford a first crop of 1.9 g of the title compound. The filtrate was concentrated to dryness to afford a second crop of 5.2 g of the title compound, which were not further purified.

$^1$H-NMR (δ, ppm, CD$_3$OD): 6.15 (s, 2H); 2.30 (s, 6H)

Intermediate 62

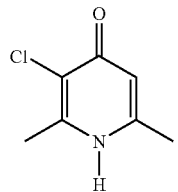

3-Chloro-2,6-dimethyl-4(1H)-pyridinone

A suspension of Intermediate 61 (10 g) and N-chlorosuccinimide (14.3 g) in a mixture of methanol (100 ml) and dichloromethane (250 ml) as solvent was stirred under inert atmosphere at room temperature overnight. The remaining precipitate was filtered and the filtrate concentrated to dryness to afford a residue which was triturated with acetonitrile. The precipitate was filtered and washed with acetonitrile, then dried under vacuum to afford 8.6 g of the title compound.

$^1$H-NMR (δ, ppm, CD$_3$OD): 6.27 (s, 1H); 2.45 (s, 3H); 2.31 (s, 3H)

Intermediate 63

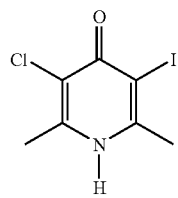

3-chloro-5-iodo-2,6-dimethylpyridin-4(1H)-one

To a solution of sodium hydroxide (2.2 g) in water (340 ml) was added portionwise Intermediate 62 (8.57 g). To the resulting solution was added iodine (13.8 g) and the mixture stirred at room temperature for 1 h. The precipitate was filtered and washed with water and acetonitrile (2×100 ml) to afford 11.5 g of the title compound.

$^1$H-NMR (δ, ppm, CD$_3$OD): 2.59 (s, 3H); 2.45 (s, 3H)

Intermediate 64

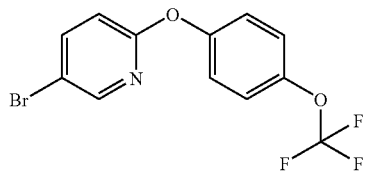

5-Bromo-2-({4-[(trifluoromethyl)oxy]phenyl}oxy)pyridine

To a mixture of 4-trifluoromethoxyphenol (4.4 ml) and sodium hydride (60% dispersion in mineral oil, 1.35 g) in dry DMF (3 ml) was added a solution of 2,5-dibromopyridine in dry DMF (3 mL). The mixture was heated at 60° C. for 8 h. Upon cooling, ethyl acetate was added and the mixture was washed with NH$_4$Cl 1N. The organic layer was dried (Na$_2$SO$_4$) and the solvent evaporated under reduced pressure. The crude product was purified by column chromatography on silica gel (eluent:AcOEt/Hexane 1:10) to afford 1.08 g of the title compound as a colorless oil.

$^1$H-NMR (δ, ppm, CDCl$_3$): 8.21 (d, 1H), 7.80 (dd, 1H), 7.25 (d, 2H), 7.14 (d, 2H), 6.87 (d, 1H).

Intermediate 65

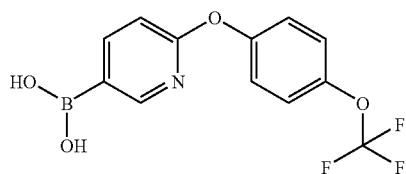

[6-({4-[(Trifluoromethyl)oxy]phenyl}oxy)-3-pyridinyl]boronic acid

A solution of Intermediate 64 (0.60 g) and triisopropyl borate (0.54 mL), in dry THF (6 mL) was added n-BuLi 1.6M (1.24 mL) at −78° C. The reaction was allowed to warm to room temperature and stirred for 8 h, then quenched by addition of HCl 2N until pH=2. After stirring for 1 h, the aqueous phase was extracted with ethyl acetate, the organic phase was dried (Na$_2$SO$_4$), evaporated under reduced pressure and the crude was washed with pentane to yield 0.330 g of the title compound as a white solid.

$^1$H NMR (δ, ppm, CD$_3$OD): 8.45 (d, 1H), 8.16 (dd, 1H), 7.41 (d, 2H), 7.25 (d, 2H), 7.03 (d, 1H)

Intermediate 66

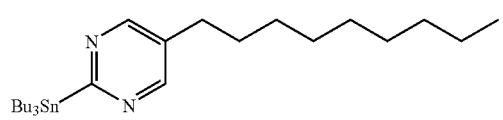

5-Nonyl-2-(tributylstannanyl)pyrimidine

Tri-n-butylstannane (ALDRICH, 0.40 ml) was added dropwise, with vigorous stirring, to a solution of lithium diisopropylamide (ALDRICH, 0.75 ml) in dry THF (3 ml) at 0° C. After stirring for 20 minutes a solution of 2-chloro-5-nonylpyrimidine (ALFA, 0.200 g) in THF (3 ml) was added dropwise at −78° C., under argon atmosphere. After 1 hour at −78° C. the cooling bath was removed and the reaction mixture warmed up to 0° C. The mixture was stirring for 3 hours at 0° C., then quenched with saturated NH$_4$Cl (10 ml), diluted, extracted with ethyl acetate (3×10 ml), dried over MgSO$_4$, concentrated under vacuum and purified by column chromatography on silica gel, eluting with hexane to afford 0.5 g of the title compound as a yellow oil. Although the material obtained contained a small amount of 5-nonyl-pyrimidine, it was used for the next step without further purification.

$^1$H NMR (δ, ppm, CDCl$_3$): 8.52 (s, 2H), 2.52 (t, 2H), 1.63-1.53 (m, 8H), 1.39-1.26 (m, 18H), 1.19-1.14 (m, 6H), 0.87 (t, 12H).

Intermediate 67

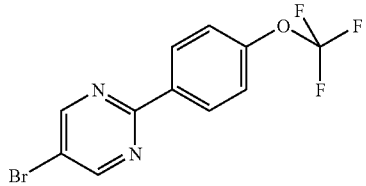

5-Bromo-2-[4-(trifluoromethyloxy)phenyl]pyrimidine 5-bromo-2-iodopyrimidine (0.320 g), 4-(trifluoromethyloxy)phenylboronic acid (FRONTIER SCIEN., 0.231 g), tetrakis(triphenylphosphine)palladium(0) (ALDRICH, 0.026 g) and sodium carbonate (1.6 ml, 2M in H$_2$O) in dry toluene (2.8 ml) was refluxed for 24 hours under argon atmosphere. After cooling to room temperature, H$_2$O (5 ml) was added to the reaction mixture. The layers were separated and the aqueous layer was extracted with CH$_2$Cl$_2$ (3×15 ml). The combined organic layers were washed with brine, dried over MgSO$_4$, concentrated under vacuum and purified by column chromatography on silica gel, eluting with EtOAc-hexane 1:20 to give 0.248 g of the desired product as a white solid.

$^1$H-NMR (δ, ppm, CDCl$_3$): 8.84 (s, 2H), 8.46 (d, 2H), 7.32 (d, 2H)

Intermediate 68

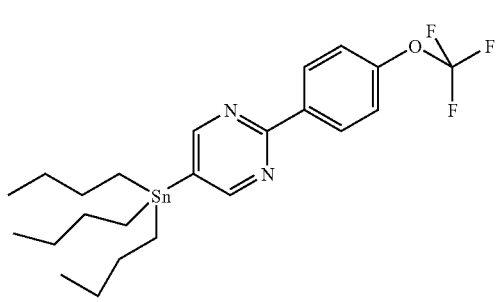

5-(Tributylstannyl)-2-[4-(trifluoromethyloxy)phenyl]pyrimidine n-BuLi 2.0M (ALDRICH, 0.08 ml) was added dropwise, with vigorous stirring, to a solution of Intermediate 67 (0.040 g) in THF (1.30 ml) at −78° C. After stirring for 1 hour, tributyltin chloride (0.044 ml) was added dropwise at −78° C., under argon atmosphere. After 1 hour 15 minutes at −78° C., the reaction was quenched with 1 N NH$_4$Cl (2 ml), diluted, extracted with ethyl acetate (3×10 ml), washed with brine, dried over MgSO$_4$, concentrated under vacuum and purified by chromatography column using EtOAc-hexane 1:40 as eluent to give 0.014 g of the desired product as a yellow oil.

$^1$H-NMR (δ, ppm, CDCl$_3$): 8.77 (s, 2H), 8.48 (d, 2H), 7.34 (d, 2H), 1.65-1.49 (m, 6H), 1.41-1.30 (m, 7H), 1.20-1.13 (m, 5H), 0.90 (t, 9H).

Intermediate 69

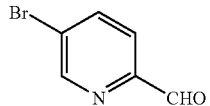

5-Bromo-2-formyl-pyridine

To a solution of 2,5-dibromopyridine (1 g) in toluene (50 mL) at −78° C. was slowly added 2.5M n-BuLi (2 mL). The reaction mixture was stirred for 2 h, then DMF (0.5 mL) was added. The solution was stirred for 1 h at −78° C., then warmed to −10° C. Saturated NH$_4$Cl (10 mL) was added and the mixture was allowed to warm to room temperature. The two phases were partitioned and the organic layer dried over sodium sulfate and the solvent concentrated to dryness to afford 0.432 g of the title compound.

$^1$H NMR (δ, ppm, CDCl$_3$): 10.04 (s, 1H), 8.85 (d, 1H), 8.03 (dd, 1H), 7.85 (d, 1H)

Intermediate 70

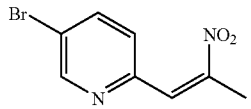

5-Bromo-2-[2-nitro-1-propen-1-yl]pyridine

A solution of Intermediate 69 (0.5 g) and butylamine (0.42 mL) in toluene (3 mL), was heated for 2 h, removing the water formed in a Dean-Stark trap. The toluene was evaporated and acetic acid (AcOH) (2 mL) and nitroethane were added successively to the residue. The solution was heated at 100° C. for 2 h, then cooled to room temperature. Water was added and the phases partitioned. The aqueous layer was extracted with ethyl acetate and the combined organics washed with 5% NaHCO$_3$ solution, dried over sodium sulfate and concentrated to yield 0.365 g of the title compound as a brownish solid.

$^1$H NMR (δ, ppm, CDCl$_3$): 8.77 (d, 1H), 7.91-7.88 (m, 2H), 7.32 (d, 1H), 2.74 (bs, 3H)

Intermediates 71-73

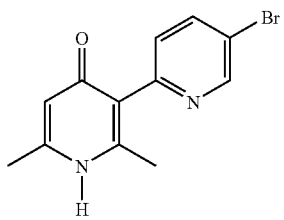

5-Bromo-2',6'-dimethyl-2,3'-bipyridin-4'(1'H)-one

To a suspension of iron powder (5.2 g) in AcOH (28 mL) was added dropwise a solution of Intermediate 70 (2.2 g) in AcOH (18 mL). The mixture was heated at 120° C. for 2 h, diluted with water and extracted with CH$_2$Cl$_2$. The organic layer was dried over Na$_2$SO$_4$ and concentrate to dryness to afford 1.6 g of Intermediate 71, as a dark solid which was not further purified. Intermediate 71 was dissolved in Ac$_2$O (4 mL) and dropped onto a solution of Eaton's reagent (7 mL) and Ac$_2$O (3.6 mL). The mixture was heated at 50° C. for 1 h.

Water and diethylether (Et$_2$O) were added, the organic layer was dried over Na$_2$SO$_4$ and evaporated under reduced pressure to afford Intermediate 72, which not further purified. Crude Intermediate 72 was dissolved ethanol (25 ml) and commercial 30% aqueous ammonia (75 ml) was added. The mixture was heated at 140° C. in a steel reactor for 8 h, then allowed to cool to room temperature overnight. The solvent was evaporated under reduced pressure and the crude product was purified by column chromatography on silica gel (eluent: CH$_2$Cl$_2$/CH$_3$OH, 10:1) to give 0.3 g of the title compound.

$^1$H NMR (δ, ppm, DMSO-d$_6$): 11.22 (s, 1H), 8.67 (d, 1H), 7.98 (dd, 1H), 7.39 (d, 1H), 5.97 (s, 1H), 2.19 (s, 3H), 2.12 (s, 3H)

Intermediate 74

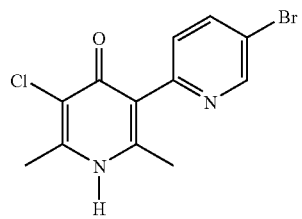

5-Bromo-5'-chloro-2',6'-dimethyl-2,3'-bipyridin-4'(1'H)-one

To a solution of pyridone Intermediate 73 (0.100 g) in a mixture dichloromethane/methanol v/v 4:1 (5 ml) was added portionwise trichloroisocyanuric acid (0.030 g). After stirring for 3 h, the solvent was evaporated to dryness and the residue purified by column chromatography on silica gel (eluent dichloromethane/methanol v/v 10:1) to afford 0.056 g of the title compound.

$^1$H NMR (δ, ppm, DMSO-$d_6$): 11.71 (s, 1H), 8.70 (d, 1H), 8.03 (dd, 1H), 7.40 (d, 1H), 2.38 (s, 3H), 2.13 (s, 3H)

Intermediate 75

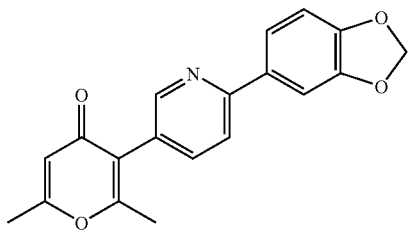

2,6-Dimethyl-3-(6-{4-[3,4-methylendioxy]phenyl}-3-pyridinyl)-4H-pyran-4-one

To a solution of Intermediate 5 (0.35 g) in a mixture of toluene (8 ml) and ethanol (4 ml) were added successively tetrakis(triphenylphosphine)-palladium(0) (ALDRICH, 0.115 g) and 3,4-methylenedioxyphenyl-boronic acid (ALDRICH, 0.249 g) and the resulting suspension stirred under Argon atmosphere. Saturated NaHCO$_3$ (4 ml) was added dropwise and the mixture refluxed (aprox 80° C.) for 1 h 30 minutes. Upon cooling to room temperature water was added and the organic layer concentrated under vacuum. The resulting crude was dissolved in ethyl acetate (50 ml) and the solution extracted with 1N HCl (3×15 ml). The aqueous layer was strongly basified by adding 2N NaOH, then re-extracted with tert-butylmethyl ether (2×15 ml) and ethyl acetate (20 ml). The combined organics were washed with brine, dried over sodium sulphate and concentrated to dryness. 0.299 g of the title compound were obtained as a yellow powder which was used for the next step without further purification.

$^1$H-NMR (δ, ppm, CD$_3$OD): 8.43 (dd, 1H), 7.84 (dd, 1H), 7.74 (dd, 1H), 7.54 (d, 1H), 7.51 (s, 1H), 6.94 (d, 1H), 6.29 (s, 1H), 6.02 (s, 2H), 2.37 (s, 3H), 2.29 (s, 3H); [ES MS] m/z 322.16 (M+1$^+$), 320.22 (M−1$^+$).

Intermediates 76-83 were prepared either by a method analogous to Method B described for Intermediate 20, or a method analagous to that described for Intermediate 75, as indicated in Table 3a.

TABLE 3a

| Int. | R | Meth | Starting Intermediate | Chemical name | Physical Data |
|---|---|---|---|---|---|
| 76 | 2-Cl,4-CF$_3$ | B, as Intermediate 20 | 5 | 3-(6-[2-chloro-4-(trifluoromethyl)phenyl]-3-pyridinyl-2,6-dimethyl-4H-pyran-4-one | $^1$H NMR (δ, ppm, CDCl$_3$): 8.60 (s, 1H), 7.81-7.77 (m, 4H), 7.63 (d, 1H), 6.25 (s, 1H), 2.33 (s, 3H), 2.31 (s, 3H). |
| 77 | 2-F,5-CF$_3$ | B, as Intermediate 20 | 5 | 3-(6-[2-fluoro-5-(trifluoromethyl)phenyl]-3-pyridinyl-2,6-dimethyl-4H-pyran-4-one | $^1$H NMR (δ, ppm, CDCl$_3$): 8.61 (dd, 1H), 8.39 (dd, 1H), 7.92-7.88 (m, 1H), 7.77-7.74 (m, 1H), 7.68-7.63 (m, 1H), 7.32 (s, 1H), 7.29 (s, 1H), 6.24 (s, 1H), 2.32 (s, 3H), 2.30 (s, 3H). |
| 78 | 2-Cl,5-CF$_3$ | as Intermediate 75 | 5 | 3-(6-[2-chloro-5-(trifluoromethyl)phenyl]-3-pyridinyl-2,6-dimethyl-4H-pyran-4-one | $^1$H NMR (δ, ppm, CDCl$_3$): 8.61 (s, 1H), 7.96 (s, 1H), 7.78 (s, 2H), 7.60 (s, 2H), 6.25 (s, 1H), 2.33 (s, 3H), 2.31 (s, 3H). |
| 79 | 2-F,4-CF$_3$ | B, as Intermediate 20 | 5 | 3-(6-[2-fluoro-4-(trifluoromethyl)phenyl]-3-pyridinyl-2,6-dimethyl-4H-pyran-4-one | $^1$H NMR (δ, ppm, CDCl$_3$): 8.61 (s, 1H), 8.19 (t, 1H), 7.80 (dd, 1H), 7.75 (dd,1H), 7.69 (d, 1H), 7.65 (d, 1H), 6.24 (s, 1H), 2.23 (s, 3H), 2.30 (s, 3H). |

TABLE 3a-continued

| Int. | R | Meth | Starting Intermediate | Chemical name | Physical Data |
|---|---|---|---|---|---|
| 80 | 4-O-"Bu | as Intermediate 75 | 5 | 2,6-Dimethyl-3-(6-{[4-butyloxy]phenyl}-3-pyridinyl)-4H-pyran-4-one | ¹H-NMR (δ, ppm, CD₃OD): 8.43 (d, 1H), 7.93 (d, 2H), 7.86 (d, 1H), 7.74 (dd, 1H), 7.03 (m, 2H), 6.29 (s, 1H), 4.04 (t, 2H), 2.37 (s, 3H), 2.30 (s, 3H), 1.73-1.83 (m, 2H), 1.59-1.47 (m, 2H), 1.00 (t, 3H) |
| 81 | 3-Cl,4-O—"Pr | as Intermediate 75 | 5 | 2,6-Dimethyl-3-(6-{[3-chloro,4-propyloxy]phenyl}-3-pyridinyl)-4H-pyran-4-one | ¹H-NMR (δ, ppm, CD₃OD): 8.40 (bs, 1H), 8.06 (s, 1H), 7.90 (m, 2H), 7.75 (m, 1H), 7.16 (m, 1H), 6.30 (s, 1H), 4.08 (t, 2H), 2.38 (s, 3H), 2.30 (s, 3H), 1.87 (m, 2H), 1.10 (t, 3H) |
| 82 | 4-O—Prⁱ | as Intermediate 75 | 5 | 2,6-Dimethyl-3-(6-{[4-isopropyloxy]phenyl}-3-pyridinyl)-4H-pyran-4-one | ¹H-NMR (δ, ppm, CD₃OD): 8.42 (bs, 1H), 7.92 (d, 2H), 7.86 (d, 1H), 7.75 (d, 1H), 7.02 (d, 2H), 6.29 (s, 1H), 4.68 (m, 1H), 2.38 (s, 3H), 2.30 (s, 3H), 1.35 (s, 3H), 1.33 (s, 3H) |
| 83 | 4-O—CH₂Ph | B, as Intermediate 20 | 5 | 2,6-Dimethyl-3-(6-{4-[benzyloxy]phenyl}-3-pyridinyl)-4H-pyran-4-one | ¹H-NMR (δ,ppm, CD₃OD): 8.43-8.42 (m, 1H), 7.94 (d, 2H), 7.87-7.84 (m, 1H), 7.74 (dd, 1H), 7.67-7.54 (m, 1H), 7.47-7.44 (m, 2H), 7.40-7.28 (m, 2H), 7.12 (d, 2H), 6.29 (s, 1H), 5.16 (s, 2H), 2.37 (s, 3H), 2.30 (s, 3H) |

NOTES:
Crude Intermediates 81, 82 and 83 were re-extracted with ethyl acetate instead of tert-butyl-methylether
Crude Intermediates 75, 78 and 80 were extracted with tert-butyl-methylether instead of ethyl acetate.

Intermediate 84

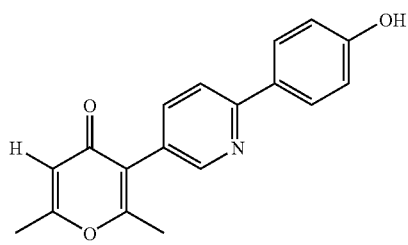

2,6-Dimethyl-3-(6-{4-hydroxyphenyl}-3-pyridinyl)-4H-pyran-4-one

A solution of Intermediate 83 (0.810 g) in a mixture of ethyl acetate/ethanol v/v 3.5:1 (45 ml) was degassed with nitrogen for 5 minutes, then palladium 10% w/w on active charcoal (ALDRICH, 0.124 g) and 1N HCl (1.0 ml) were added. The mixture was hydrogenated at 45 psi for 24 hours and then an additional amount of catalyst (0.060 g) was added. Hydrogenation continued at 45 psi for 21 hours. The catalyst was removed by filtration and the solvent concentrated under vacuum to give a yellow solid. The crude was purified by column chromatography on silica gel, eluting with MeOH—CH₂Cl₂ 1:100 to 1:19 to afford 0.454 g of the desired product as a yellow solid.

¹H NMR (δ, ppm, CD₃OD)) δ ppm; 8.40 (dd, 1H), 7.85-7.80 (m, 3H), 7.72 (dd, 1H), 6.90 (d, 2H), 6.29 (d, 1H), 2.37 (s, 3H), 2.30 (s, 3H). [ES MS] m/z 294 [M+H]⁺

Intermediate 85

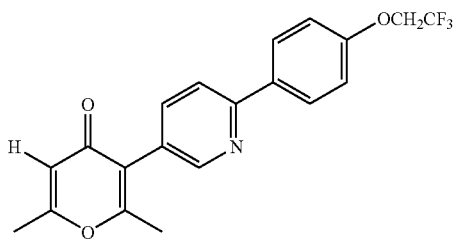

2,6-Dimethyl-3-(6-{4-[2,2,2-trifluoroethyloxy]phenyl}-3-pyridinyl)-4H-pyran-4-one A mixture of Intermediate 84 (0.100 g), 2-iodo-1,1,1-trifluoroethane (ALDRICH, 0.07 ml), cesium carbonate (ALDRICH, 0.222 g) in dry N,N-dimethylformamide were deoxygenated by bubbling argon for 2 minutes. The mixture was heated at 50° C. for 17 hours in a sealed tube, then 2-iodo-1,1,1-trifluoroethane (0.05 ml) was added and the mixture was heated at 50° C. for 6 hours more. After cooling to room temperature, water (4 ml) was added and the mixture was extracted with ethyl acetate. The organic layer was washed with $NH_4Cl$ (3×15 ml), brine, dried over $Na_2SO_4$, concentrated under vacuum and purified by chromatography on silica gel, eluting with EtOAc—$H_2Cl_2$ 1:10 to 1:1 to afford 0.067 g of the desired product as a yellow solid.

$^1$H NMR (δ, ppm, $CD_3OD$) δ ppm; 8.46 (dd, 1H), 8.00 (d, 2H), 7.89 (dd, 1H), 7.76 (dd, 1H), 7.15 (d, 2H), 6.30 (d, 1H), 4.61 (q, 2H), 2.38 (s, 3H), 2.30 (s, 3H). [ES MS] m/z 376 $[M+H]^+$ Intermediate 86

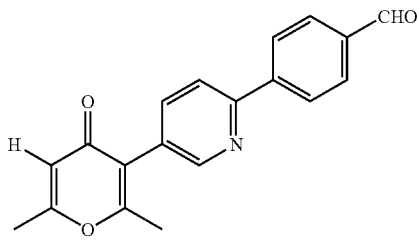

2,6-Dimethyl-3-(6-{4-formylphenyl}-3-pyridinyl)-4H-pyran-4-one

To solution of Intermediate 5 (1.0 g) and 4-(hydroxymethyl)benzene boronic acid (ALDRICH, 0.653 g) in a mixture of toluene (24 ml) and ethanol (12 ml) were added tetrakis (triphenylphosphine)-palladium(0) (ALDRICH, 0.331 g) and saturated $NaHCO_3$ (12 ml) and the resulting mixture was deoxygenated by bubbling argon for 5 minutes. Then, the mixture was heated at 80-85° C. for 4 hours. After cooling to room temperature, the mixture was partitioned and the aqueous layer neutralized with 1N HCl and extracted with dichloromethane. The toluene was eliminated under vacuum from the original organic layer and the oily residue dissolved in ethyl acetate and extracted with 1N HCl (3×20 ml).

This acidic aqueous layer were carefully basified with 2N NaOH, then extracted with ethyl acetate (3×40 ml). Both organic layers were separately washed with brine, dried over $Na_2SO_4$ and concentrated to dryness under vacuum. The combined mixture was purified by column chromatography on silica gel, eluting with EtOAc—$H_2Cl_2$ 1:5 to 4:1 to afford 0.136 g of the title product as a yellow solid along with 0.641 g of 2,6-dimethyl-3-(6-{4-[hydroxymethyl]phenyl}-3-pyridinyl)-4H-pyran-4-one as a yellow solid.

$^1$H-NMR (δ, ppm, $CDCl_3$): 10.09 (s, 1H), 8.60 (d, 1H), 8.20 (d, 2H), 8.01 (d, 2H), 7.88 (dd, 1H), 7.79 (dd, 1H), 6.25 (s, 1H), 2.33 (s, 3H), 2.30 (s, 3H)

Intermediate 87

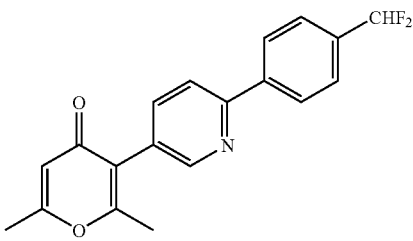

2,6-Dimethyl-3-(6-{4-[difluoromethyl]phenyl}-3-pyridinyl)-4H-pyran-4-one

To powdered Intermediate 86 (0.100 g) at 0° C. under nitrogen was carefully added, dropwise, neat diethylaminosulfur trifluoride (DAST, ALDRICH, 2.0 ml) and the mixture was allowed to reach room temperature. After 25 hours the mixture was cooled at 0° C. and $H_2O$ was carefully added. The resulting mixture was diluted with dichloromethane (3×15 ml) and the organic layer washed with $NaHCO_3$ 10% (1×15 ml) and brine, dried over $Na_2SO_4$ and concentrated under vacuum to give a crude brown oil which was purified by chromatography on silica gel, eluting with $CH_2Cl_2$ to MeOH:$CH_2Cl_2$ 1:100 to afford 0.104 g of the title product as a brown solid.

$^1$H NMR (δ, ppm, $CDCl_3$) δ ppm; 8.58 (dd, 1H), 8.11 (d, 2H), 7.84 (dd, 1H), 7.78 (dd, 1H), 7.63 (d, 2H), 6.72 (t, 1H), 6.24 (s, 1H), 2.32 (s, 3H), 2.30 (s, 3H). [ES MS] m/z 328 $[M+H]^+$ Intermediate 88

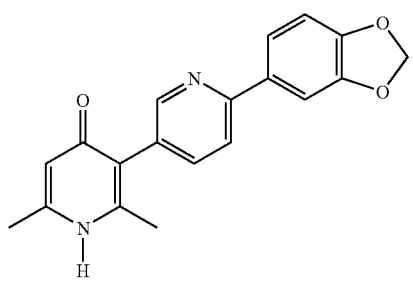

2,6-Dimethyl-6'-{[3,4-methylendioxy]phenyl}-3,3'-bipyridin-4(1H)-one

In a 10 ml microwave tube were introduced successively Intermediate 75 (0.26 g), methanol (1 ml) and 30% aqueous ammonia (4 ml). The suspension thus obtained was deaereated with nitrogen, then heated at 140° C. in a microwave oven for 45 minutes (Pressure limit=1.6×106 Pa (16 bar)), very high absorption). Upon cooling to room temperature, the resulting precipitate was filtered under vacuum, dried and washed with a mixture of diethyl ether/hexane v/v 1:1. 0.143 g of the title compound were obtained as a brown powder.

$^1$H-NMR (δ, ppm, CD$_3$OD): 8.41 (d, 1H), 7.83 (dd, 1H), 7.72 (dd, 1H), 7.51 (dd, 1H), 7.49 (s, 1H), 6.93 (dd, 1H), 6.30 (s, 1H), 6.02 (s, 2H), 2.36 (s, 3H), 2.23 (s, 3H); [ES MS] m/z 321.16 (M+1$^+$), 319.15 (M−1$^+$)

Intermediates 89-97 were prepared by methods analagous to that described for Intermediate 88 starting from the Intermediates as indicated in Table 4a.

TABLE 4a

| Int. | R | Starting Intermediate | Chemical name | Physical Data |
|---|---|---|---|---|
| 89 | 2-Cl,4-CF$_3$ | 76 | 6'-[2-chloro-4-(trifluoromethyl)phenyl]-2,6-dimethyl-3,3'-bipyridin-4(1H)-one. | $^1$H NMR (δ, ppm, DMSO-d$_6$): 11.28 (s, 1 H), 8.53 (s, 1 H), 8.01 (s, 1 H), 7.86-7.77 (m, 4H), 5.99 (s, 1 H), 2.22 (s, 3 H), 2.15 (s, 3 H). |
| 90 | 2-F,5-CF$_3$ | 77 | 6'-[2-fluoro-5-(trifluoromethyl)phenyl]-2,6-dimethyl-3,3'-bipyridin-4(1H)-one | $^1$H NMR (δ, ppm, DMSO-d$_6$): 11.27 (s, 1 H), 8.56 (s, 1 H), 8.35 (dd, 1 H), 7.91-7.77 (m, 3 H), 7.62 (t, 1 H), 5.98 (s, 1 H), 2.21 (s, 3 H), 2.15 (s, 3 H). |
| 91 | 2-Cl,5-CF$_3$ | 78 | 6'-[2-chloro-5-(trifluoromethyl)phenyl]-2,6-dimethyl-3,3'-bipyridin-4(1H)-one | $^1$H NMR (δ, ppm, DMSO-d$_6$): 11.27 (s, 1 H), 8.53 (t, 1 H), 7.96 (s, 1 H), 7.84-7.78 (m, 4 H), 5.99 (s, 1 H), 2.22 (s, 3 H), 2.15 (s, 3 H). |
| 92 | 2-F,4-CF$_3$ | 79 | 6'-[2-fluoro-4-(trifluoromethyl)phenyl]-2,6-dimethyl-3,3'-bipyridin-4(1H)-one | $^1$H NMR (δ, ppm, DMSO-d$_6$): 11.24 (s, 1 H), 8.57 (s, 1 H), 8.20 (t, 1 H), 7.86-7.72 (m, 4 H), 5.98 (s, 1 H), 2.22 (s, 3 H), 2.15 (s, 3 H). |
| 93 | 4-O-$^n$Bu | 80 | 2,6-Dimethyl-6'-{[4-butyloxy]phenyl}-3,3'-bipyridin-4(1H)-one- | $^1$H-NMR (δ, ppm, CD$_3$OD): 8.41 (dd, 1 H), 7.92 (d, 2 H), 7.85 (dd, 1 H), 7.72 (dd, 1 H), 7.03 (dd, 2 H), 6.30 (s, 1 H), 4.05 (t, 2 H), 2.36 (s, 3 H), 2.24 (s, 3 H), 1.84-1.74 (m, 2 H) 1.59-1.47 (m, 2 H), 1.00 (t, 3 H) |
| 94 | 3-Cl,4-O—$^n$Pr | 81 | 2,6-Dimethyl-6'-{[3-chloro,4-propyloxy]phenyl}-3,3'-bipyridin-4(1H)-one | $^1$H-NMR (δ, ppm, CD$_3$OD): 8.42 (bs, 1 H), 8.05 (s, 1 H), 7.88 (m, 2 H), 7.75 (m, 1 H), 7.16 (m, 1 H), 6.30 (s, 1 H), 4.08 (t, 2 H), 2.36 (s, 3 H), 2.24 (s, 3 H), 1.87 (m, 2 H), 1.10 (t, 3 H) |
| 95 | 4-O—Pr$^i$ | 82 | 2,6-Dimethyl-6'-{[4-isopropyloxy]phenyl}-3,3'-bipyridin-4(1H)-one | $^1$H-NMR (δ, ppm, DMSO-d$_6$): 11.28 (bs, 1 H), 8.38 (bs, 1 H), 8.01 (d, 2 H), 7.85 (d, 1 H), 7.60 (d, 1 H), 7.00 (d, 2 H), 5.95 (s, 1 H), 4.65 (m, 1 H), 2.21 (s, 3 H), 2.13 (s, 3 H), 1.30 (s, 3 H), 1.28 (s, 3 H) |
| 96 | 4-O—CH$_2$CF$_3$ | 85 | 2,6-Dimethyl-6'-{4-[2,2,2- | $^1$H-NMR (δ, ppm, CD$_3$OD + CDCl$_3$): 8.44 (dd, 1 H), |

TABLE 4a-continued

| Int. | R | Starting Intermediate | Chemical name | Physical Data |
|---|---|---|---|---|
| | | | trifluoroethoxy]phenyl}-3,3'-bipyridin-4(1H)-one- | 7.98 (d, 2 H), 7.89-7.86 (m, 1 H), 7.75 (dd, 1 H), 7.14 (dd, 2 H), 6.30 (s, 1 H), 4.64-4.56 (m, 2 H), 2.36 (s, 3 H), 2.24 (s, 3 H); [ES MS] m/z 375 [M + H]$^+$ |
| 97 | 4-O—CHF$_2$ | 87 | 2,6-Dimethyl-6'-{4-[difluoromethyl]phenyl}-3,3'-bipyridin-4(1H)-one | $^1$H-NMR (δ, ppm, CD$_3$OD): 8.51 (dd, 1 H), 8.13 (d, 2 H), 7.98 (dd, 1 H), 7.80 (dd, 1 H), 7.68 (d, 2 H), 6.84 (t, 1 H), 6.31 (s, 1 H), 2.37 (s, 3 H), 2.25 (s, 3 H); [ES MS] m/z 327 [M + H]$^+$ |

NOTES:
Compounds 89-92 were prepared by experimental procedures analogous to that described above for Intermediate 88 by using a mixture of ethanol (1 ml) and 30% aqueous ammonia (3 ml) as solvent and heating in the microwave oven at 140° C. for 60 minutes. The solids precipitated were washed with diethyl ether.

Intermediate 98

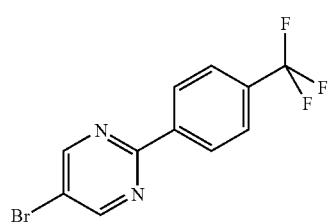

5-bromo-2-(4-trifluoromethylphenyl)pyrimidine 5-bromo-2-iodopyrimidine (250 mg), 4-trifluoromethylphenylboronic acid (167 mg), bis(triphenylphosphine)palladium(II) chloride (22 mg) and Na$_2$CO$_3$ (2.1 ml, 1M in H$_2$O) in argon saturated acetonitrile (2.1 ml) was heated under microwave conditions (150° C., 10 minutes). The conversion was monitored and analyzed by HPLC. The crude reaction mixture was concentrated to dryness, then diluted with CH$_2$Cl$_2$, washed with water (3×10 ml), dried over Na$_2$SO$_4$, concentrated under vacuum and purified by chromatography column using CH$_2$Cl$_2$-hexane 1:10 as eluent to give 160 mg of the desired product as a white solid.

$^1$H NMR (300 MHz, ClCD$_3$) δ ppm; 8.88 (s, 2H), 8.54 (d, 2H), 7.75 (d, 2H).

Intermediate 99

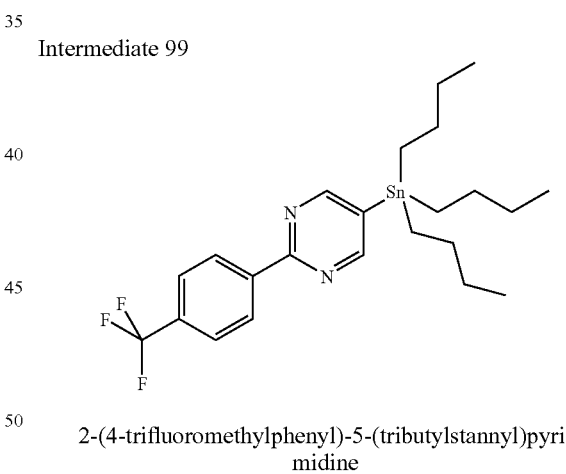

2-(4-trifluoromethylphenyl)-5-(tributylstannyl)pyrimidine n-BuLi 2.0M (ALDRICH, 0.18 ml) was added dropwise, with vigorous stirring, to a solution of 5-bromo-2-(4-trifluoromethylphenyl)pyrimidine (60 mg) in THF (2 ml) at −78° C. After stirring for 1 hour, tributyltin chloride (97 μl) was added dropwise at −78° C., under argon atmosphere. After 1 hour 30 minutes at −78° C., the reaction was quenched with 1 N NH4Cl (5 ml), diluted, extracted with ethyl acetate (3×10 ml), washed with brine, dried over MgSO4, concentrated under vacuum and purified by chromatography column using CH$_2$Cl$_2$-hexane 1:8 as eluent to give 75 mg of the desired product as a colorless oil.

$^1$H NMR (300 MHz, ClCD3) δ ppm; 8.81 (s, 2H), 8.56 (d, 2H), 7.74 (d, 2H), 1.70-1.52 (m, 6H), 1.42-1.25 (m, 8H), 0.95-0.88 (m, 9H).

Example 1

5-Bromo-2,6-dimethyl-6'-{[4-(trifluoromethoxy)benzyl]oxy}-3,3'-bipyridin-4(1H)-one

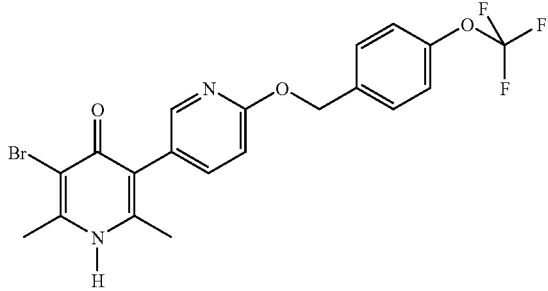

To a solution of Intermediate 27 (0.211 g) in a mixture dichloromethane/methanol v/v 2:1 (30 ml) was added portionwise N-bromosuccinimide (0.106 g). The mixture was stirred at room temperature under inert atmosphere for 1 h. Removal of the solvent under vacuum gave a crude white powder which was triturated with acetonitrile (20 ml) and filtered. The solid obtained was washed with acetonitrile, then dried under vacuum to afford 0.217 g of the title compound as a white powder.

$^1$H-NMR (δ, ppm, DMSO-$d_6$): 11.15 (bs, 1H); 7.97 (bd, 1H); 7.62-7.55 (m, 3H); 7.37 (d, 2H); 6.90 (d, 1H); 5.39 (s, 2H); 2.41 (s, 3H); 2.1 (s, 3H); [ES MS] m/z 470 (MH+)

Examples 2-7 were prepared by methods analogous to that described for Example 1 replacing Intermediate 27 with the Intermediate shown in Table 9.

TABLE 9

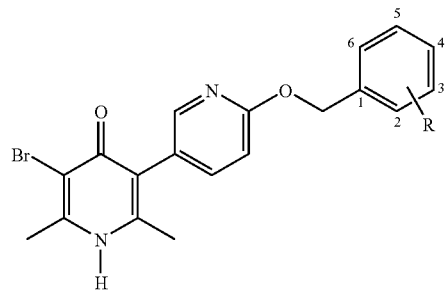

| Ex. | R | Starting Intermediate | Chemical name | Physical Data |
|---|---|---|---|---|
| 2 | 3-CF$_3$ | 28 | 5-Bromo-2,6-dimethyl-6'-{[3-(trifluoromethyl)benzyl]oxy}-3,3'-bipyridin-4(1H)-one | $^1$H-NMR (δ, ppm, CDCl$_3$): 7.93 (d, 1 H); 7.70 (s, 1 H); 7.60 (m, 1 H); 7.57-7.43 (m, 3 H); 6.83 (d, 1 H); 5.38 (s, 2 H); 2.40 (s, 3 H); 2.08 (s, 3 H). [ES MS] m/z 454 (MH$^+$), 452 (MH$^-$) |
| 3 | 4-CF$_3$ | 29 | 5-Bromo-2,6-dimethyl-6'-{[4-(trifluoromethyl)benzyl]oxy}-3,3'-bipyridin-4(1H)-one | $^1$H-NMR (δ, ppm, DMSO-$d_6$): 11.68 (bs, 1 H); 7.96 (bs, 1 H); 7.76-7.65 (m, 4 H); 7.58 (d, 1 H); 6.94 (d, 1 H); 5.47 (s, 2 H); 2.41 (s, 3 H); 2.10 (s, 3 H). [ES MS] m/z 454 (MH$^+$), 452 (MH$^-$) |
| 4 | 2-CF$_3$ | 30 | 5-Bromo-2,6-dimethyl-6'-{[2-(trifluoromethyl)benzyl]oxy}-3,3'-bipyridin-4(1H)-one | $^1$H-NMR (δ, ppm, DMSO-$d_6$): 11.68 (bs, 1 H); 7.96 (bs, 1 H); 7.80-7.71 (m, 3 H); 7.60-7.55 (m, 2 H); 6.92 (d, 1 H); 5.52 (s, 2 H); 2.42 (s, 3 H); 2.11 (s, 3 H). [ES MS] m/z 454 (MH$^+$), 452 (MH$^-$) |

TABLE 9-continued

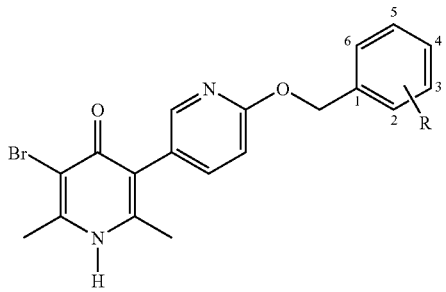

| Ex. | R | Starting Intermediate | Chemical name | Physical Data |
|---|---|---|---|---|
| 5 | 3,5-diCF$_3$ | 31 | 5-Bromo-2,6-dimethyl-6'-{[3,5-bis(trifluoromethyl)benzyl]oxy}-3,3'-bipyridin-4(1H)-one | $^1$H-NMR (δ, ppm, DMSO-d$_6$): 11.70 (bs, 1 H); 8.18 (s, 2 H); 8.07 (s, 1 H); 7.98 (d, 1 H); 7.59 (d, 1 H); 6.98 (d, 1 H); 5.55 (s, 2 H); 2.41 (s, 3 H); 2.10 (s, 3 H). [ES MS] m/z 522 (MH$^+$) |
| 6 | 4-F | 32 | 5-Bromo-6'-{[4-fluorobenzyl]oxy}-2,6-dimethyl-3,3'-bipyridin-4(1H)-one | $^1$H-NMR (δ, ppm, DMSO-d$_6$): 11.68 (bs, 1 H); 7.97 (s, 1 H); 7.57-7.49 (m, 3 H); 7.23-7.17 (m, 2 H); 6.87 (d, 1 H); 5.34 (s, 2 H); 2.41 (s, 3 H); 2.10 (s, 3 H). [ES MS] m/z 404 (MH$^+$), 402 (MH$^-$) |
| 7 | 3,5-diF | 33 | 5-Bromo-6'-{[3,5-difluorobenzyl]oxy}-2,6-dimethyl-3,3'-bipyridin-4(1H)-one | $^1$H-NMR (δ, ppm, DMSO-d$_6$): 11.69 (bs, 1 H); 7.96 (d, 1 H); 7.58 (d, 1 H); 7.19-7.14 (m, 3 H); 6.95 (d, 1 H); 5.39 (s, 2 H); 2.41 (s, 3 H); 2.10 (s, 3 H). [ES MS] m/z 422 (MH$^+$) |

Example 8

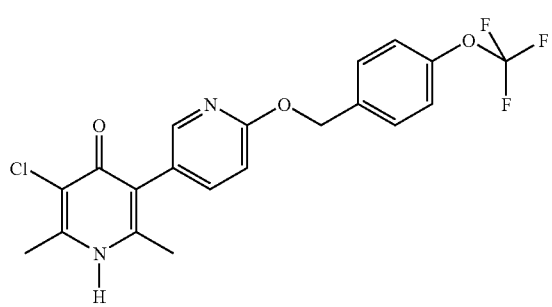

5-Chloro-2,6-dimethyl-6'-{[4-(trifluoromethoxy)benzyl]oxy}-3,3'-bipyridin-4(1H)-one To a cooled solution (0-4° C., ice/water bath) of Intermediate 27 (0.276 g) in a mixture dichloromethane/methanol v/v 2:1 (24 ml) was added portionwise under inert atmosphere trichloroisocyanuric acid (ALDRICH, 67 mg). The mixture was stirred at low temperature under inert atmosphere for 1.5 h, then diluted with a mixture dichloromethane/methanol v/v 2:1 (30 ml) and the cyanuric acid precipitated filtered. The filtrate was concentrated to dryness under vacuum to afford a solid residue which was suspended in a mixture of aqueous 0.5N NaOH (30 ml) and methanol (10 ml). After stirring for 1 h, the mixture was diluted by adding water (20 ml) and the remaining precipitate was filtered and washed successively with water (3×10 ml), mixture methanol/water v/v 1:1 (2×10 ml) and acetonitrile (3×10 ml). 0.193 g of the title compound were obtained as a white powder after drying under vacuum.

$^1$H-NMR (δ, ppm, DMSO-d$_6$): 11.65 (bs, 1H); 7.98 (bd, 1H); 7.61-7.55 (m, 3H); 7.38 (d, 2H); 6.91 (d, 1H); 5.39 (s, 2H); 2.37 (s, 3H); 2.11 (s, 3H); [ES MS] m/z 425 (MH+)

Examples 9-14 were prepared by methods analogous to that described for Example 8, replacing Intermediate 27 with the Intermediate shown in Table 10.

TABLE 10

| Ex. | R | Starting Intermediate | Chemical name | Physical Data |
|---|---|---|---|---|
| 9 | 3-CF$_3$ | 28 | 5-Chloro-2,6-dimethyl-6'-{[3-(trifluoromethyl)benzyl]oxy}-3,3'-bipyridin-4(1H)-one | $^1$H-NMR (δ, ppm, DMSO-d$_6$): 11.64 (bs, 1 H); 7.96 (d, 1 H); 7.82 (s, 1 H); 7.77 (m, 1 H); 7.70-7.55 (m, 3 H); 6.93 (d, 1 H); 5.46 (s, 2 H); 2.36 (s, 3 H); 2.09 (s, 3 H). [ES MS] m/z 407 (MH$^-$) |
| 10 | 4-CF$_3$ | 29 | 5-Chloro-2,6-dimethyl-6'-{[4-(trifluoromethyl)benzyl]oxy}-3,3'-bipyridin-4(1H)-one | $^1$H-NMR (δ, ppm, DMSO-d$_6$): 11.65 (bs, 1 H); 7.96 (s, 1 H); 7.76-7.66 (m, 4 H); 7.58 (d, 1 H); 6.93 (d, 1 H); 5.47 (s, 2 H); 2.37 (s, 3 H); 2.11 (s, 3 H). [ES MS] m/z 409 (MH$^+$) |
| 11 | 2-CF$_3$ | 30 | 5-Chloro-2,6-dimethyl-6'-{[2-(trifluoromethyl)benzyl]oxy}-3,3'-bipyridin-4(1H)-one | $^1$H-NMR (δ, ppm, DMSO-d$_6$): 11.64 (bs, 1 H); 7.96 (s, 1 H); 7.80-7.72 (m, 3 H); 7.60-7.54 (m, 2 H); 6.93 (d, 1 H); 5.52 (s, 2 H); 2.37 (s, 3 H); 2.11 (s, 3 H). [ES MS] m/z 409 (MH$^+$) |
| 12 | 3,5-diCF$_3$ | 31 | 5-Chloro-2,6-dimethyl-6'-{[3,5-bis(trifluoromethyl)benzyl]oxy}-3,3'-bipyridin-4(1H)-one | $^1$H-NMR (δ, ppm, DMSO-d$_6$): 11.66 (bs, 1 H); 8.18 (s, 2 H); 8.07 (s, 1 H); 7.98 (d, 1 H); 7.59 (d, 1 H); 6.98 (d, 1 H); 5.55 (s, 2 H); 2.37 (s, 3 H); 2.10 (s, 3 H). [ES MS] m/z 477 (MH$^+$), 475 (MH$^-$) |
| 13 | 4-F | 32 | 5-Chloro-6'-{[4-fluorobenzyl]oxy}-2,6-dimethyl-3,3'-bipyridin-4(1H)-one | $^1$H-NMR (δ, ppm, DMSO-d$_6$): 11.65 (bs, 1 H); 7.97 (s, 1 H); 7.57-7.50 (m, 3 H); 7.23-7.17 (m, 2 H); 6.89 (d, 1 H); 5.34 (s, 2 H); 2.37 (s, 3 H); 2.11 (s, 3 H). [ES MS] m/z 359 (MH$^+$) |
| 14 | 3,5-diF | 33 | 5-Chloro-6'-{[3,5-difluorobenzyl]oxy}-2,6-dimethyl-3,3'-bipyridin-4(1H)-one | $^1$H-NMR (δ, ppm, DMSO-d$_6$): 11.63 (bs, 1 H); 7.96 (s, 1 H); 7.58 (d, 1 H); 7.21-7.14 (m, 3 H); 6.94 (d, 1 H); 5.38 (s, 2 H); 2.37 (s, 3 H); 2.10 (s, 3 H). [ES MS] m/z 377 (MH$^+$), 375 (MH$^-$) |

Example 15

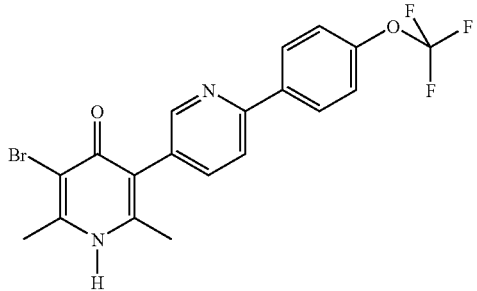

5-Bromo-2,6-dimethyl-6'-{4-[(trifluoromethyl)oxy]phenyl}-3,3'-bipyridin-4(1H)-one To a solution of Intermediate 34 (0.064 g) in a mixture of dichloromethane/methanol v/v 1:1 (2 ml) was added portionwise at room temperature N-bromosuccinimide (0.026 g). The suspension was stirred at room temperature for 30 min, then concentrated to dryness under vacuum. The residue thus obtained was triturated with ethyl acetate and filtered. The solid was washed with ethyl acetate and dried under vacuum. 0.062 g of the title compound were obtained as a white powder.

$^1$H-NMR (δ, ppm, DMSO-$d_6$): 11.7-11.6 (bs, 1H); 8.49 (m, 1H); 8.27-8.22 (m, 2H); 8.03 (d, 1H); 7.75 (dd, 1H); 7.48 (m, 2H); 2.44 (s, 3H); 2.15 (s, 3H); [ES MS] m/z 439 (MH+)

Examples 16-26 were prepared by methods analogous to that described for Example 15, replacing Intermediate 34 with the Intermediate indicated in Table 11.

TABLE 11

| Ex. | R | Starting Intermediate | Chemical name | Physical Data |
|---|---|---|---|---|
| 16 | 4-CF$_3$ | 37 | 5-Bromo-2,6-dimethyl-6'-{4-[trifluoromethyl]phenyl}-3,3'-bipyridin-4(1H)-one | $^1$H-NMR (δ, ppm, DMSO-$d_6$): 11.79 (s, 1 H), 8.54 (s, 1 H), 8.34 (d, 2 H), 8.10 (d, 1 H), 7.85 (d, 2 H), 7.79 (d, 1 H), 2.44 (s, 3 H), 2.16 (s, 3 H); [ES MS] m/z 423 (MH+) |
| 17 | 3-CF$_3$ | 38 | 5-Bromo-2,6-dimethyl-6'-{3-[trifluoromethyl]phenyl}-3,3'-bipyridin-4(1H)-one | $^1$H-NMR (δ, ppm, DMSO-$d_6$): 11.75 (s, 1 H), 8.53 (d, 1 H), 8.46 (s, 1 H), 8.42 (d, 1 H), 8.14 (d, 1 H), 7.82-7.72 (m, 3 H), 2.44 (s, 3 H), 2.16 (s, 3 H); [ES MS] m/z 421 (MH−) |
| 18 | 2-CF$_3$ | 39 | 5-Bromo-2,6-dimethyl-6'-{2-[trifluoromethyl]phenyl}-3,3'-bipyridin-4(1H)-one | $^1$H-NMR (δ, ppm, DMSO-$d_6$): 11.78 (s, 1 H), 8.46 (d, 1 H), 7.88-7.50 (m, 6 H), 2.44 (s, 3 H), 2.15 (s, 3 H); [ES MS] m/z 423 (MH+) |
| 19 | 4-Cl | 40 | 5-Bromo-6'-(4-chlorophenyl)-2,6-dimethyl-3,3'-bipyridin-4(1H)-one | $^1$H-NMR (δ, ppm, DMSO-$d_6$): 8.48 (s, 1 H), 8.15 (d, 2 H), 8.01 (d, 1 H), 7.74 (dd, 1 H), 7.55 (d, 2 H), 2.44 (s, 3 H), 2.15 (s, 3 H); [ES MS] m/z 389 (MH+) |
| 20 | 3-Cl | 41 | 5-Bromo-6'-(3-chlorophenyl)-2,6-dimethyl-3,3'-bipyridin-4(1H)-one | $^1$H-NMR (δ, ppm, DMSO-$d_6$): 11.77 (s, 1 H), 8.50 (d, 1 H), 8.18-8.04 (m, 3 H), 7.75 (dd, 1 H), 7.56-7.50 (m, 2 H), 2.44 (s, 3 H), 2.15 (s, 3 H); [ES MS] m/z 387 (MH+) |
| 21 | 2-Cl | 42 | 5-Bromo-6'-(2-chlorophenyl)-2,6-dimethyl-3,3'-bipyridin-4(1H)-one | $^1$H-NMR (δ, ppm, DMSO-$d_6$): 11.78 (s, 1 H), 8.50 (s, 1 H), 7.77-7.69 (m, 2 H), 7.66-7.57 (m, 2 H), 7.48-7.45 (m, 2 H), 2.44 (s, 3 H), |

TABLE 11-continued

| Ex. | R | Starting Intermediate | Chemical name | Physical Data |
|---|---|---|---|---|
| 22 | 4-F | 43 | 5-Bromo-6'-(4-fluorophenyl)-2,6-dimethyl-3,3'-bipyridin-4(1H)-one | 2.16 (s, 3 H); [ES MS] m/z 389 (MH+) $^1$H-NMR (δ, ppm, DMSO-$d_6$): 11.76 (s, 1 H), 8.47 (m, 1 H), 8.17 (m, 2 H), 7.97 (d, 1 H), 7.72 (dd, 1 H), 7.35-7.29 (m, 2 H), 2.44 (s, 3 H), 2.15 (s, 3 H); [ES MS] m/z 371 (MH−) |
| 23 | 2-F | 44 | 5-Bromo-6'-(2-fluorophenyl)-2,6-dimethyl-3,3'-bipyridin-4(1H)-one | $^1$H-NMR (δ, ppm, DMSO-$d_6$): 11.77 (s, 1 H), 8.52 (d, 1 H), 7.98 (td, 1 H), 7.82 (dd, 1 H), 7.75 (dd, 1 H), 7.53-7.45 (m, 1 H), 7.38-7.31 (m, 2 H), 2.44 (s, 3 H), 2.16 (s, 3 H); [ES MS] m/z 373 (MH+) |
| 24 | 2,4-di-CF$_3$ | 45 | 5-Bromo-2,6-dimethyl-6'-{2,4-bis[trifluoromethyl]phenyl}-3,3'-bipyridin-4(1H)-one | $^1$H-NMR (δ, ppm, DMSO-$d_6$): 11.80 (s, 1 H), 8.50 (d, 1 H), 8.19 (bs, 2 H), 7.86 (d, 1 H), 7.81 (dd, 1 H), 7.60 (d, 1 H), 2.45 (s, 3 H), 2.15 (s, 3 H); [ES MS] m/z 489 (MH−) |
| 25 | 3,5-di-CF$_3$ | 46 | 5-Bromo-2,6-dimethyl-6'-{3,5-bis[trifluoromethyl]phenyl}-3,3'-bipyridin-4(1H)-one | $^1$H-NMR (δ, ppm, CD$_3$OD): 8.66 (s, 2 H), 8.59 (d, 1 H), 8.13 (d, 1 H), 8.03 (bs, 1 H), 7.86 (dd, 1 H), 2.57 (s, 3 H), 2.26 (s, 3 H); [ES MS] m/z 489 (MH−) |
| 26 | n-C$_4$H$_9$— | 46 | 5-Bromo-6'-(4-n-butylphenyl)-2,6-dimethyl-3,3'-bipyridin-4(1H)-one | $^1$H-NMR (δ, ppm, DMSO-$d_6$): 11.75 (bs, 1 H), 8.45 (d, 1 H), 8.02 (d, 2 H), 7.93 (d, 1 H), 7.69 (d, 1 H), 7.31 (d, 2 H), 2.66 (m, 2 H); 2.44 (s, 3 H), 2.15 (s, 3 H); 1.64-1.27 (m, 4 H); 0.91 (t, 3 H); [ES MS] m/z 411 (MH+) |

Example 27

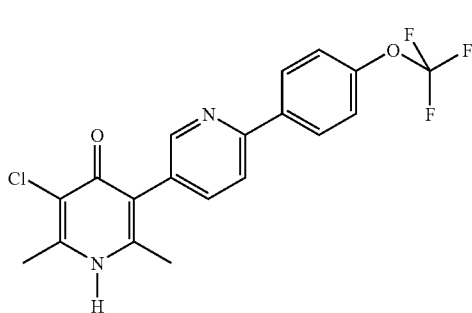

5-Chloro-2,6-dimethyl-6'-{4-[(trifluoromethyl)oxy]phenyl}-3,3'-bipyridin-4(1H)-one To a cooled solution (0-4° C., ice/water bath) of Intermediate 34 (1.39 g) in a mixture of dichloromethane/methanol v/v 2:1 (120 ml) was added portionwise at room temperature trichloroisocyanuric acid (0.365 g) and stirring continued for 1 h. The mixture was filtered and the precipitate washed with a mixture dichloromethane/methanol v/v 2:1. The filtrate was concentrated to dryness and the solid thus obtained suspended in aqueous 0.5N NaOH (60 ml) to which was added methanol (20 ml). Water (140 ml) was added with stirring and the precipitate formed was isolated by filtration. The solid was washed successively with water (3×20 ml) and acetonitrile (3×20 ml). 1.1 g of the title compound were obtained as a white powder after drying under vacuum.

$^1$H-NMR (δ, ppm, DMSO-d$_6$): 11.7-11.6 (bs, 1H); 8.50 (m, 1H); 8.24 (m, 2H); 8.02 (d, 1H); 7.75 (m, 1H); 7.48 (m, 2H); 2.39 (s, 3H); 2.15 (s, 3H); [ES MS] m/z 393 (MH+)

Examples 28-37 were prepared by methods analogous to that described for Example 27, replacing Intermediate 34 with the Intermediate shown in Table 12.

TABLE 12

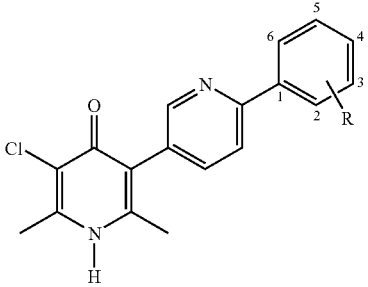

| Ex. | R | Starting Intermediate | Chemical name | Physical Data |
|---|---|---|---|---|
| 28 | 3-OCF$_3$ | 35 | 5-Chloro-2,6-dimethyl-6'-{3-[(trifluoromethyl)oxy]phenyl}-3,3'-bipyridin-4(1H)-one | $^1$H-NMR (δ, ppm, DMSO-d$_6$): 8.51 (s, 1 H), 8.17-8.07 (m, 3 H), 7.75 (dd, 1 H), 7.67-7.61 (m, 1 H), 7.43 (d, 1 H), 2.39 (s, 3 H), 2.16 (s, 3 H); [ES MS] m/z 393 (MH−) |
| 29 | 2-OCF$_3$ | 36 | 5-Chloro-2,6-dimethyl-6'-{2-[(trifluoromethyl)oxy]phenyl}-3,3'-bipyridin-4(1H)-one | $^1$H-NMR (δ, ppm, DMSO-d$_6$): 8.47 (s, 1 H), 7.88-7.85 (m, 1 H), 7.69-7.49 (m, 5 H), 2.22 (s, 3 H), 2.00 (s, 3 H); [ES MS] m/z 395 (MH+) |
| 30 | 4-CF$_3$ | 37 | 5-Chloro-2,6-dimethyl-6'-{4-[trifluoromethyl]phenyl}-3,3'-bipyridin-4(1H)-one | $^1$H-NMR (δ, ppm, DMSO-d$_6$): 11.85 (bs, 1 H); 8.54 (m, 1 H), 8.33 (d, 2 H), 8.09 (d, 1 H), 7.86 (d, 2 H); 7.78 (m, 1 H); 2.39 (s, 3 H), 2.15 (s, 3 H); [ES MS] m/z 379 (MH+) |
| 31 | 3-CF$_3$ | 38 | 5-Chloro-2,6-dimethyl-6'-{3-[trifluoromethyl]phenyl}-3,3'-bipyridin-4(1H)-one | $^1$H-NMR (δ, ppm, DMSO-d$_6$): 11.77 (bs, 1 H); 8.53 (m, 1 H), 8.46-8.41 (m, 2 H), 8.14 (d, 1 H), 7.82-7.72 (m, 3 H); 2.40 (s, 3 H), 2.16 (s, 3 H); [ES MS] m/z 377 (MH−) |
| 32 | 2-CF$_3$ | 39 | 5-Chloro-2,6-dimethyl-6'-{2-[trifluoromethyl]phenyl}-3,3'-bipyridin-4(1H)-one | $^1$H-NMR (δ, ppm, DMSO-d$_6$): 11.8 (bs, 1 H); 8.45 (m, 1 H), 7.87-7.50 (m, 6 H); 2.39 (s, 3 H), 2.15 (s, 3 H); [ES MS] m/z 379 (MH+) |
| 33 | 4-Cl | 40 | 5-Chloro-6'-(4-chlorophenyl)-2,6-dimethyl-3,3'-bipyridin-4(1H)-one | $^1$H-NMR (δ, ppm, DMSO-d$_6$): 8.46 (s, 1 H), 8.13 (d, 2 H), 7.95 (d, 1 H), 7.70 (dd, 1 H), 7.53 (d, 2 H), 2.32 (s, 3 H), 2.08 (s, 3 H); [ES MS] m/z 343 (MH−) |

TABLE 12-continued

| Ex. | R | Starting Intermediate | Chemical name | Physical Data |
|---|---|---|---|---|
| 34 | 3-Cl | 41 | 5-Chloro-6'-(3-chlorophenyl)-2,6-dimethyl-3,3'-bipyridin-4(1H)-one | $^1$H-NMR (δ, ppm, DMSO-$d_6$): 11.74 (s, 1 H), 8.46 (s, 1 H), 8.13 (s, 1 H), 8.06-8.00 (m, 2 H), 7.71 (dd, 1 H), 7.51-7.44 (m, 2 H), 2.36 (s, 3 H), 2.12 (s, 3 H); [ES MS] m/z 345 (MH+) |
| 35 | 2-Cl | 42 | 5-Chloro-6'-(2-chlorophenyl)-2,6-dimethyl-3,3'-bipyridin-4(1H)-one | $^1$H-NMR (δ, ppm, DMSO-$d_6$): 8.44 (s, 1 H), 7.68-7.55 (m, 4 H), 7.45-7.41 (m, 2 H), 2.21 (s, 3 H), 2.00 (s, 3 H); [ES MS] m/z 343 (MH−) |
| 36 | 4-F | 43 | 5-Chloro-6'-(4-fluorophenyl)-2,6-dimethyl-3,3'-bipyridin-4(1H)-one | $^1$H-NMR (δ, ppm, DMSO-$d_6$): 12-10 (bs, 1 H); 8.45 (d, 1 H), 8.15 (m, 2 H); 7.95 (d, 1 H); 7.70 (dd, 1 H); 7.31 (m, 2 H); 2.36 (s, 3 H), 2.12 (s, 3 H); [ES MS] m/z 327 (MH−) |
| 37 | 2-F | 44 | 5-Chloro-6'-(2-fluorophenyl)-2,6-dimethyl-3,3'-bipyridin-4(1H)-one | $^1$H-NMR (δ, ppm, DMSO-$d_6$): 12-11 (bs, 1 H); 8.52 (m, 1 H), 7.98 (m, 1 H); 7.77 (m, 2 H); 7.47 (m, 1 H); 7.34 (m, 2 H); 2.37 (s, 3 H), 2.13 (s, 3 H); [ES MS] m/z 329 (MH+) |

Example 31

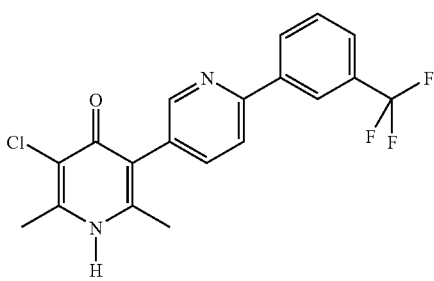

5-Chloro-2,6-dimethyl-6'-{3-[trifluoromethyl]phenyl}-3,3'-bipyridin-4(1H)-one

To a solution of Intermediate 38 (19.87 g) in 1200 ml of a mixture of dichloromethane/methanol v/v 2/1 was added portionwise at 0° C. powdered trichloroisocyanuric acid (ALDRICH, 5.48 g) over 40 minutes approx. After 1 h the mixture was diluted with 200 ml of the mixture dichloromethane/methanol v/v 2/1 and it was allowed to warm to 25° C. The solid precipitated was filtered under vacuum and washed twice with 50 ml of dichloromethane/methanol v/v 2/1.

The solution thus obtained was concentrated under vacuum and the resulting slurry treated with 0.5N NaOH (200 ml), then diluted with water (600 ml) with vigorous stirring. The suspension was stirred for 30 minutes, then filtered under vacuum. The solid thus obtained was washed successively with water (2×150 ml), mixture methanol/water v/v 2/1 (80 ml) and twice with acetonitrile (80+20 ml), then dried in the vacuum oven. 15.2 g of the title compound were obtained as an off-white powder.

$^1$H-NMR (δ, ppm, DMSO-d$_6$): 11.77 (bs, 1H); 8.53 (m, 1H), 8.46-8.41 (m, 2H), 8.14 (d, 1H), 7.82-7.72 (m, 3H); 2.40 (s, 3H), 2.16 (s, 3H); [ES MS] m/z 377 (MH−)

Example 38

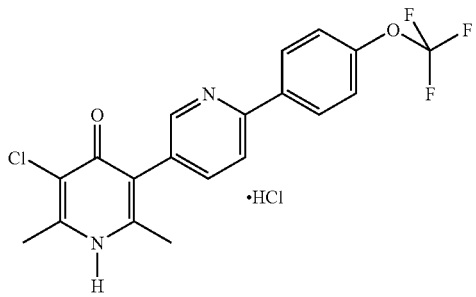

5-Chloro-2,6-dimethyl-6'-{4-[(trifluoromethyl)oxy]phenyl}-3,3'-bipyridin-4(1H)-one. Hydrochloride salt To a suspension of Example 27 (0.3 g) in methanol (15 ml) was added 2N HCl (1.5 ml). The solution thus obtained was stirred for 20 minutes, then concentrated to dryness to afford the title compound as a white powder.

$^1$H-NMR (δ, ppm, DMSO-d$_6$): 12.23 (bs, 1H); 8.6 (m, 1H); 8.24 (m, 2H); 8.13 (d, 1H); 7.95 (m, 1H); 7.55 (m, 2H); 2.44 (s, 3H); 2.21 (s, 3H) $^1$H-NMR (δ, ppm, CD$_3$OD): 8.9 (m, 1H); 8.60 (dd, 2H); 8.45 (d, 1H); 8.15 (m, 2H); 7.62 (m, 2H); 2.65 (s, 3H); 2.44 (s, 3H)

Example 39

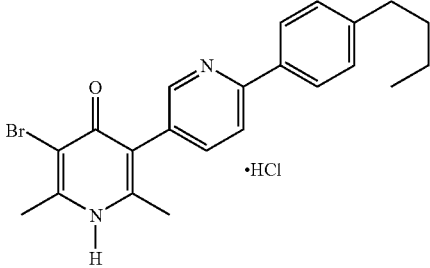

5-Bromo-6'-(4-n-butylphenyl)-2,6-dimethyl-3,3'-bipyridin-4(1H)-one Hydrochloride salt To a suspension of Example 26 (0.038 g) in methanol (1 ml) was added 1N HCl (0.276 ml). The solution thus obtained was stirred for 20 minutes, then concentrated to dryness to afford the title compound as a white powder.

$^1$H-NMR (δ, ppm, DMSO-d$_6$): 12.15 (bs, 1H); 8.61 (d, 1H); 8.20 (d, 1H); 8.13 (bs, 1H); 8.02 (d, 2H); 7.42 (d, 2H); 2.67 (m, 2H); 2.47 (s, 3H); 2.22 (s, 3H); 1.60 (m, 2H); 1.33 (m, 2H); 0.91 (t, 3H)

Example 40

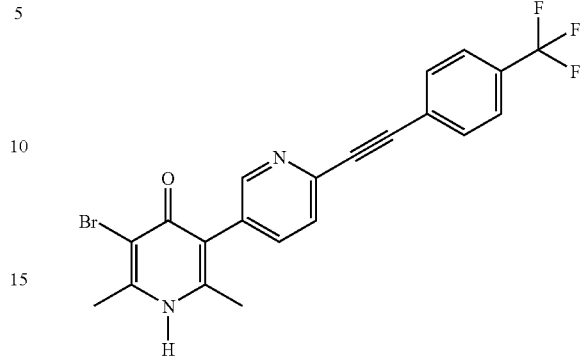

5-Bromo-2,6-dimethyl-6'-{[4-(trifluoromethyl)phenyl]ethynyl}-3,3'-bipyridin-4(1H)-one To a solution of Intermediate 52 (0.012 g) in a mixture of dichloromethane/methanol v/v 5:1 (6 ml) was added portionwise at room temperature N-bromosuccinimide (0.0064 g). The suspension was stirred at room temperature for 30 min, then concentrated to dryness under vacuum. The residue thus obtained was triturated with acetonitrile and filtered. The solid was washed with acetonitrile and dried under vacuum. 0.010 g of the title compound were obtained as a white powder.

$^1$H-NMR (δ, ppm, CD$_3$OD): 8.47 (m, 1H); 7.77 (m, 6H); 2.56 (s, 3H); 2.23 (s, 3H); [ES MS] m/z 447 (MH+)

Example 41

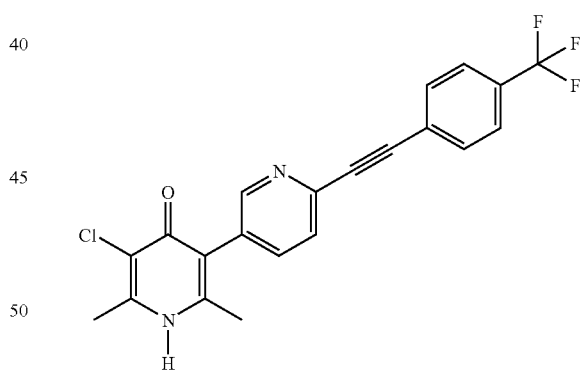

5-Chloro-2,6-dimethyl-6'-{[4-(trifluoromethyl)phenyl]ethynyl}-3,3'-bipyridin-4(1H)-one To a solution of Intermediate 52 (0.027 g) in a mixture of dichloromethane/methanol v/v 5:1 (6 ml) was added portionwise at room temperature trichloroisocyanuric acid (0.0068 g). The suspension was stirred at room temperature for 30 min, then concentrated to dryness under vacuum. The residue thus obtained was purified by preparative TLC chromatography, eluting with a mixture dichloromethane/5% methanol. 0.015 g of the title compound were obtained.

$^1$H-NMR (δ, ppm, CD$_3$OD): 8.47 (m, 1H); 7.77 (m, 6H); 2.51 (s, 3H); 2.23 (s, 3H); [ES MS] m/z 401 (MH+)

Example 42 was prepared by a method analogous to that described for Example 41, replacing Intermediate 52 with Intermediate 53, as shown in Table 13.

TABLE 13

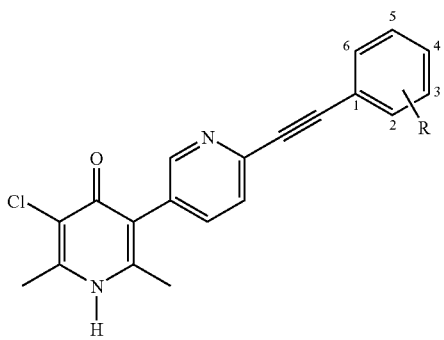

| Ex. | R | Starting Intermediate | Chemical name | Physical Data |
|---|---|---|---|---|
| 42 | 2,4-diF | 53 | 5-Chloro-6'-{[2,4-difluorophenyl]ethynyl}-2,6-dimethyl-3,3'-bipyridin-4(1H)-one | $^1$H-NMR ($\delta$, ppm, CD$_3$OD): 8.45 (m, 1 H); 7.80-7.68 (m, 3 H); 7.10 (m, 2 H); 2.51 (s, 3 H); 2.23 (m, 3 H) [ES MS] m/z 371 (MH$^+$) |

Example 43

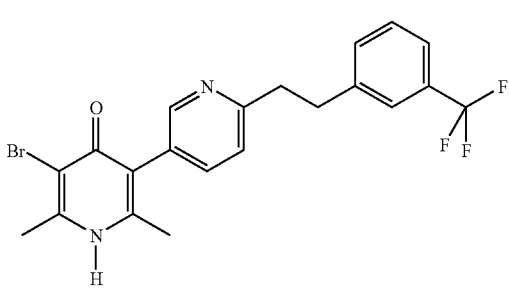

5-Bromo-2,6-dimethyl-6'-{2-[3-(trifluoromethyl)phenyl]ethyl}-3,3'-bipyridin-4(1H)-one To a solution of Intermediate 58 (0.020 g) in a mixture of dichloromethane (5 ml) and methanol (2 ml) was added portionwise N-bromosuccinimide. After 30 min of stirring the solvent was removed under vacuum and the resulting solid triturated with acetonitrile. 0.012 g of the title compound were obtained.

$^1$H-NMR ($\delta$, ppm, CD$_3$OD): 8.33 (m, 1H); 7.61 (dd, 1H); 7.47 (m, 4H); 7.30 (d, 1H); 3.14 (s, 4H); 2.55 (s, 3H); 2.17 (s, 3H); [ES MS] m/z 452 (MH+)

Example 44

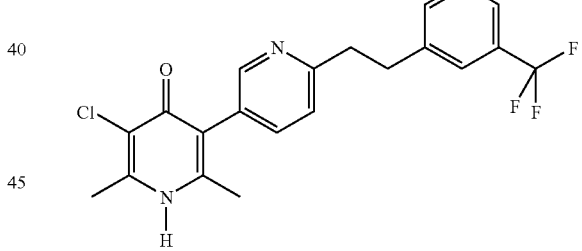

5-Chloro-2,6-dimethyl-6'-{2-[3-(trifluoromethyl)phenyl]ethyl}-3,3'-bipyridin-4(1H)-one To a solution of Intermediate 58 (0.038 g) in a mixture dichloromethane/methanol v/v 2:1 (6 ml) was added portionwise Trichloroisocyanuric acid. After 30 min of stirring at room temperature the solvent was removed under vacuum and the residue purified by preparative TLC chromatography, eluting with a mixture dichloromethane/10% methanol. 0.025 g of the title compound were obtained.

$^1$H-NMR ($\delta$, ppm, CD$_3$OD): 8.33 (m, 1H); 7.60 (dd, 1H); 7.47 (m, 4H); 7.30 (d, 1H); 3.14 (s, 4H); 2.50 (s, 3H); 2.17 (s, 3H) [ES MS] m/z 407 (MH+)

Examples 45-47 were prepared by methods analogous to that described for Example 44, replacing Intermediate 48 with the Intermediate shown in Table 14.

TABLE 14

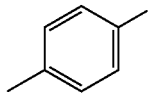

| Ex. | R | Starting Intermediate | Chemical name | Physical Data |
|---|---|---|---|---|
| 45 | [4-CF₃-phenyl-methyl group] | 57 | 5-Chloro-2,6-dimethyl-6'-{2-[4-(trifluoromethyl)phenyl]ethyl}-3,3'-bipyridin-4(1H)-one | $^1$H-NMR (δ, ppm, CD$_3$OD): 8.34 (m, 1 H); 7.60 (dd, 1 H); 7.47 (m, 2 H); 7.30 (d, 1 H); 3.14 (m, 4 H); 2.50 (s, 3 H); 2.17 (m, 3 H) [ES MS] m/z 405 (MH⁻) |
| 46 | [2,4-difluorophenyl-methyl group] | 60 | 5-Chloro-6'-{2-[2,4-difluorophenyl]ethyl}-2,6-dimethyl-3,3'-bipyridin-4(1H)-one | $^1$H-NMR (δ, ppm, CD$_3$OD): 8.32 (d, 1 H); 7.61 (dd, 1 H); 7.30-7.17 (m, 2 H); 6.86 (m, 2 H); 3.08 (m, 4 H); 2.51 (s, 3 H); 2.18 (m, 3 H) [ES MS] m/z 375 (MH⁺) |
| 47 | n-C₅H₁₁ | 56 | 5-Chloro-6'-(n-heptyl)-2,6-dimethyl-3,3'-bipyridin-4(1H)-one | $^1$H-NMR (δ, ppm, CD$_3$OD): 8.28 (d, 1 H); 7.64 (dd, 1 H); 7.37 (d, 1 H); 2.81 (m, 2 H); 2.50 (s, 3 H); 2.19 (s, 3 H); 1.74 (m, 2 H); 1.34 (m, 8 H), 0.90 (m, 3 H) [ES MS] m/z 331 (MH⁻) |

Example 48

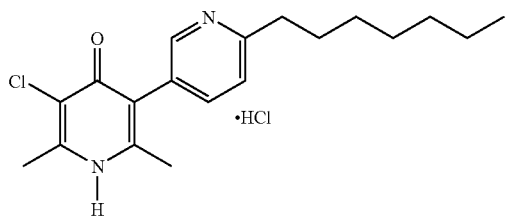

5-Chloro-6'-(n-heptyl)-2,6-dimethyl-3,3'-bipyridin-4(1H)-one

Hydrochloride salt.

Following the same experimental procedure to that described for Example 38, to a solution of Example 47 (0.044 g) in methanol (3 ml) was added 2N HCl (1 ml). The mixture was stirred for 20 minutes, then filtered and concentrated to dryness to afford 0.030 g of the title compound as a foam.

$^1$H-NMR (δ, ppm, CD$_3$OD): 8.78 (m, 1H); 8.50 (m, 2H); 8.08 (bd, 1H); 3.12 (m, 2H); 2.64 (s, 3H); 2.38 (s, 3H); 1.87 (m, 2H); 1.49-1.28 (m, 8H); 0.91 (m, 3H); [ES MS] m/z 331 (MH⁻)

Example 49

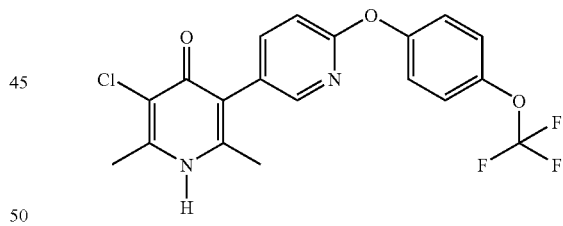

5-Chloro-2,6-dimethyl-6'-({4-[(trifluoromethyl)oxy]phenyl}oxy)-3,3'-bipyridin-4(1H)-one A mixture of Intermediate 63 (0.100 g), potassium carbonate (0.290 g), palladium acetate (0.008 g) and Intermediate 65 (0.211 g) in DMF (2 mL) was heated at 140° C., for 30 minutes under microwave irradiation. The reaction mixture was filtered through a pad of celite, evaporated under reduced pressure and purified by column chromatography on silica gel (eluent CH$_2$Cl$_2$/CH$_3$OH, 10:1). 0.087 g of the title product were obtained as a white solid $^1$H NMR (δ, ppm, DMSO-d$_6$): 11.69 (s, 1H), 7.95 (d, 1H), 7.72 (dd, 1H), 7.42 (d, 2H), 7.30 (d, 2H), 7.10 (d, 1H), 2.38 (s, 3H), 2.12 (s, 3H); [ES MS] m/z 411 (MH⁺)

Example 50

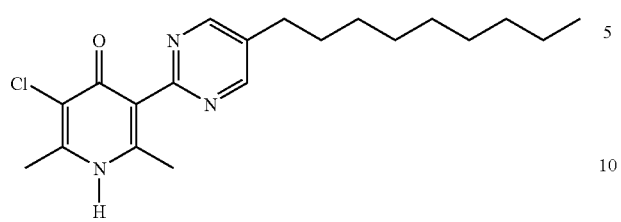

3-Chloro-2,6-dimethyl-5-(5-nonyl-2-pyrimidinyl)-4(1H)-pyridinone

A solution of Intermediate 63 (0.079 g), Intermediate 66 (0.032 g), tris(dibenzylideneacetone)dipalladium(0) (ALDRICH, 0.0052 g), tri-2-furylphosphine (ALDRICH, 0.0053 g) and copper (I) iodide (ALDRICH, 0.0022 g) in N-methyl-2-pyrrolidinone (1.1 ml) was degassed with nitrogen. The mixture was heated at 80° C. for 3 hours, then cooled to room temperature, treated with a saturated potassium fluoride (6 ml) and stirred for 20 minutes. The mixture was passed through a pad of celite with ethyl acetate. The organic layer was washed with NH$_4$Cl (3×20 ml), water (2×10 ml), dried over MgSO$_4$ and concentrated under vacuum to give a brown oil. The addition of diethyl ether afforded 0.0263 g of the title compound as a crude product, as a pink solid.

$^1$H NMR (δ, ppm, CD$_3$OD): δ 8.75 (s, 2H); 2.72 (t, 2H); 2.51 (s, 3H); 2.12 (s, 3H); 1.70 (m, 2H); 1.45-1.25 (m, 12H); 0.92-0.87 (m, 3H); [ES MS] m/z 362.20 (MH+), 360.18 (MH−).

Example 51

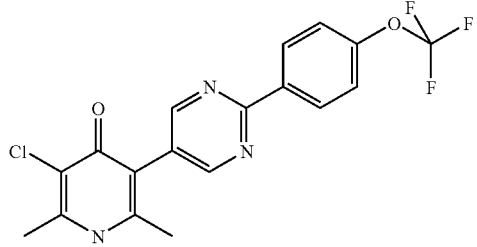

3-Chloro-2,6-dimethyl-5-{2-[4-(trifluoromethyloxy)phenyl]-5-pyrimidinyl}-4(1H)-pyridinone A solution of N-methyl-2-pyrrolidinone (1.50 ml), Intermediate 68 (0.113 g), Intermediate 63 (0.0432 g), tris(dibenzylideneacetone)dipalladium (0) (ALDRICH, 0.007 g), tri-2-furylphosphine (ALDRICH, 0.0071 g) and copper (I) iodide (ALDRICH, 0.003 g) was degassed with nitrogen. The mixture was heated at 80° C. for 15 hours, then cooled to room temperature. Saturated potassium fluoride (8 ml) was added and the mixture stirred for 20 minutes. The mixture was passed through a pad of celite and washed with ethyl acetate. The organic layer was washed with NH$_4$Cl (2×15 ml), water (1×20 ml), dried over MgSO$_4$ and concentrated under vacuum to give a brown oil. The crude was purified by preparative HPLC to afford 8.6 mg of the title compound as a grey powder.

$^1$H-NMR (δ, ppm, CD$_3$OD): 8.77 (s, 2H), 8.56 (d, 2H), 7.41 (d, 2H), 2.52 (s, 3H), 2.30 (s, 3H). [ES MS] m/z 396.11 (MH+), 394.06 (MH−).

Example 52

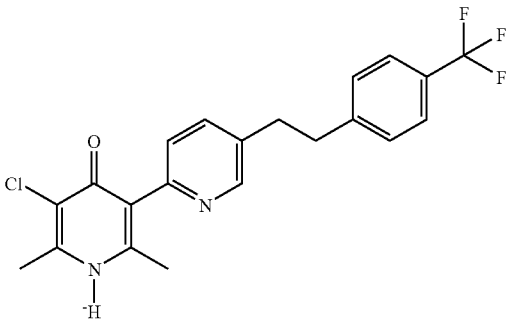

5'-Chloro-2',6'-dimethyl-5-{2-[4-(trifluoromethyl)phenyl]ethyl}-2,3'-bipyridin-4'(1'H)-one To a solution of Intermediate 74 (0.50 g), copper(I) iodide (0.012 g), 4-ethynyl-α,α,α-trifluorotoluene (ALDRICH, 0.04 ml), dichlorobis(triphenylphosphine)palladium(II) (0.008 g) and triphenylphosphine (0.0019 g) in dry DMF (2 ml) was added triethylamine (0.8 mL). After heating the mixture at 110° C. for 3 h, it was diluted with ethyl acetate, washed with 1N NH$_4$Cl and dried over Na$_2$SO$_4$. The crude was purified by column chromatography (eluent CH$_2$Cl$_2$/CH$_3$OH, 10:1) to yield 0.018 g of Intermediate 13, which was dissolved in MeOH (3 mL) and Palladium 10% w/w on activated charcoal (10 mg) was added. The mixture was shaken under 30 psi of hydrogen for 2 h. The catalyst was filtered through a pad of celite, the solvent evaporated to dryness and the crude purified by column chromatography (eluent CH$_2$Cl$_2$/CH$_3$OH, 10:1) to afford 0.010 g of the title compound.

$^1$H-NMR (δ, ppm, CD$_3$OD): 8.34 (d, 1H), 7.74 (dd, 1H), 7.55 (d, 2H), 7.39-7.35 (m, 3H), 3.07-3.04 (m, 4H), 2.50 (s, 3H), 2.11 (s, 3H); [ES MS] m/z 407.00 (MH+);

Example 53 was prepared by a method analogous to that described for Example 15, as indicated in Table 11a.

TABLE 11a

Example 53

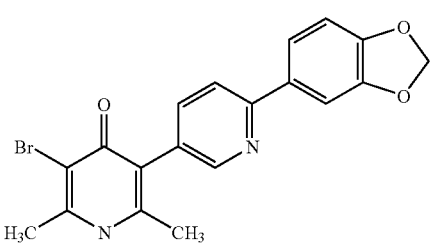

| Ex. | Starting Intermediate | Chemical name | Physical Data |
|---|---|---|---|
| 53 | 88 | 5-Bromo-2,6-dimethyl-3-(6-{[3,4-methylenedioxy]phenyl}-3,3'- | $^1$H NMR (δ, ppm, DMSO): 11.74 (s, 1 H), 8.40 (s, 1 H), 7.90 (d, 1 H), 7.68-7.64 (m, 3 H), 7.03 (d, 1 H), 6.08 (s, |

TABLE 11a-continued

Example 53

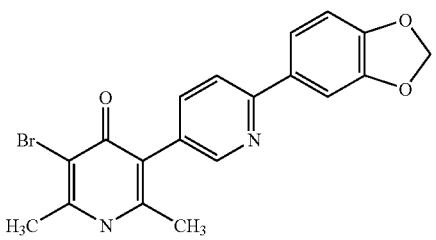

| Ex. | Starting Intermediate | Chemical name | Physical Data |
|---|---|---|---|
| | | bipyridin-4(1H)-one | 2 H), 2.43 (s, 3 H), 2.14 (s, 3 H), [ES MS] m/z 399.00 (MH+); |

Examples 54-63 were prepared by methods analogous to that described for Example 27, replacing Intermediate 34 with the Intermediate shown in Tables 12a and 12b.

TABLE 12a

Example 54

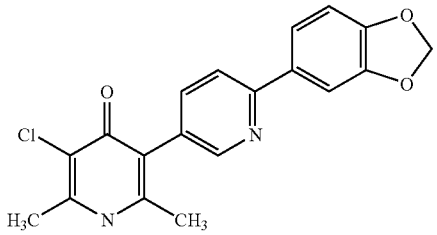

| Ex. | Starting Intermediate | Chemical name | Physical Data |
|---|---|---|---|
| 54 | 88 | 5-Chloro-2,6-dimethyl-3-(6-{[3,4-methylenedioxy]phenyl}-3,3'-bipyridin-4(1H)-one | $^1$H-NMR ($\delta$, ppm, DMSO-$d_6$): 8.39 (dd, 1 H), 7.87 (d, 2 H), 7.66-7.62 (m, 3 H), 7.02 (d, 2 H), 6.08 (s, 2 H), 2.33 (s, 3 H), 2.10 (s, 3 H); [ES MS] m/z 355.11 (M + 1$^+$), 353.10 (M − 1$^+$) |

TABLE 12b

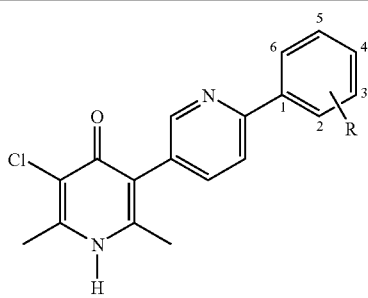

| Ex. | R | Starting Intermediate | Chemical name | Physical Data |
|---|---|---|---|---|
| 55 | 2-Cl,4-CF$_3$ | 89 | 5-chloro-6'-[2-chloro-4-(trifluoromethyl)phenyl]-2,6-dimethyl-3,3'-bipyridin-4(1H)-one | $^1$H NMR ($\delta$, ppm, DMSO-$d_6$): 8.54 (s, 1 H), 8.01 (s, 2 H), 7.85-7.77 (m, 4 H), 2.36 (s, 3 H), 2.13 (s, 3 H), [ES MS] m/z 411.00 (M + 1$^+$) |
| 56 | 2-F,5-CF$_3$ | 90 | 5-chloro-6'-[2-fluoro-5-(trifluoromethyl)phenyl]-2,6-dimethyl-3,3'-bipyridin-4(1H)-one | $^1$H NMR ($\delta$, ppm, DMSO-$d_6$): 8.57 (s, 1 H), 8.35 (dd, 1 H), 7.87-7.78 (m, 4 H), 7.62 (t, 1 H), 2.37 (s, 3 H), 2.14 (s, 3 H), [ES MS]: 395.10 (M − 1$^+$) |
| 57 | 2-Cl,5-CF$_3$ | 91 | 5-chloro-6'-[2-chloro-5-(trifluoromethyl)phenyl]-2,6-dimethyl-3,3'-bipyridin-4(1H)-one | $^1$H NMR ($\delta$, ppm, DMSO-$d_6$): 8.54 (s, 1 H), 7.97 (s, 1 H), 7.84-7.80 (m, 4 H), 2.37 (s, 3 H), 2.14 (s, 3 H) [ES MS]: 411.00; |
| 58 | 2-F,4-CF$_3$ | 92 | 5-chloro-6'-[2-fluoro-4-(trifluoromethyl)phenyl]-2,6-dimethyl-3,3'-bipyridin-4(1H)-one | $^1$H NMR ($\delta$, ppm, DMSO): 11.79 (s, 1 H), 8.58 (s, 1 H), 8.21 (t, 1 H), 7.91-7.80 (m, 3 H), 7.73 (d, 1 H), 2.40 (s, 3 H), 2.17 (s, 3 H), [ES MS]: 395.10 |
| 59 | 4-O-$^n$Bu | 93 | 5-Chloro-2,6-dimethyl-6'-{[4-butyloxy]phenyl}-3,3'-bipyridin-4(1H)-one | $^1$H-NMR ($\delta$, ppm, DMSO-$d_6$): 8.40 (d, 1 H), 8.05 (d, 2 H), 7.88 (d, 1 H), 7.63 (dd, 1 H), 7.03 (d, 2 H), |

TABLE 12b-continued

| Ex. | R | Starting Intermediate | Chemical name | Physical Data |
|---|---|---|---|---|
| | | | | 4.03 (t, 2 H), 2.36 (s, 3 H), 2.12 (s, 3 H), 1.77-1.67 (m, 2 H), 1.51-1.39 (m, 2 H), 0.94 (t, 3 H); [ES MS] m/z 383.14 (M + 1⁺), 381.13 (M − 1⁺) |
| 60 | 3-Cl,4-O—ⁿPr | 94 | 5-Chloro-2,6-dimethyl-6'-{[3-chloro,4-propyloxy]phenyl}-3,3'-bipyridin-4(1H)-one | $^1$H-NMR (δ, ppm, DMSO-$d_6$): 8.42 (bs, 1 H), 8.17 (s, 1 H), 8.00 (m, 2 H), 7.66 (m, 1 H), 7.24 (d, 1 H), 4.09 (t, 2 H), 2.34 (s, 3 H), 2.10 (s, 3 H), 1.77 (m, 2 H), 1.02 (t, 3 H); [ES MS] m/z 403 (MH+) |
| 61 | 4-O—Pr$^i$ | 95 | 5-Chloro-2,6-dimethyl-6'-{[4-isopropyloxy]phenyl}-3,3'-bipyridin-4(1H)-one | $^1$H-NMR (δ, ppm, DMSO-$d_6$): 8.39 (bs, 1 H), 8.00 (d, 2 H), 7.84 (d, 1 H), 7.65 (d, 1 H), 7.00 (d, 2 H), 4.69 (m, 1 H), 2.34 (s, 3 H), 2.10 (s, 3 H), 1.30 (s, 3 H), 1.28 (s, 3 H); [ES MS] m/z 369 (MH+) |
| 62 | 4-O—CH$_2$CF$_3$ | 96 | 5-Chloro-2,6-dimethyl-6'-{4-[2,2,2-trifluoroethoxy]phenyl}-3,3'-bipyridin-4(1H)-one- | $^1$H-NMR (δ, ppm, DMSO-$d_6$): 8.44 (dd, 1 H), 7.97 (d, 2 H), 7.85 (dd, 1 H), 7.75 (dd, 1 H), 7.13 (d, 2 H), 4.58 (q, 2 H), 2.51 (s, 3 H), 2.24 (s, 3 H); [ES MS] m/z 409 [M + 1]⁺ |
| 63 | 4-CHF$_2$ | 97 | 5-Chloro-2,6-dimethyl-6'-{4-[difluoromethyl]phenyl}-3,3'-bipyridin-4(1H)-one | $^1$H-NMR (δ, ppm, DMSO-$d_6$): 11.74 (bs, 1 H), 8.52 (m, 1 H), 8.26 (d, 2 H), 8.06 (d, 1 H), 7.77 (dd, 1 H), 7.70 (d, 2 H), 7.10 (t, 1 H), 2.40 (s, 3 H), 2.17 (s, 3 H); [ES MS] m/z 361 [M + H]⁺ |

Example 64

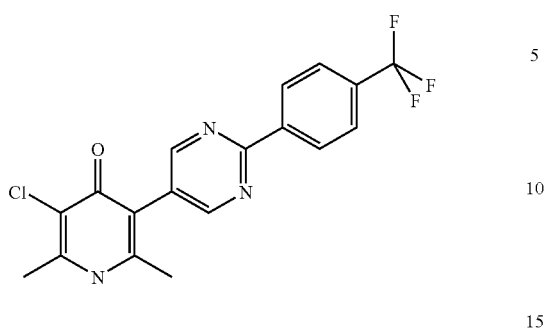

3-Chloro-2,6-dimethyl-5-(5-(2-(4-trifluoromethylphenyl))pyrimidinyl)pyridin-4(1H)-one A solution of N-methyl-2-pyrrolidinone (0.92 ml), 2-(4-trifluoromethylphenyl)-5-(tributylstannyl)pyrimidine (68 mg), 3-chloro-5-iodo-2,6-dimethylpyridin-4(1H)-one (27 mg), tris(dibenzylideneacetone)dipalladium(0) (ALDRICH, 4.3 mg), tri-2-furylphosphine (ALDRICH, 4.4 mg) and copper (I) iodide (ALDRICH, 1.8 mg) was degassed with nitrogen. The mixture was heated at 80° C. for 21 hours, then cooled to room temperature, treated with a saturated potassium fluoride (5 ml) and stirred for 20 minutes. The mixture was passed through a pad of celite with ethyl acetate. The organic layer was washed with $NH_4Cl$ (3×10 ml), water (2×10 ml), dried over $MgSO_4$ and concentrated under vacuum to give a brown oil. The crude was purified by preparative HPLC to afford 6.7 mg as a white solid.

$^1$H NMR (300 MHz, DMSO-d$^6$) δ ppm; 8.85 (s, 2H), 8.62 (d, 2H), 7.91 (d, 2H), 2.40 (s, 3H), 2.22 (s, 3H). [ES MS] m/z 380.09 (M+1$^+$), 378.08 (M-1$^+$).

Example 65

5-Bromo-2,6-dimethyl-6'-(phenyloxy)-3,3'-bipyridin-4(1H)one [ES MS] m/z=371, 373 (MH+)

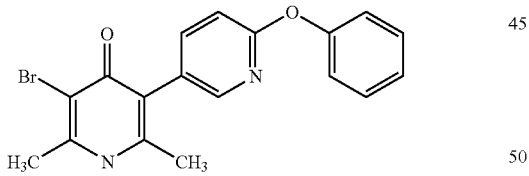

Example 66

5-Chloro-2,6-dimethyl-6'-(phenyloxy)-3,3'-bipyridin-4(1H)one [ES MS] m/z=325 (MH-)

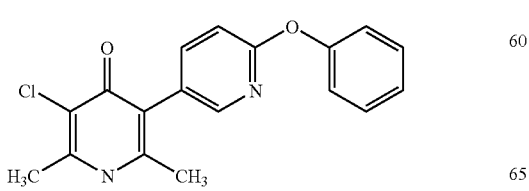

Example 67

5-Bromo-2,6-dimethyl-6'-phenyl-3,3'-bipyridin4(1H)one [ES MS] m/z=355, 357 (MH+)

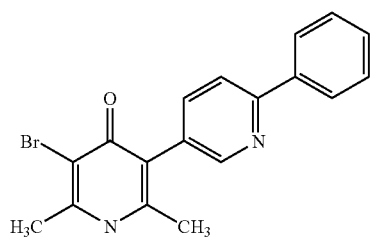

Example 68

5-Bromo-6'-[3-(hydroxymethyl)phenyl]-2,6-dimethyl-3,3'-bipyridin-4(1H)one [ES MS] m/z=383, 385 (MH-)

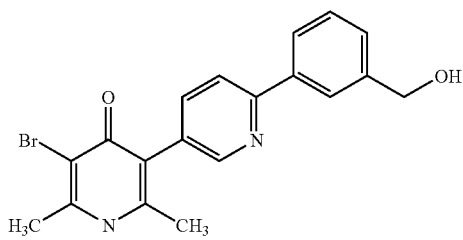

Example 69

5-Bromo-6'-[4-(cyano)phenyl]-2,6-dimethyl-3,3'-bipyridin-4(1H)one [ES MS] m/z=380, 382 (MH+)

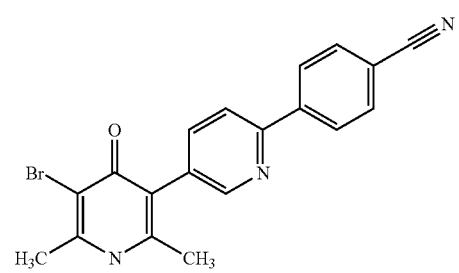

Example 70

5-Bromo-2,6-dimethyl-6'-[4-(methylsulphonyl)phenyl]-3,3'-bipyridin-4(1H)one [ES MS] m/z=431, 433 (MH−)

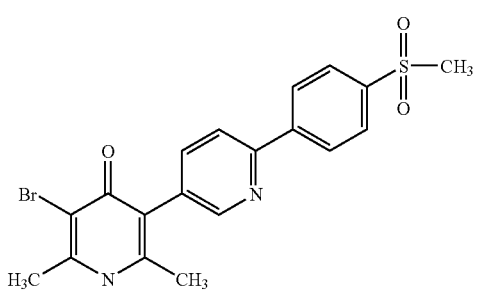

Example 71

5-Bromo-6'-[3-bromo-4-(dimethylamino)phenyl]-2,6-dimethyl-3,3'-bipyridin-4(1H)one [ES MS] m/z=476, 478, 480 (MH+)

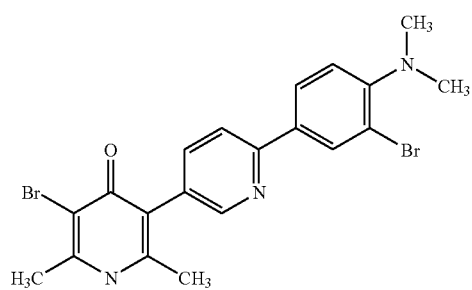

Example 72

5-Chloro-2,6-dimethyl-6'-[4-(methyloxy)phenyl]-3,3'-bipyridin-4(1H)one [ES MS] m/z=341 (MH+)

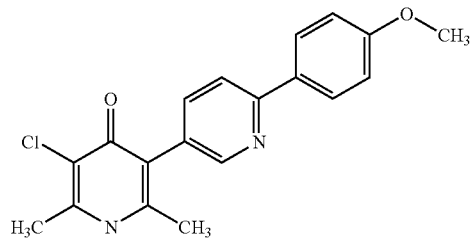

Example 73

5-Chloro-6'-[3-fluoro-4-(methyloxy)phenyl]-2,6-dimethyl-3,3'-bipyridin-4(1H)one [ES MS] m/z=359 (MH+)

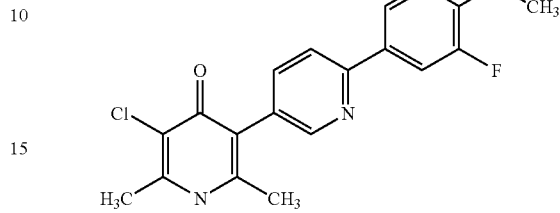

Biological Assays

The compounds of this invention may be tested in one of several biological assays to determine the concentration of compound which is required to have a given pharmacological effect.

In Vitro Anti-malarial Activity Against *Plasmodium falciparum*

IC$_{50}$ Assay/[$^3$H]-Hypoxanthine Assay

I. Materials

Parasite.
*Plasmodium falciparum* strains.

Culture Medium.

The culture medium comprised RPMI 1640 with 25 mM HEPES, sodium bicarbonate and glutamine (GIBCO™ cat. ref.: 52400), supplemented with 10% of pooled human sera AB (Irvine Scientific, cat. ref.: 5009) and HT supplement (0.15 mM hypoxanthine and 24 μM thymidine), (GIBCO™ cat. ref.: 41065). Human sera were decomplemented 30 min. at 56° C., aliquoted and stored frozen at −20° C. until use in this culture medium.

This culture medium ("complete medium") was usually prepared fresh just before use and pre-warmed to 37° C.

Red Blood Cells.

Red blood cells O+ stock suspensions were prepared from whole blood bags coming from incomplete blood donation, provided by the Spanish Red Cross (<25 days after sampling). This "whole blood" was aliquoted and stored at 4° C.

To prepare red blood cells for the assay, the whole blood was centrifuged and washed 3 times with RPMI without serum. The upper phase, containing white blood cells was removed. The washed red blood cells were kept as a 50% suspension in complete medium. The prepared cells were stored at 4° C. and were employed in the assay at any time up to 4 days after preparation.

II. Compounds

Compound Preparation

Test compounds were dissolved at 2 mg/ml in 100% DMSO on the day of the assay. If necessary, complete dissolution was achieved by gentle heating (the mixture was heated at a temperature <37° C.) and sonication (sonication bath).

Before test compounds were added to the parasites, the percentage of DMSO in the compound solution was reduced by further dilutions of the solution with culture medium prepared in the same way as described above for complete medium, but which did not contain hypoxanthine. The final concentration of DMSO in the assay plates was not permitted to exceed 0.2%, so that it did not produce any detectable undesired effects on the development of the parasite. For $IC_{50}$ determinations, 10 serial 2-fold dilutions were prepared in complete medium in the presence of a constant amount of DMSO. Any obvious signs of insolubility of the stock solutions in 100% DMSO or precipitation when these solutions were diluted in assay media, were recorded.

III *Plasmodium falciparum* Culture (Parasite)

*Plasmodium falciparum* strains were maintained in complete medium at an hematocrit of 5% in continuous culture using a method adapted from Trager and Jensen (1, 2).

The parasitemia was calculated by counting the percentage of parasitized erythrocytes by optical microscopy. Thin films of blood were made every day from each culture flask, fixed with methanol and stained for 10 min. in Giemsa (Merck, cat ref.: 1.09204) at 10% in buffered water pH 7.2. The glass slides were observed and counted with an optical microscope (Nikon, Eclipse E200) equipped with a 100× immersion oil objective.

The culture was maintained at an hematocrit of 5%, with a daily change of medium and was diluted when parasitemia had reached about 5%. The parasite population was asynchronous, composed of a stable proportion (≅70%) of young trophozoites (ring forms) and showed a regular rate of growth of 3 to 3.5 times the initial number of parasites daily.

Growth was achieved in culture flasks (canted neck, Corning) incubated at 37° C. under low oxygen atmosphere (5% $CO_2$, 5% $O_2$, 95% $N_2$).

IV. $IC_{50}$ Assay

[$^3$H] Hypoxanthine incorporation assay was conducted using a method adapted from Desjardins et al. (3). The assays were performed in 96 wells flat bottom microplates.

1. Serial dilutions of the test compounds (50 µl of a 5× solution/well) were deposited in duplicate. Compounds of the invention were tested in this assay. Chloroquine and Atovaquone were used as control compounds for each assay.

2. The inoculum was prepared as a suspension of parasitized red blood cells (PRBCs) at 2.5% of hematocrit and 0.5% of parasitemia in culture medium prepared in the same way as described above for complete medium, but which did not contain hypoxanthine.

3. [$^3$H]-Hypoxanthine (Amersham Biosciences, cat. ref.: TRK74) was added extemporaneously to the inoculum suspension at a concentration of 1 µCi/ml (equating to 0.25 µCi/well). 200 µl of the resulting suspension was distributed into each well (other than the control well H12 described below) leading to a final volume of 250 µl per well, at 2% of hematocrit and 0.5% of parasitemia/well.

4. In each plate, 2 columns were reserved for control wells:
  Column 11: Positive control wells: PRBCs with 0.2% DMSO—(i) to determine DMSO solvent effect on parasite growth (at a final concentration of 0.2%) and (ii) to compare with cultures treated with test compounds.
  Column 12 (comprising wells A12-H12):
    A12-D12—Background value wells: Uninfected RBCs—blank control to obtain the background reading from RBCs without parasites.
    E12-G12—Solvent effect wells: PRBCs without DMSO—to determine DMSO solvent effect on PRBCs by comparing these wells with column 11 wells.
    H12-Non-radioactive well: PRBCs with cold hypoxanthine—(i) to carry out a thin blood film to determine parasitemia value after incubation by microscopy and (ii) to ensure that the parasites have grown properly during the assay. (200 µl of inoculum suspension was prepared as described above (Items 2 and 3) but with non-tritiated hypoxanthine instead of [3H]-hypoxanthine, then added to this well to a final volume of 250 µl).

5. The plates were incubated for 48 hours at 37° C. under low oxygen atmosphere. At the end of the assay, a thin film was made with the non-radioactive sample (well H12) for a visual control of the development of the parasites. Incorporation was stopped by freezing the plates overnight at −80° C.

6. The growth was quantified by measuring the level of incorporation of [$^3$H]-hypoxanthine into the nucleic acids of the parasite. After thawing the plates, the content of the wells was harvested on glass fibre filters (Wallac, cat. ref.: 1450-421) with a semi-automated cell-harvester (Harvester 96, TOMTEC). The filters were dried and treated with a Melt-on scintillator (Meltilex® A, PerkinElmer cat. ref.: 1450-441). Incorporation of radioactivity was measured with a β-counter (Wallac Microbeta, PerkinElmer).

The assays were repeated at least three independent times.

V. Analysis of the Data

The value of each well was corrected by subtracting the background value from the absolute value. Background was calculated for each plate as the average value in cpm of the uninfected control wells.

For each concentration of a given test compound, the average (mean) value of the duplicate samples was calculated.

For each concentration of each test compound, the percentage of inhibition was then calculated by comparison with the value obtained from a control well containing PRBCs which was diluted with DMSO to achieve the same well volume but in the absence of test compound. The control well used here is the column 11 well described above (taking a mean value over all column 11 wells).

Analysis of the data were performed using Excel and GraphPad Prism 3.0 software. Results were expressed as the average ± standard deviation of at least 3 independent experiments performed on different days.

VI. Bibliography

1. Trager W, Jensen J B. Human malaria parasites in continuous culture. Science. 1976 Aug. 20; 193 (4254):673-5.
2. Trager W. Cultivation of malaria parasites. Methods Cell Biol. 1994; 45:7-26.
3. Desjardins R E, Canfield C J, Haynes J D, Chulay J D. Quantitative assessment of antimalarial activity in vitro by a semiautomated microdilution technique. Antimicrob Agents Chemother 1979 December; 16 (6):710-8.

Compound Solubility Determination

I. Materials

Compounds

An amount of 3 mg solid compound with LC-MS purity ≧95% was required. This amount was split between 3 different glass vials (1.8 ml volume each), placing 1 mg compound into each one.

Solvents and Buffers

Organic solvents of HPLC grade were used. Ultra pure water (Milli-Q grade) was used. Buffers were prepared with ultra pure water and filtered using 0.45µ cameo filters. The compositions of each solvent employed in this assay are described below (part III).

II. Procedures.

1. Procedure for Gross Solubility Determination:

a) 100 µl of solvent was added to each vial with a digital pipette (Eppendorf Research pro).
b) The mixture was subsequently subjected to vortexing for 1 min and sonicated for 5 minutes.
c) Steps a) and b) were repeated until a final volume of 1 ml was reached in each vial.
d) A microscope was used to examine the sample in each vial.
e) The solubility of the compound in each sample was calculated as < the final concentration after all of the sample has dissolved and > the concentration before the last solvent addition.
f) The solubility of the compound was calculated to be the mean value of the three vial samples.

2. Determination of Equilibrium Solubility (Assuming Chemical Stability in the Desired Solvent is not a Problem).

For each of the three vial samples prepared as described above, in which the amount of compound was totally dissolved, the following procedure was subsequently carried out:

a) A small amount (approx. 0.1 mg) of additional solid compound was added to the vial to maintain an excess of the compound in the mixture in the form of undissolved solid.
b) The samples were magnetically stirred for 24 hr. If required, additional solid compound (0.1 mg) was added to maintain excess of it and then the samples were stirred again.
c) Then the samples were filtered (Millipore Milex filters nylon 0.2 um) and three aliquots were taken (one from each of the three vials) and analysed by LC-MS.
d) The pH of the final solution in each sample was measured with a pH-meter (WTW pH330i and a pH-electrode Sentix 41).

3. LC-MS Assay for Analytical Quantification

All filtered aliquots were analysed by LC-MS. The analysis was carried out with a Luna 5 µC18 (2) column 4.6×150 mm, using a HP1100 HPLC instrument interfaced with a Waters ZMD-2000 MS spectrometer. The concentration of the final sample as prepared above was calculated from that of a reference calibration curve obtained from serial dilutions of a 2 mM solution of the compound under investigation in DMSO (Aldrich cat. ref.: 27685-5) stock solution.

4. Analysis of Data

The analysis of all LC-MS data was performed with MassLynx 3.4 software. Statistical and graphic analysis of data was performed using Microsoft Excel. The concentration (uM) and solubility (ug/ml) for each compound was calculated using the peak areas from the sample and those from the calibration curve.

III. Compositions of Solvents Used in these Assays.

A) FaSSIF is a solvent which simulates the Fasted State of the Intestinal Fluid. (FaSSIF: Fasted State Simulated Intestinal Fluid). Its composition is as given in the table below.

Composition of FaSSIF and the DH 6.8 Buffer Used in FaSSIF

| Composition of FaSSIF | | |
|---|---|---|
| | Conc. | Quantity per 100 ml |
| NaTaurochol. | 5 mM | 269 mg |
| Lecithin | 1.5 mM | 114 mg |
| pH 6.8 Buffer | Qs | Qs 100 ml |
| Composition of pH 6.8 Buffer | | |
| | Conc. | Quantity per L |
| $KH_2PO_4$ | 0.029 M | 3.947 g |
| KCl | 0.22 M | 16.401 g |
| NaOH | Qs pH 6.8 | |
| Water | N/A | Qs 1 L |

FaSSIF Preparation Procedure.

1. Preparation of 1 L of pH 6.8 Buffer Solution
   1.a. 3.947 g potassium phosphate and 16.401 g potassium chloride were dissolved in approx. 900 ml of water.
   1.b. The pH was adjusted to 6.8 by slow addition of 0.1N sodium hydroxide (Scharlau SO 0441010C) under magnetic stirring.
   1.c The mixture was diluted to a volume of 1000 ml with water.

2. Preparation of 100 ml of FaSSIF
   2.a. 269 mg NaTaurochol. (Aldrich T-4009) was dissolved in approx. 80 ml of pH 6.8 buffer.
   2.b. 114 mg lecithin (Sigma P-7318) was dissolved in this NaTaurochol/buffer solution (this was carried out with a nitrogen filled glove bag).
   2.c. The resulting mixture was diluted to a volume of 100 ml with further pH 6.8 buffer
   2.d. The final solution was covered with a layer of nitrogen or alternative inert gas. The bottle was sealed with parafilm and stored at 4° C.

B) FeSSIF is a solvent which simulates the Fed State of the Intestinal Fluid. (FeSSIF: Fed State Simulated Intestinal Fluid). Its composition is as given in the table below.

Composition of FeSSIF and the pH 5.0 Buffer Used in FeSSIF

| Composition of FeSSIF | | |
|---|---|---|
| | Conc. | Quantity per 100 ml |
| NaTaurochol. | 15 mM | 806.5 mg |
| Lecithin | 3.8 mM | 288 mg |
| pH 5.0 Buffer | Qs | Qs 100 ml |
| Composition of pH 5.0 Buffer | | |
| | Conc. | Quantity per L |
| Glacial Acetic acid | 0.137 M | 8.250 ml |
| KCl | 0.20 M | 15.2 g |
| NaOH | Qs pH 5.0 | |
| Water | N/A | Qs 1 L |

Reference(s): Galia, Nicolaides, Horter, Lobenberg, Reppas, and Dressman—Pharmaceutical Research, Vol. 15, No. 5, 1998

FeSSIF Preparation Procedure.

1. Prepare 1 L of pH 5 Buffer Solution 1.a. 15.2 g potassium chloride and 8.25 ml glacial acetic acid were dissolved in approx. 900 ml of water.

1.b. The pH was adjusted to 5 by slow addition of NaOH 0.1N (Scharlau SO 0441010C) under magnetic stirring.

1.c The mixture was diluted to a volume of 1000 ml with water.

2. Preparation of 100 mL of FeSSIF 2.a. 806.5 mg NaTaurochol (Aldrich T-4009) was dissolved in 80 ml of pH 5 buffer.

2.b. 288 mg lecithin (Sigma P-7318) was dissolved in this NaTaurochol/buffer solution (carried out with a nitrogen filled glove bag).

2.c. The resulting solution was diluted to a volume of 100 ml with pH 5 buffer.

2.d. The final solution was covered with a layer of nitrogen or alternative inert gas. The bottle was sealed with parafilm and stored at 4° C.

C) Solubility at pH 7.4 was determined in phosphate buffered saline (PBS) (Fluka cat. ref: 79383)

D) Solubility at pH 1.0 was determined in 0.1N HCl solution (Scharlau AL0744010C)

E) Solubility at pH 4.5 was determined in sodium citrate 0.5M solution. (Aldrich 25, 127-5)

Comparator Compounds

Four compounds are employed as comparator compounds. Compounds W, X, Y and Z were prepared as described in WO 91/13873 A1, and are:

Compound W: Example 87 in WO 91/13873 A1: 5'-Bromo-2',6'-dimethyl-2,3'-bipyridin-4'-(1'H)-one;

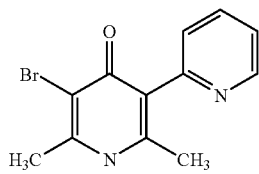

Compound X: Example 7 in WO 91/13873 A1: 3-(4'-chloro-4-biphenyl)-2,6-dimethylpyridine-4 (1H)-one;

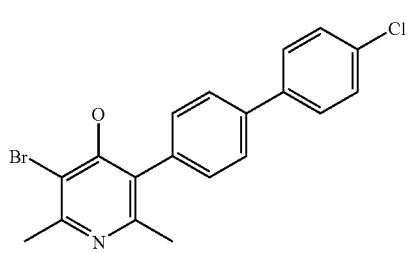

Compound Y: Example 15 in WO 91/13873 A1: 3-chloro-5-(4-(4-trifluoromethoxyphenoxy)phenyl)-2,6-dimethylpyridin-4(1H)-one;

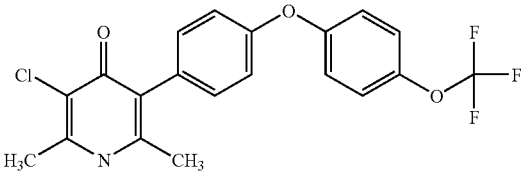

Compound Z: Example 42a in WO 91/13873 A1: 3-Chloro-2,6-dimethyl-5-(4-{[3-(trifluoromethyl)phenyl]oxy}phenyl)-4(1H)pyridinone;

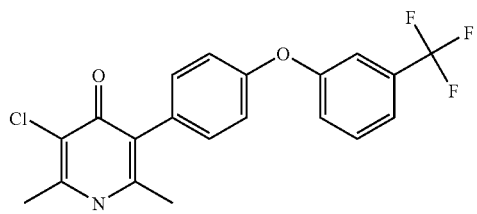

Results of in Vitro Activity Assay and Solubility Determination Assays

In Vitro Assay

All Examples of the invention (Examples 1-73) described hereinabove were found to have an $IC_{50}$ value of less than 225 ng/ml.

Examples 1-41, 43-64 and 71 described hereinabove were found to have an $IC_{50}$ value of less than 125 ng/ml.

Examples 42, 65-70, 72 and 73 have utility as intermediates for preparation of other compounds of Formula I.

Comparator compounds X, Y and Z were found to have an $IC_{50}$ value of less than 125 ng/ml. Comparator compound W was found to have an $IC_{50}$ value of 500 ng/ml.

Solubility Determination Assays

Solubility data for those compounds of the present invention which were tested in the solubility assays described hereinabove are shown in the table below. Comparative solubility data for comparator compounds X, Y and Z is also shown in the table below. The solubility of comparator compound W was not measured.

Solubility Table

| Structure | Example | Solubility at pH 1 (HCl) µg/ml | Solubility at pH 4.5 (Na citrate) µg/ml | Solubility at pH 7.4 (PBS) µg/ml | Solubility in FaSSIF µg/ml | Solubility in FeSSIF µg/ml |
|---|---|---|---|---|---|---|
| 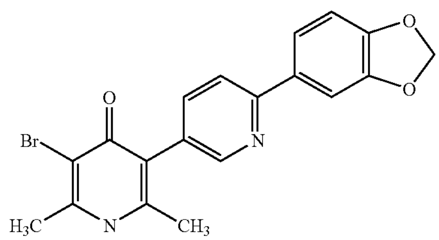 | 53 | *** | * |  | * | NT |
| 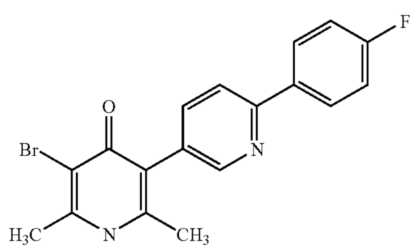 | 22 | *** |  |  |  | NT |
| 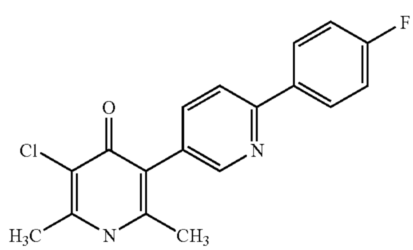 | 36 | *** |  |  |  | NT |
| 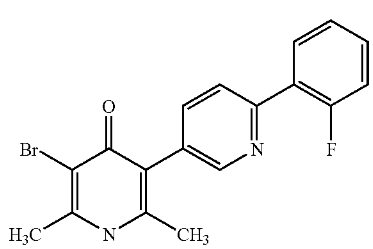 | 23 | *** | * |  |  | NT |
| 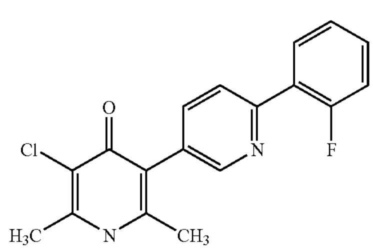 | 37 | *** |  |  | ** | NT |

-continued
Solubility Table
| Structure | Example | Solubility at pH 1 (HCl) μg/ml | Solubility at pH 4.5 (Na citrate) μg/ml | Solubility at pH 7.4 (PBS) μg/ml | Solubility in FaSSIF μg/ml | Solubility in FeSSIF μg/ml |
|---|---|---|---|---|---|---|
| 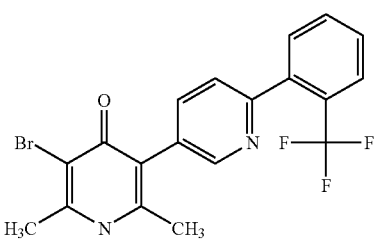 | 18 | *** |  |  | ** | NT |
| 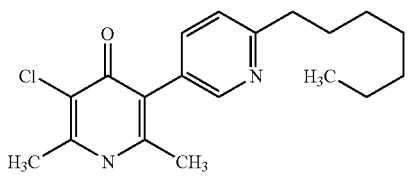 | 48 | *** | * |  | **** | NT |
| 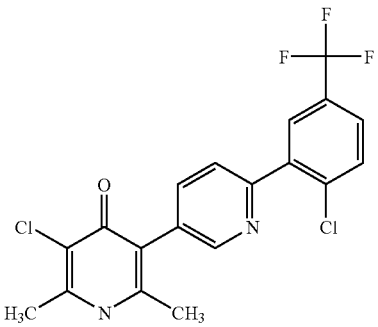 | 57 | ***** | * | * | * | ** |
| 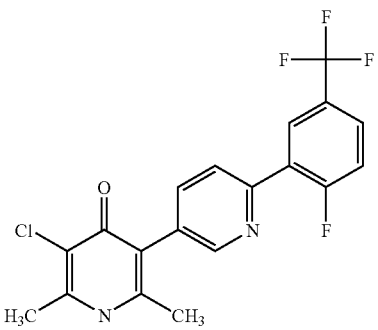 | 56 | ***** | * | * |  | ** |
| 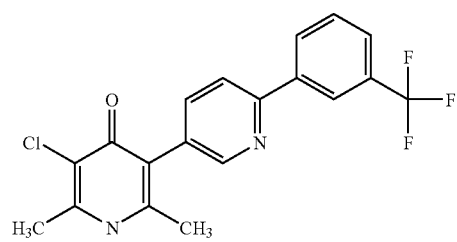 | 31 | *** |  | * | ** | NT |

-continued

Solubility Table

| Structure | Example | Solubility at pH 1 (HCl) μg/ml | Solubility at pH 4.5 (Na citrate) μg/ml | Solubility at pH 7.4 (PBS) μg/ml | Solubility in FaSSIF μg/ml | Solubility in FeSSIF μg/ml |
|---|---|---|---|---|---|---|
| (structure) | 45 | ***** | **** | *** | **** | NT |
| (structure) ClH | 38 | ***** | * | * | ** | *** |
| (structure) | 21 | ***** | *** | ** | *** | NT |
| (structure) | 44 | ***** | **** | ** | **** | NT |
| (structure) | 17 | ***** | * | * | ** | NT |

-continued

Solubility Table

| Structure | Example | Solubility at pH 1 (HCl) µg/ml | Solubility at pH 4.5 (Na citrate) µg/ml | Solubility at pH 7.4 (PBS) µg/ml | Solubility in FaSSIF µg/ml | Solubility in FeSSIF µg/ml |
|---|---|---|---|---|---|---|
| (structure) | 27 | ***** | * | * | ** | ** |
| (structure) | 20 | ***** | * | * | * | NT |
| (structure) | 30 | **** | * | * | ** | NT |
| (structure) | 58 | **** | * | * | * | ** |
| (structure) | 15 | **** | ** | ** | ** | NT |

-continued

Solubility Table

| Structure | Example | Solubility at pH 1 (HCl) μg/ml | Solubility at pH 4.5 (Na citrate) μg/ml | Solubility at pH 7.4 (PBS) μg/ml | Solubility in FaSSIF μg/ml | Solubility in FeSSIF μg/ml |
|---|---|---|---|---|---|---|
| (structure) | 26 | **** | * | * | **** | NT |
| (structure) | 16 | **** | * | * | * | NT |
| (structure) | 55 | **** | * | * | * | * |
| (structure) | 1 | *** | * | * | ** | ** |
| (structure) | 50 | *** | * | * | * | ** |

-continued
Solubility Table
| Structure | Example | Solubility at pH 1 (HCl) µg/ml | Solubility at pH 4.5 (Na citrate) µg/ml | Solubility at pH 7.4 (PBS) µg/ml | Solubility in FaSSIF µg/ml | Solubility in FeSSIF µg/ml |
|---|---|---|---|---|---|---|
| 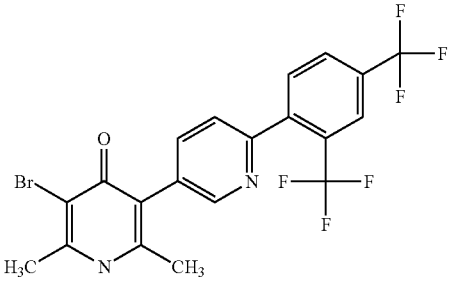 | 24 | *** | * | * | * | NT |
| 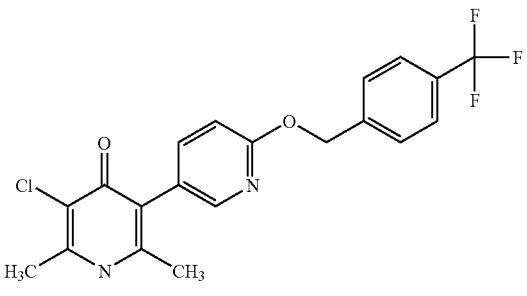 | 10 | *** | * | * | * | NT |
| 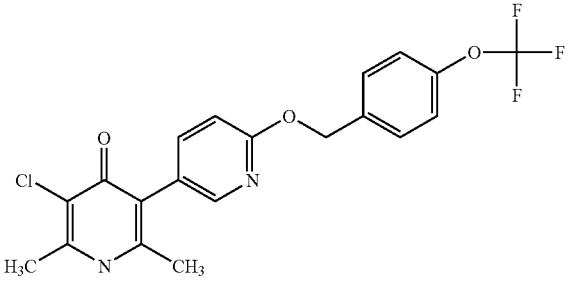 | 8 | ** | * | * | ** | NT |
| 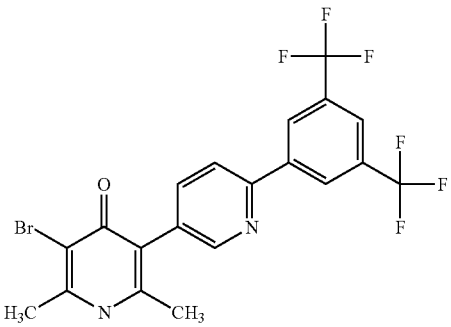 | 25 | ** | * | * | * | NT |
| 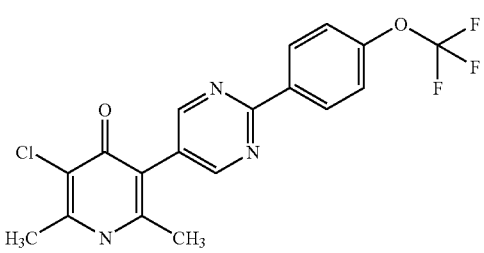 | 51 | ** | * | * |  | * |

-continued
Solubility Table
| Structure | Example | Solubility at pH 1 (HCl) μg/ml | Solubility at pH 4.5 (Na citrate) μg/ml | Solubility at pH 7.4 (PBS) μg/ml | Solubility in FaSSIF μg/ml | Solubility in FeSSIF μg/ml |
|---|---|---|---|---|---|---|
| 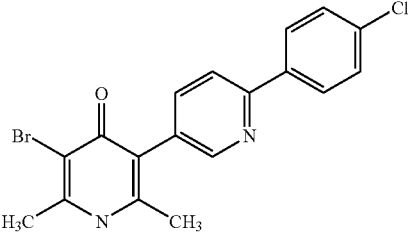 | 19 | ** |  |  |  | *** |
| 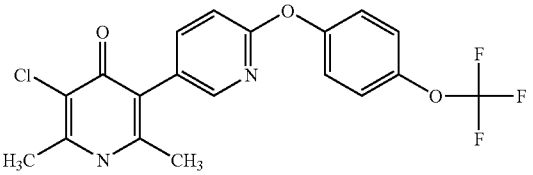 | 49 | *** | * | * | * | * |
| 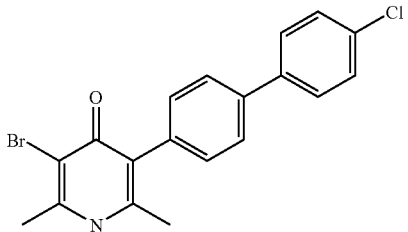 | comparator X | * | * | * | * | * |
| 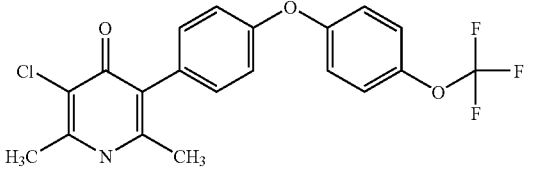 | comparator Y | * | * | * | * | ** |
| 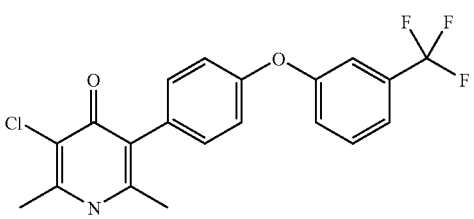 | comparator Z | * | * | * | * | ** |
Key to Table NT = not tested S = solubility in μg/ml *S < 1 1 < S < 5 *5 < S < 10 **10 < S < 50 ***S ≧ 50

The compounds of the invention shown in the table exhibit increased solubility at pH1 at least, as compared with compounds X, Y and Z of the prior art.

The invention claimed is:

1. A compound represented by the following Formula I:

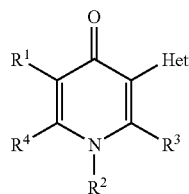

or a pharmaceutically acceptable salt thereof, wherein:
Het represents a 6-membered monocyclic heteroaromatic ring containing at least one nitrogen atom, wherein Het is substituted through a carbon atom with one group Z, wherein Z represents:
i) a phenyl or methylenedioxyphenyl group, either of which is optionally substituted with one or more $R^X$ groups;
ii) a $-OC_{1-6}$alkylphenyl group, wherein the phenyl portion is optionally substituted with one or more $R^X$ groups;
iii) a $C_{1-10}$alkyl, an Oaryl, a $-C_{1-6}$alkylaryl, a $-C_{2-6}$alkenylaryl or a $-C_{2-6}$alkynylaryl group, wherein any aryl portion is optionally substituted with one or more $R^X$ group;
$R^X$ represents halogen, cyano, $-NR^AR^B$, $C_{1-6}$alkyl, $C_{1-6}$alkoxy or $C_{1-6}$alkylS(O)$_m$—;
m represents 0-2;
$R^1$ represents halogen, hydrogen, or cyano;
$R^2$ resents hydrogen, hydroxy, $-C(O)R^Y$, $-C(O)OH$ or $C_{1-6}$alkyl optionally substituted by halogen, hydroxy, $-C(O)OH$, $-C(O)R^Y$ or $-NR^AR^B$;
$R^A$ and $R^B$ independently represent hydrogen or $C_{1-6}$alkyl;
$R^Y$ represents $C_{1-6}$alkoxy or $C_{1-6}$alkyl; and
$R^3$ and $R^4$ are independently $C_{1-6}$alkyl.

2. The compound according to claim 1, or a pharmaceutically acceptable salt thereof, wherein Het represents a substituted pyridinyl or a substituted pyrimidinyl group.

3. The compound according to claim 2, or a pharmaceutically acceptable salt thereof wherein Het represents a substituted pyridinyl group.

4. The compound according to claim 1, or a pharmaceutically acceptable salt thereof wherein Z represents phenyl, optionally substituted with one or more $R^X$ groups.

5. The compound according to claim 1, or a pharmaceutically acceptable salt thereof wherein Z represents —Obenzyl, optionally substituted with one or more $R^X$ groups.

6. The compound according to claim 1, or a pharmaceutical acceptable salt thereof, wherein Z represents $C_{1-10}$alkyl, phenoxy, $C_{2-6}$alkylaryl or $C_{2-6}$alkynylaryl, wherein any aryl group is optionally substituted with one or more groups selected from the list: halogen, $C_{1-6}$alkyl, $C_{1-6}$alkoxy.

7. The compound according to claim 2, or a pharmaceutically acceptable salt thereof, wherein $R^X$ represents halogen, $C_{1-6}$alkyl or $C_{1-6}$alkoxy.

8. The compound according claim 2, or a pharmaceutically acceptable salt thereof, wherein $R^1$ represents halogen.

9. The compound according to claim 8, or a pharmaceutically acceptable salt thereof, wherein $R^2$ represents hydrogen.

10. The compound according to claim 1, or a pharmaceutically acceptable salt thereof, wherein the compound is selected from group consisting of:
5-Bromo-2,6-dimethyl-6'-{[4-(trifluoromethoxy)benzyl]oxy}-3,3'-bipyridin-4(1H)-one;
5-Bromo-2,6-dimethyl-6'-{[3-(trifluoromethyl)benzyl]oxy}-3,3'-bipyridin-4(1H)-one;
5-Bromo-2,6-dimethyl-6'-{[4-(trifluoromethyl)benzyl]oxy}-3,3'-bipyridin-4(1H)-one;
5-Bromo-2,6-dimethyl-6'-{[2-(trifluoromethyl)benzyl]oxy}-3,3'-bipyridin-4(1H)-one;
5-Bromo-2,6-dimethyl-6'-{[3,5-bis(trifluoromethyl)benzyl]oxy}-3,3'-bipyridin-4(1H)-one;
5-Bromo-6'-{[4-fluorobenzyl]oxy}-2,6-dimethyl-3,3'-bipyridin-4(1H)-one;
5-Bromo-6'-{[3,5-difluorobenzyl]oxy}-2,6-dimethyl-3,3'-bipyridin-4(1H)-one;
5-Chloro-2,6-dimethyl-6'-{[4-(trifluoromethoxy)benzyl]oxy}-3,3'-bipyridin-4(1H)-one;
5-Chloro-2,6-dimethyl-6'-{[3-(trifluoromethyl)benzyl]oxy}-3,3'-bipyridin-4(1H)-one;
5-Chloro-2,6-dimethyl-6'-{[4-(trifluoromethyl)benzyl]oxy}-3,3'-bipyridin-4(1H)-one;
5-Chloro-2,6-dimethyl-6'-{[2-(trifluoromethyl)benzyl]oxy}-3,3'-bipyridin-4(1H)-one;
5-Chloro-2,6-dimethyl-6'-{[3,5-bis(trifluoromethyl)benzyl]oxy}-3,3'-bipyridin-4(1H)-one;
5-Chloro-6'-{[4-fluorobenzyl]oxy}-2,6-dimethyl-3,3'-bipyridin-4(1H)-one;
5-Chloro-6'-{[3,5-difluorobenzyl]oxy}-2,6-dimethyl-3,3'-bipyridin-4(1H)-one;
5-Bromo-2,6-dimethyl-6'-{4-[(trifluoromethyl)oxy]phenyl}-3,3'-bipyridin-4(1H)-one;
5-Bromo-2,6-dimethyl-6'-{4-[trifluoromethyl]phenyl}-3,3'-bipyridin-4(1H)-one;
5-Bromo-2,6-dimethyl-6'-{3-[trifluoromethyl]phenyl}-3,3'-bipyridin-4(1H)-one;
5-Bromo-2,6-dimethyl-6'-{2-[trifluoromethyl]phenyl}-3,3'-bipyridin-4(1H)-one;
5-Bromo-6'-(4-chlorophenyl)-2,6-dimethyl-3,3'-bipyridin-4(1H)-one;
5-Bromo-6'-(3-chlorophenyl)-2,6-dimethyl-3,3'-bipyridin-4(1H)-one;
5-Bromo-6'-(2-chlorophenyl)-2,6-dimethyl-3,3'-bipyridin-4(1H)-one;
5-Bromo-6'-(4-fluorophenyl)-2,6-dimethyl-3,3'-bipyridin-4(1H)-one;
5-Bromo-6'-(2-fluorophenyl)-2,6-dimethyl-3,3'-bipyridin-4(1H)-one;
5-Bromo-2,6-dimethyl-6'-{2,4-bis[trifluoromethyl]phenyl}-3,3'-bipyridin-4(1H)-one;
5-Bromo-2,6-dimethyl-6'-{3,5-bis[trifluoromethyl]phenyl}-3,3'-bipyridin-4(1H)-one;
5-Bromo-6'-(4-n-butylphenyl)-2,6-dimethyl-3,3'-bipyridin-4(1H)-one;
5-Chloro-2,6-dimethyl-6'-{4-[(trifluoromethyl)oxy]phenyl}-3,3'-bipyridin-4(1H)-one;
5-Chloro-2,6-dimethyl-6'-{3-[(trifluoromethyl)oxy]phenyl}-3,3'-bipyridin-4(1H)-one;
5-Chloro-2,6-dimethyl-6'-{2-[(trifluoromethyl)oxy]phenyl}-3,3'-bipyridin-4(1H)-one;
5-Chloro-2,6-dimethyl-6'-{4-[trifluoromethy]phenyl}-3,3'-bipyridin-4(1H)-one;
5-Chloro-2,6-dimethyl-6'-{3-[trifluoromethyl]phenyl}-3,3'-bipyridin-4(1H)-one;
5-Chloro-2,6-dimethyl-6'-{2-[trifluoromethy]phenyl}-3,3'-bipyridin-4(1H)-one;

5-Chloro-6'-(4-chlorophenyl)-2,6-dimethyl-3,3'-bipyridin-4(1H)-one;
5-Chloro-6'-(3-chlorophenyl)-2,6-dimethyl-3,3'-bipyridin-4(1H)-one;
5-Chloro-6'-(2-chlorophenyl)-2,6-dimethyl-3,3'-bipyridin-4(1H)-one;
5-Chloro-6'-(4-fluorophenyl)-2,6-dimethyl-3,3'-bipyridin-4(1H)-one;
5-Chloro-6'-(2-fluorophenyl)-2,6-dimethyl-3,3'-bipyridin-4(1H)-one;
5-Chloro-2,6-dimethyl-6'-{4-[(trifluoromethyl)oxy]phenyl}-3,3'-bipyridin-4(1H)-one hydrochloride salt;
5-Bromo-6'-(4-n-butylphenyl)-2,6-dimethyl-3,3'-bipyridin-4(1H)-one hydrochloride salt;
5-Bromo-2,6-dimethyl-6'-{[4-(trifluoromethyl)phenyl]ethynyl}-3,3'-bipyridin-4(1H)-one;
5-Chloro-2,6-dimethyl-6'-{[4-(trifluoromethyl)phenyl]ethynyl}-3,3'-bipyridin-4(1H)-one;
5-Chloro-6'-{[2,4-difluorophenyl]ethynyl}-2,6-dimethyl-3,3'-bipyridin-4(1H)-one;
5-Bromo-2,6-dimethyl-6'-{2-[3-(trifluoromethyl)phenyl]ethyl}-3,3'-bipyridin-4(1H)-one;
5-Chloro-2,6-dimethyl-6'-{2-[3-(trifluoromethyl)phenyl]ethyl}-3,3'-bipyridin-4(1H)-one;
5-Chloro-2,6-dimethyl-6'-{2-[4-(trifluoromethyl)phenyl]ethyl}-3,3'-bipyridin-4(1H)-one;
5-Chloro-6'-{2-[2,4-difluorophenyl]ethyl}-2,6-dimethyl-3,3'-bipyridin-4(1H)-one;
5-Chloro-6'-(n-heptyl)-2,6-dimethyl-3,3'-bipyridin-4(1H)-one;
5-Chloro-6'-(n-heptyl)-2,6-dimethyl-3,3'-bipyridin-4(1H)-one hydrochloride salt;
5-Chloro-2,6-dimethyl-6'-({4-[(trifluoromethyl)oxy]phenyl}oxy)-3,3'-bipyridin-4(1H)-one;
3-Chloro-2,6-dimethyl-5-(5-nonyl-2-pyrimidinyl)-4(1H)-pyridinone;
3-Chloro-2,6-dimethyl-5-{2-[4-(trifluoromethyl)phenyl]-5-pyrimidinyl}-4(1H)-pyridinone;
5'-Chloro-2',6'-dimethyl-5-{2-[4-(trifluoromethyl)phenyl]ethyl}-2,3'-bipyridin-4'(1H)-one; 5-Bromo-2,6-dimethyl-3-(6-{[3,4-methylenedioxy]phenyl}-3,3'-bipyridin-4(1H)-one;
5-Chloro-2,6-dimethyl-3-(6-{[3,4-methylenedioxy]phenyl}-3,3'-bipyridin-4(1H)-one;
5-chloro-6'-[2-chloro-4-(trifluoromethyl)phenyl]-2,6-dimethyl-3,3'-bipyridin-4(1H)-one;
5-chloro-6'-[2-fluoro-5-(trifluoromethyl)phenyl]-2,6-dimethyl-3,3'-bipyridin-4(1')-one:
5-chloro-6'-[2-chloro-5-(trifluoromethyl)phenyl]-2,6-dimethyl-3,3'-bipyridin-4(1H)-one;
5-chloro-6'-[2-fluoro-4-(trifluoromethyl)phenyl]-2,6-dimethyl-3,3'-bipyridin-4(1H)-one;
5-Chloro-2,6-dimethyl-6'-{[4-butyloxy]phenyl}-3,3'-bipyridin-4(1H)-one;
5-Chloro-2,6-dimethyl-6'-{[3-chloro,4-propyloxy]phenyl}-3,3'-bipyridin-4(1H)-one;
5-Chloro-2,6-dimethyl-6'-{[4-isopropyloxy]phenyl}-3,3'-bipyridin-4(1H)-one;
5-Chloro-2,6-dimethyl-6'-{4-[2,2,2-trifluoroethoxy]phenyl}-3,3'-bipyridin-4(1H)-one;
5-Chloro-2,6-dimethyl-6'-{4-[difluoromethyl]phenyl}-3,3'-bipyridin-4(1H)-one;
3-Chloro-2,6-dimethyl-5-(5-(2-(4-trifluoromethylphenyl))pyrimidinyl)pyridin-4(1H)-one.

11. A method for the treatment of malaria comprising administering to a patient in need thereof an effective amount of the compound according to claim 1 or a pharmaceutically acceptable salt thereof.

12. A The method according to claim 11 wherein malaria is caused by infection with *Plasmodium falciparum*.

13. A pharmaceutical composition comprising the compound according to claim 1, or a pharmaceutically acceptable salt thereof, in admixture with one or more pharmaceutically acceptable carriers and/or excipients.

* * * * *